US008796290B2

(12) United States Patent
Ramdas et al.

(10) Patent No.: US 8,796,290 B2
(45) Date of Patent: Aug. 5, 2014

(54) SUBSTITUTED FUSED PYRIMIDINE COMPOUNDS, ITS PREPARATION AND USES THEREOF

(75) Inventors: Vidya Ramdas, Pune (IN); Summon Koul, Pune (IN); Sujay Basu, Pune (IN); Yogesh Waman, Pune (IN); Yogesh Shejul, Pune (IN); Dinesh Barawkar, Pune (IN); Venkata Poornapragnacharyulu Palle, Pune (IN)

(73) Assignee: Advinus Therapeutics Limited, Bangalore, Karnataka (IN)

( * ) Notice: Subject to any disclaimer, the term of this patent is extended or adjusted under 35 U.S.C. 154(b) by 0 days.

(21) Appl. No.: 13/508,672

(22) PCT Filed: Nov. 9, 2010

(86) PCT No.: PCT/IN2010/000732
§ 371 (c)(1),
(2), (4) Date: May 8, 2012

(87) PCT Pub. No.: WO2011/055391
PCT Pub. Date: May 12, 2011

(65) Prior Publication Data
US 2012/0225812 A1    Sep. 6, 2012

(30) Foreign Application Priority Data

Nov. 9, 2009  (IN) .......................... 2720/CHE/2009

(51) Int. Cl.
*A61K 31/522*  (2006.01)
*C07D 473/30*  (2006.01)

(52) U.S. Cl.
USPC .................. 514/263.34; 544/265

(58) Field of Classification Search
USPC .................. 514/263.1; 544/265
See application file for complete search history.

(56) References Cited

U.S. PATENT DOCUMENTS

| 2005/0119287 A1 | 6/2005 | Kalla et al. |
| 2006/0281927 A1 | 12/2006 | Tomisawa et al. |
| 2008/0194593 A1 | 8/2008 | Kalla et al. |

FOREIGN PATENT DOCUMENTS

| EP | 0374808 B1 | 4/1996 |
| EP | 1283056 A1 | 2/2003 |
| EP | 1532150 B1 | 6/2008 |
| WO | 0010391 A1 | 3/2000 |
| WO | 0073307 A2 | 12/2000 |
| WO | 0125210 A2 | 4/2001 |
| WO | 0158241 A2 | 8/2001 |
| WO | 02055083 A1 | 7/2002 |
| WO | 03000694 A1 | 1/2003 |
| WO | 03002566 A1 | 1/2003 |
| WO | 03006465 A1 | 1/2003 |
| WO | 03035639 A1 | 5/2003 |
| WO | 03042214 A2 | 5/2003 |
| WO | 03053361 A2 | 7/2003 |
| WO | 03063800 A2 | 8/2003 |
| WO | 03082873 A1 | 10/2003 |
| WO | 2004106337 A1 | 12/2004 |
| WO | 2005021548 A2 | 3/2005 |
| WO | 2005042534 A2 | 5/2005 |
| WO | 2005044245 A1 | 5/2005 |
| WO | 2006009698 A2 | 1/2006 |
| WO | 2006015357 A2 | 2/2006 |
| WO | 2006091896 A2 | 8/2006 |
| WO | 2006132275 A1 | 12/2006 |
| WO | 2007017096 A1 | 2/2007 |
| WO | 2007109547 A2 | 9/2007 |
| WO | 2007149277 A2 | 12/2007 |
| WO | 2008002902 A2 | 1/2008 |
| WO | 2010103547 A2 | 9/2010 |

OTHER PUBLICATIONS

Banker, Gilbert S. Modern Pharmaceutics 3rd ed. Marcel Dekker, Inc. New York, 1996.*
Hasko, Gyorgy. Nature Reviews Drug Discovery 7, (2008) 759-770.*
WebMD. Asthma Health Center: Asthma Prevention. May 13, 2012. < http://www.webmd.com/asthma/guide/asthma-prevention>.*
The Mayo Clinic. Obesity. Jun. 7, 2013. p. 16. < http://www.mayoclinic.com/health/obesity/DS00314>.*
Chan, E.S.L.,Et Al., "Adenosine A2A Receptors in Diffuse Dermal Fibrosis: Pathogenic Role in Human Dermal Fibroblasts and in a Murine Model of Scleroderma," Arthritis & Rheumatism 54(8): 2632-2642, Wiley 2006.
Spicuzza, L., Et Al., "Research Applications and Implications of Adenosine in Diseased Airways," Trends in Pharmacological Sciences 24(8): 409-413, Aug. 2003.

(Continued)

*Primary Examiner* — Golam M M Shameem
*Assistant Examiner* — Laura Daniel
(74) *Attorney, Agent, or Firm* — Merchant & Gould P.C.

(57) ABSTRACT

The present invention provides substituted fused pyrimidine compounds of formula (I), their tautomers, polymorphs, stereoisomers, prodrugs, solvates, pharmaceutically acceptable salts, pharmaceutical compositions containing them and methods of treating conditions and diseases that are mediated by adenosine receptor (AR) activity. The present invention also provides processes for preparation of compounds of formula (I).

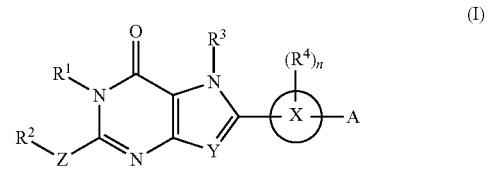

(I)

16 Claims, No Drawings

(56) References Cited

OTHER PUBLICATIONS

Feoktistov, I., and Biaggioni, I., "Adenosine A2B Receptors," Pharmacological Reviews 49(4): 381-402, The American Society for Pharmacology and Experimental Therapeutics (1997).

Adenosine A2B Receptors: A Novel Therapeutic Target in Asthma? Trends in Pharmacological Sciences, vol. 19, Issue 4, Apr. 1, 1998, pp. 148-153.

Fozard, J.R. and Hannon J.P., "Adenosine Receptor Ligands: Potential as Therapeutic Agents in Asthma and COPD," Pulmonary Pharmacology & Therapeutics 12(2): 111-114, Academic Press (1999).

Polosa, R. and Holgate, S.T., "Adenosine Receptors as Promising Therapeutic Targets for Drug Development in Chronic Airway Inflammation," Current Drug Targets 7(6): 699-706, Bentham Science Publishers (2006).

Synergy Between A2B Adenosine Receptors and Hypoxia in Activating Human Lung Fibroblasts, American Journal of Respiratory Cell Molecular Biology, 2005 vol. 32. pp. 2-8.

Feoktistov, I., Et Al., "Differential Expression of Adenosine Receptors in Humanendothelial Cells," Circulation Research 90: 531-538, American Heart Association (2002).

Chen, Et Al., "Functional Effects of Enhancing or Silencing Adenosine A2b Receptors in Cardiac Fibroblasts," American Journal of Physiology—Heart and Circulatory Physiology 287: H2478-H2486, The American Physiological Society (2004).

Rollins, B.M., Et Al., "A2B Adenosine Receptors Regulate the Mucus Clearance Component of the Lung's Innate Defense System," American Journal of Respiratory Cell and Molecular Biology 39: 190-197, The American Thoracic Society (2008).

Abo-Salem, O.M., Et Al., "Antinociceptive Effects of Novel A2B Adenosine Receptor Antagonists," The Journal of Pharmacology and Experimental Therapeutics 308: 358-366, The American Society for Pharmacology and Experimental Therapeutics (2004).

Rüsing Et. Al., "The Impact of Adenosine and A2B Receptors on Glucose Homoeostasis" Journal of Pharmacy and Pharmacology Dec. 2006; 58(12): 1639-45.

Wilson., "Adenosine Receptors and Asthma in Humans", British Journal of Pharmacology (2008) 155,475-486.

Obiefuna, P.C.M. Et Al., "A Novel A1 Adenosine Receptor Antagonist, L-97-1 [3-[2-(4-Aminophenyl)-Ethyl]-8-Benzyl-7-{2-Ethyl-(2-Hydroxy-Ethyl)-Amino]-Ethyl}-1-Propyl-3,7-Dihydro-Purine-2,6-Dione], Reducesallergic Responses to House Dust Mite in an Allergic Rabbitmodel of Asthma," The Journal of Pharmacology and Experimental Therapeutics 315: 329-336, The American Society for Pharmacology and Experimental Therapeutics (2005).

Nadeem, A., Et Al., "Adenosine A1 Receptor Antagonist Versus Montelukast on Airway Reactivity and Inflammation," European Journal of Pharmacology 551(1-3): 116-124, Elsevier B.V. (2006).

Wilcox, C.S., Et Al., "Natriuretic and Diuretic Actions of a Highly Selectiveadenosine A1 Receptor Antagonist," Journal of the American Society of Nephrology 10: 714-720, American Society of Nephrology (1999).

Gottlieb, S.S., Et Al., "BG9719 (CCT-124), An A1 Adenosine Receptor Antagonist, Protects Against the Decline in Renal Function Observed With Diuretic Therapy," Circulation 105: 1348-1353, American Heart Association (2002).

Auchampach, "Comparison of Three Different A1 Adenosine Receptor Antagonists on Infarct Size and Multiple Cycle Ischemic Preconditioning in Anesthetized Dogs," The Journal of Pharmacology and Experimental Therapeutics 308: 846-856, The American Society for Pharmacology and Experimental Therapeutics (2004).

Ben C.G. Et Al, "Myocardial Protection by Brief Ischemia in Noncardiac Tissue" Circulation. 1996; 94: 2193-2200.

Forman, M.B., Et Al., "Sustained Reduction in Myocardial Reperfusion Injury With an Adenosine Receptor Antagonist: Possible Role of the Neutrophil Chemoattractant Response," The Journal of Pharmacology and Experimental Therapeutics 292: 929-938, The American Society for Pharmacology and Experimental Therapeutics (2000).

Fishman and Bar-Yehuda, "Pharmacology and Therapeutic Applications of A3 Receptor Subtype", Current Topics in Medicinal Chemistry 2003, 3, 463-469.

Headrick, J.P. and Peart, J., "A3 Adenosine Receptor-Mediated Protection of the Ischemic Heart," Vascular Pharmacology 42(5-6): 271-279, Elsevier Inc. (2005).

Patane, Emanuele, Et Al., "Synthesis of 3-Arylpiperazinylalkylpyrrolo [3,2-d]pyrimidine-2,4-dione Derivatives as Novel, Potent, and Selective α1-Adrenoceptor Ligands," J. Med. Chem. 48: 2420-2431 (2005).

Chen, Ning, Et Al., "A Short, Facile Synthesis of 5-Substituted 3-Amino 1H-pyrrole-2-carboxylates," J. Org. Chem 65: 2603-2605 (2000).

International Search Report dated Feb. 24, 2011, for related International Patent Application No. PCT/IN2010/000732.

Kalla et al., "Recent advances in adenosine receptor (AR) ligands in pulmonary diseases", Ann Rep Med Chem, 44(13):265-277 (2009).

Muller et al., "Recent development in adenosine receptor ligands and their potential as novel drugs", Biochim Biophys Acta., 1808(5):1290-1308 (May 2011).

* cited by examiner

SUBSTITUTED FUSED PYRIMIDINE COMPOUNDS, ITS PREPARATION AND USES THEREOF

This application is a National Stage Application of PCT/IN2010/000732, filed 9 Nov. 2010, which claims benefit of Serial No. 2720/CHE/2009, filed 9 Nov. 2009 in India and which applications are incorporated herein by reference. To the extent appropriate, a claim of priority is made to each of the above disclosed applications.

FIELD OF THE INVENTION

The present invention relates to a series of novel substituted fused pyrimidine compounds of formula (I), their tautomers, polymorphs, stereoisomers, prodrugs, solvates, pharmaceutically acceptable salts, pharmaceutical compositions containing them and methods of treating conditions and diseases that are mediated by adenosine receptor (AR) activity.

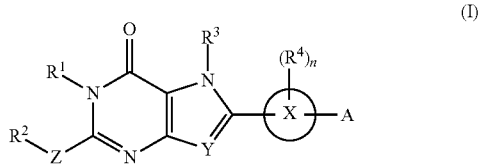

(I)

These compounds are useful in the treatment, prevention or suppression of diseases and disorders that may be susceptible to improvement by antagonism of the adenosine receptor, such as asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, and/or autoimmune diseases.

BACKGROUND OF THE INVENTION

Adenosine is known to be an endogenous modulator of a number of physiological functions and these are mediated by the interaction with different membrane specific receptors which belong to the family of receptors coupled with G proteins. Adenosine exerts effects in cardiovascular, central nervous, respiratory systems, kidney, adipose and platelets. Recent advances in molecular biology coupled with several pharmacological studies have lead to identification of at least four subtypes of adenosine receptors, $A_1$, $A_{2a}$, $A_{2b}$ and $A_3$.

In the central nervous system, $A_{2a}$ antagonists can have antidepressant properties and stimulate cognitive functions. There is fairly convincing prospective epidemiological evidence of a protective effect of caffeine against Parkinson's disease. Moreover, data has shown that $A_{2a}$ receptors density is very high in the basal ganglia, known to be important in the control of movement. Hence, selective $A_{2a}$ antagonists can improve motor impairment due to neurodegenerative diseases such as Parkinson's disease, senile dementia as in Alzheimer's disease, psychoses and stroke. $A_{2a}$ antagonists may also be employed for the treatment or management of attention related disorders such as attention deficit disorder and attention deficit hyperactivity disorder, extra pyramidal syndrome, e.g., dystonia, akathisia, pseudoparkinsonism and tardive dyskinesia, and disorders of abnormal movement such as restless leg syndrome and periodic limb movement in sleep. Several of these indications have been disclosed in patent applications (eg. WO 02/055083, WO 05/044245 and WO 06/132275). Adenosine $A_{2a}$ antagonists are also useful agents for the treatment of amyotrophic lateral sclerosis, cirrhosis, and fibrosis and fatty liver (US2007037033, WO 01/058241). $A_{2a}$ receptor antagonists are also useful for the mitigation of addictive behavior (WO 06/009698) and for the treatment and prevention of dermal fibrosis in diseases such as scleroderma (Arthritis & Rheumatism, 54(8), 2632-2642, 2006).

Adenosine signaling is known to serve apoptotic, angiogenic and pro-inflammatory functions and might be relevant to the pathogenesis of asthma and chronic obstructive pulmonary disease (Trends in Pharmacological Sciences, Vol. 24, No. 8, August 2003). Extracellular adenosine acts as a local modulator with a generally cytoprotective function in the body. Its effects on tissue protection and repair fall into four categories: increasing the ratio of oxygen supply to demand; protecting against ischaemic damage by cell conditioning; triggering anti-inflammatory responses; and the promotion of angiogenesis.

The $A_{2B}$ adenosine receptor subtype (see Feoktistov, I., Biaggioni, I. Pharmacol. Rev. 1997, 49, 381-402) has been identified in a variety of human and murine tissues and is involved in the regulation of vascular tone, smooth muscle growth, angiogenesis; hepatic glucose production, bowel movement, intestinal secretion, and mast cell degranulation. $A_{2B}$ receptors have been implicated in mast cell activation and asthma, control of vascular tone, cardiac myocyte contractility, cell growth and gene expression, vasodilation, regulation of cell growth, intestinal function, and modulation of neurosecretion (Pharmacological Reviews Vol. 49, No. 4).

$A_{2B}$ receptors modulate mast cell function. Adenosine activates adenylate cyclase and protein kinase C, and potentiates stimulated mediator release in mouse bone marrow derived mast cells. (TiPS—April 1998 (Vol. 19)). Activation of $A_{2B}$ receptors in HMC-1 augments IL-8 release and potentiates PMA induced secretion of IL-8. Thus, adenosine would contribute to the asthmatic response by acting on the mast cell to enhance the release of proinflammatory mediators. (*Pulmonary Pharmacology & Therapeutics* 1999, 12, 111-114). In COPD, transformation of pulmonary fibroblasts into myofibroblasts is considered a major mechanism. Activation of the $A_{2B}$ AR is involved in this process. Selective $A_{2B}$ antagonists are expected to have beneficial effect on pulmonary fibrosis (*Curr. Drug Targets*, 2006, 7, 699-706; *Am. J. Resper. Cell. Mol. Biol.*, 2005, 32, 228). $A_{2B}$ antagonists can be used as wound healing agents. Activation of the $A_{2B}$ AR promotes angiogenesis by increasing the release of angiogenic factors and $A_{2B}$ antagonists are useful to block angiogenesis (*Circ. Res.*, 2002, 90, 531-538). $A_{2B}$ AR may be involved in the inhibition cardiac fibroblast (CF) proliferation (*Am. J. Physiol. Heart Circ. Physiol.*, 2004, 287, H2478-H2486). Adenosine stimulates Cl-secretion in the intestinal epithelia pointing towards a possible treatment for cystic fibrosis patients with CFTR mutation (*Am. J. Respir. Cell Mol. Biol.*, 2008, 39, 190-197). High affinity $A_{2B}$ antagonists are effective in hot plate model suggestive of the role of $A_{2B}$ in nociception and can be used as potential analgesic agents (The *J. of Pharmacol. and Exp. Ther.*, 2004, 308, 358-366).

$A_{2B}$ receptor is involved in release of IL-6. Increasing evidence suggests that IL-6 plays a role in Alzheimer's disease in the context of inflammatory process associated with disease. Hence $A_{2B}$ receptor antagonist might be useful for Alzheimer's disease.

The $A_{2B}$ ARs are involved in the stimulation of nitric oxide production during $Na^+$-linked glucose or glutamine absorption. They are involved in glucose production in hepatocytes upon agonist stimulation. $A_{2B}$-receptor antagonists showed an anti-diabetic potential mainly by increasing plasma insulin levels under conditions when the adenosine tonus was elevated in-vivo and increased insulin release in-vitro (J Pharm. Pharmacol. 2006 December; 58(12):1639-45). Thus $A_{2B}$ antagonists may serve as a novel target for the treatment of this metabolic disease.

In view of the physiological effects mediated by adenosine receptor, several $A_{2B}$ receptor antagonists have been recently disclosed for the treatment or prevention of asthma, bronchoconstriction, allergic diseases, hypertension, atherosclerosis, reperfusion injury, myocardial ischemia, retinopathy, inflammation, gastrointestinal tract disorders, cell proliferation diseases and/or diabetes mellitus. See for example WO2008002902, WO2007149277, WO2007017096, WO2007109547, WO2006091896, WO2006015357, WO2005042534, WO2005021548, WO2004106337, WO2003000694, WO2003082873, WO2003006465, WO2003053361, WO2003002566, WO2003063800, WO2003042214, WO2003035639, EP1283056, WO200073307, WO2000125210, WO2000073307, US20050119287, US20060281927.

It has now been found that compounds of the present invention are potent antagonists of the $A_{2B}$ adenosine receptor and can therefore be used in the treatment of the diseases mentioned herein above.

Under normal physiological conditions, $A_1$ ARs are quiescent; however, $A_1$ ARs are upregulated in conditions of stress, such as ischaemia, and in conditions of inflammation, typified by the inflammatory airway involvement in human asthmatics. $A_1$ ARs are upregulated in airway epithelium and bronchial smooth muscle in human asthmatics. $A_1$ ARs have been described on a number of different human cell types that are important in the pathophysiology of asthma, including APCs, human airway epithelial and bronchial smooth muscle cells, lymphocytes, mast cells, neutrophils, monocytes, macrophages, fibroblasts and endothelial cells. Activation of $A_1$ ARs on these different cell types induces the release of mediators and cytokines that lead to airway hyperreactivity, inflammation and airway remodelling. Activation of $A_1$ ARs on human asthmatic bronchial tissue produces bronchoconstriction. On human airway epithelial cells, activation of $A_1$ ARs causes an increase in expression of the MUC 2 gene responsible for mucus hypersecretion. Moreover, activation of $A_1$ ARs on a number of different human cells produces pro-inflammatory effects. Taken together, these effects of $A_1$ ARs in humans suggest that the $A_1$ AR antagonists could play potential therapeutic role in inflammatory diseases (C N Wilson, British J. of Pharm., 2008, 155, 475-86 and references cited therein). $A_1$ AR antagonists have been shown to have efficacy in rodent models of asthma and inflammation ((J. Pharmacol. Exp. Ther. 315, 329-336, 2005; Eur. J. Pharmacol., 551, 116-124, 2006).

$A_1$ antagonists have also been shown to have therapeutic potential in diseases such as hypertension, congestive heart failure where underlying mechanism is diuresis. There are several compounds in development for these indications (J. Am. Soc. Nephrol. 10, 714-720, 1999; Circulation, 105, 1348-1353, 2002; J. Pharmacol. Exp. Ther. 308, 846-856, 2004).

$A_1$ AR antagonists are reported to reduce infarct size. It has been suggested that the ability of $A_1$ AR antagonists to reduce the infarct size is also mediated by antagonism at $A_{2B}$ AR (Circulation, 1996, 9, 94; J. Pharmacol. Exp. Ther., 2000, 292, 3, 929-938).

Activation of $A_3$ ARs induces the release of preformed mediators from basophils and produces bronchoconstriction, eosinophil migration into airways and mucus hypersecretion in animals, $A_3$ AR antagonists have been recommended for development as anti-asthma drugs (Fishman and Bar-Yehuda, 2003; Nadeem and Mustafa, 2006). $A_3$ AR antagonists have also been shown to play therapeutic role in various diseases including cardio-protection (Vasc. Pharmacol., 2005, 42, 271; J. Pharm. Exp. Ther., 2006, 319, 1200) and cancer (WO200010391).

Since several ARs have been implicated in asthma/COPD diseases pathophysiology, a pan AR antagonist may have therapeutic advantage.

It has now been found that some of the compounds of the present invention are non-selective antagonists of ARs and can therefore be used in the treatment of above mentioned diseases.

SUMMARY OF THE INVENTION

The present invention provides compounds of formula (I), their tautomers, polymorphs, stereoisomers, prodrugs, solvates, pharmaceutically acceptable salts, pharmaceutical compositions containing them and methods of treating conditions and diseases that are mediated by adenosine receptor activity,

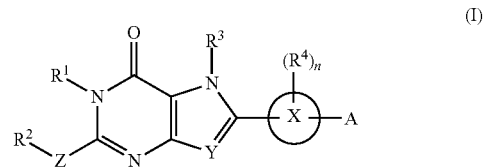

(I)

wherein
Y is selected from N or CR; R is selected from H, hydroxy, alkoxy, alkyl, aryl;
$R^1$ is selected from a group consisting of alkyl, alkenyl and alkynyl, wherein one or more methylene groups is optionally replaced by groups selected from —O—, —S(O)p-, $NR^aR^a$, or —C(O), and wherein heteroatom is not adjacent to N in the ring; p is selected from 0, 1 or 2;
    wherein alkyl, alkenyl and alkynyl are unsubstituted or independently substituted with alkoxy, acyl, acylamino, acyloxy, amino, monoalkylamino, dialkylamino, aminocarbonyl, alkoxycarbonylamino, azido, cyano, halogen, haloalkyl, hydroxy, hydroxyalkyl, keto, thiocarbonyl, carboxy, alkylcarboxy, carboxyalkyl, —$SO_3H$, aminocarbonylamino, hydroxyamino, alkoxyamino, or nitro;
Z is selected from a bond, —O—, —S(O)p-, —$NR^aC(O)$— or —$NR^aS(O)_2$—;
$R^2$ is selected from a group consisting of alkyl, alkenyl, alkynyl, haloalkyl, aryl, arylalkyl, hydroxyalkyl, carboxyalkyl, cycloalkyl, cycloalkylalkyl, heterocyclyl, heterocyclylalkyl, heteroaryl and heteroarylalkyl;
    wherein alkyl, alkenyl, alkynyl, cycloalkyl, cycloalkylalkyl, arylalkyl, aryl, heteroaryl, heteroarylalkyl, heterocyclyl, and heterocyclylalkyl are unsubstituted or independently substituted with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, haloalkyl, perhaloalkyl, $CF_3$, $OCF_3$, hydroxy, hydroxyalkyl, keto, thiocarbonyl, carboxy, alkylcarboxy, carboxyalkyl, —$SO_3H$, aryl, aryloxy, cycloalkyloxy, heteroaryl, aminocarbonylamino, heteroaryloxy, heterocyclyl, heterocyclyloxy, hydroxyamino, alkoxyamino, nitro, —S(O)$_2$NR$^b$R$^b$, —NR$^b$S(O)$_2$R$^b$ or —S(O)$_p$R$^c$;

wherein each substituent is unsubstituted or substituted with 1, 2, or 3 substituents independently selected from alkyl, carboxy, carboxyalkyl, aminocarbonyl, hydroxy, alkoxy, halogen, CF$_3$, amino, substituted amino, cyano or —S(O)$_p$R$^d$;

R$^3$ is selected from a group consisting of hydrogen, alkyl, alkenyl, alkynyl, alkoxyalkyl and arylalkyl;

wherein alkyl, alkenyl, alkynyl, alkoxyalkyl and arylalkyl are unsubstituted or independently substituted with hydroxyl, alkyl, alkenyl, alkynyl or alkoxy;

X is selected from (C$_3$-C$_{12}$)cycloalkyl or (C$_1$-C$_{10}$)heterocyclyl wherein the heterocycle is connected through a carbon atom to the core ring;

R$^4$ is selected from hydrogen, cyano, hydroxyl, halogen, alkyl, alkenyl, alkynyl, haloalkyl, hydroxyalkyl, alkoxyalkyl, carboxy, carboxyalkyl, alkoxy or haloalkoxy;

A is selected from a bond, (C$_1$-C$_6$)alkyl, (C$_2$-C$_6$)alkenyl or (C$_2$-C$_6$)alkynyl group;

wherein 1 to 4 methylene groups are optionally replaced by groups independently selected from O, —S(O)$_p$—, —N(R$^a$)—, or —C(O)—;

wherein A is substituted with B; B is selected from hydrogen, heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy, —SO3H, aryl, aryloxy, cycloalkyloxy, heteroaryl, aminocarbonylamino, heteroaryloxy, heterocyclyl, heterocyclyloxy, hydroxyamino, alkoxyamino, nitro, S(O)2NRbRb, —NRbS(O)2Rb or —S(O)pRc;

wherein each substituent is unsubstituted or substituted with 1, 2, or 3 substituents independently selected from alkyl, carboxy, carboxyalkyl, aminocarbonyl, hydroxy, alkoxy, halogen, CF$_3$, amino, substituted amino, cyano or —S(O)$_p$R$^d$;

each R$^a$ is independently selected from the group consisting of hydrogen and alkyl;

each R$^b$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl;

R$^c$ is hydrogen, alkyl, aryl, heteroaryl or heterocyclyl;

R$^d$ is alkyl, aryl, or heteroaryl;

n is 1 or 2; and p is 0, 1 or 2;

with the proviso that— i. if A is bond, B and R$^4$ are each hydrogen, then Z is not a bond; and ii. if Z is a bond, then R$^2$ is not an alkyl, substituted with amino or substituted amino.

DETAILED DESCRIPTION OF THE INVENTION

Definitions

In the structural formulae given herein and throughout the present disclosure, the following terms have the indicated meaning, unless specifically stated otherwise.

The term "optionally substituted" as used herein means that the group in question is either unsubstituted or substituted with one or more of the substituents specified. When the group in question is substituted with more than one substituent, the substituent may be same or different.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methyl, ethyl, n-propyl, isopropyl, n-butyl, iso-butyl, t-butyl, n-hexyl, n-decyl, tetradecyl, and the like.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkyl" or "substituted alkylene" refers to: 1) an alkyl group or alkylene group as defined above, having 1, 2, 3, 4 or 5 substituents, preferably 1, 2 or 3 substituents, selected from the group consisting of alkenyl, alkynyl, alkoxy, cycloalkyl, cycloalkenyl, acyl, acylamino, acyloxy, amino, monoalkylamino, dialkylamino, arylamino, heteroarylamino, aminocarbonyl, alkoxycarbonylamino, azido, cyano, halogen, hydroxy, hydroxyalkyl, keto, thiocarbonyl, carboxy, carboxyalkyl, —SO$_3$H, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$, where each R$^a$ is independently selected from the group consisting of hydrogen, alkyl, cycloalkyl, cycloalkylalkyl, aryl, arylalkyl, heteroaryl heteroarylalkyl, heterocyclyl, heterocyclylalkyl, and heterocyclyloxy where R$^b$ is hydrogen, alkyl, aryl, heteroaryl or heterocyclyl. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF$_3$, amino, substituted amino, cyano, and —S(O)$_p$R$^c$, where R$^c$ is alkyl, aryl, or heteroaryl and p is 0, 1 or 2;

or 2) an alkyl group or alkylene group as defined above that is interrupted by 1, 2, 3, 4, 5, 6, 7, 8, 9 or 10 atoms independently selected from oxygen, sulfur and NR$^d$, where R$^d$ is selected from hydrogen, alkyl, cycloalkyl, cycloalkenyl, aryl, heteroaryl and heterocyclyl, carbonylalkyl, carboxyester, carboxyamide and sulfonyl. All substituents may be optionally further substituted by alkyl, alkoxy, halogen, CF$_3$, amino, substituted amino, cyano, or —S(O)$_p$R$^c$, in which R$^c$ is alkyl, aryl, or heteroaryl and p is 0, 1, or 2;

or 3) an alkyl or alkylene as defined above that has 1, 2, 3, 4 or 5 substituents as defined above, as well as interrupted by 1, 2, 3, 4, 5, 6, 7, 8, 9 or 10 atoms as defined above.

The term "alkenyl" refers to a monoradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 double bond (vinyl), preferably 1 double bond. Preferred alkenyl groups include ethenyl or vinyl(—CH=CH$_2$), 1-propylene or allyl (—CH$_2$CH=CH$_2$), isopropylene (—C(CH$_3$)=CH$_2$), bicyclo[2.2.1]heptene, and the like.

The term "alkenylene" refers to a diradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 double bond (vinyl), preferably 1 double bond.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, thiocarbonyl, carboxy, carboxyalkyl, $SO_3H$, aryl, aryloxy, heteroaryl, aminocarbonylamino, heteroaryloxy, heterocyclyl, heterocyclyloxy, hydroxyamino, alkoxyamino, nitro, $—S(O)_2NR^aR^a$, $—NR^aS(O)_2R^a$ and $—S(O)_pR^b$ where each $R^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; heterocyclyloxy where $R^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, $CF_3$, amino, substituted amino, cyano, and $—S(O)_pR^c$, where $R^c$ is alkyl, aryl, or heteroaryl and p is 0, 1 or 2.

The term "alkynyl" refers to a monoradical of an unsaturated hydrocarbon, preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 sites of acetylene (triple bond) unsaturation, preferably 1 triple bond. Preferred alkynyl groups include ethynyl, ($—C≡CH$), propargyl (or prop-1-yn-3-yl, $—CH_2C≡CH$), homopropargyl (or but-1-yn-4-yl, $—CH_2CH_2C≡CH$) and the like.

The term "alkynylene" refers to a diradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 sites of acetylene (triple bond) unsaturation, preferably 1 triple bond.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, $—SO_3H$, aryl, aryloxy, heteroaryl, aminocarbonylamino, heteroaryloxy, heterocyclyl, heterocyclyloxy, hydroxyamino, alkoxyamino, nitro, $—S(O)_2NR^aR^a$, $—NR^aS(O)_2R^a$ and $—S(O)_pR^b$, where each $R^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; heterocyclyloxy where $R^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, $CF_3$, amino, substituted amino, cyano, and $—S(O)_pR^c$ where $R^c$ is alkyl, aryl, or heteroaryl and p is 0, 1 or 2.

The term "cycloalkyl" refers to, unless otherwise mentioned, carbocyclic groups of from 3 to 20 carbon atoms having a single cyclic ring or multiple condensed rings which may be saturated or partially unsaturated. Such cycloalkyl groups include, by way of example, single ring structures such as cyclopropyl, cyclobutyl, cyclopentyl, cyclopentenyl, cyclohexyl, cyclohexenyl, cyclooctyl, and the like, or multiple ring structures such as adamantanyl, bicyclo[2.2.1]heptane, bicyclo[2.2.2]octane, 1,3,3-trimethylbicyclo[2.2.1]hept-2-yl, (2,3,3-trimethylbicyclo[2.2.1]hept-2-yl), or carbocyclic groups to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, oxo, thiocarbonyl, aryl, aryloxy, heteroaryl, aminosulfonyl, aminocarbonylamino, heteroaryloxy, heterocyclyl, heterocyclyloxy, hydroxyamino, alkoxyamino, nitro, $—C(O)R$ and $—S(O)_pR^b$, where R is hydrogen, hydroxyl, alkoxy, alkyl and cyclocalkyl, heterocyclyloxy where $R^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, $CF_3$, amino, substituted amino, cyano, and $—S(O)_pR^c$, where $R^c$ is alkyl, aryl, or heteroaryl and p is 0, 1 or 2.

"Halo" or "Halogen", alone or in combination with any other term means halogens such as chloro (Cl), fluoro (F), bromo (Br) and iodo (I).

"Haloalkyl" refers to a straight chain or branched chain haloalkyl group with 1 to 6 carbon atoms. The alkyl group may be partly or totally halogenated. Representative examples of haloalkyl groups include but are not limited to fluoromethyl, chloromethyl, bromomethyl, difluoromethyl, dichloromethyl, dibromomethyl, trifluoromethyl, trichloromethyl, 2-fluoroethyl, 2-chloroethyl, 2-bromoethyl, 2,2,2-trifluoroethyl, 3-fluoropropyl, 3-chloropropyl, 3-bromopropyl and the like.

The term "alkoxy" refers to the group R'"—O—, where R'" is optionally substituted alkyl or optionally substituted cycloalkyl, or optionally substituted alkenyl or optionally substituted alkynyl; or optionally substituted cycloalkenyl, where alkyl, alkenyl, alkynyl, cycloalkyl and cycloalkenyl are as defined herein. Representative examples of alkoxy groups include but are not limited to methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "aminocarbonyl" refers to the group —C(O)NR'R' where each R' is independently hydrogen, alkyl, aryl, heteroaryl, heterocyclyl or both R' groups are joined to form a heterocyclic group (e.g. morpholino). Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and $—S(O)_pR^c$, where $R^c$ is alkyl, aryl, or heteroaryl and p is 0, 1 or 2.

The term "acylamino" refers to the group —NR"C(O)R" where each R" is independently hydrogen, alkyl, aryl, heteroaryl, or heterocyclyl. Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and $—S(O)_pR^c$, where $R^c$ is alkyl, aryl, or heteroaryl and p is 0, 1 or 2.

The term "acyloxy" refers to the groups —OC(O)-alkyl, —OC(O)-cycloalkyl, —OC(O)-aryl, —OC(O)-heteroaryl, and —OC(O)-heterocyclyl. Unless otherwise constrained by the definition, all substituents may be optionally further substituted by alkyl, carboxy, carboxyalkyl, aminocarbonyl, hydroxy, alkoxy, halogen, $CF_3$, amino, substituted amino, cyano, or —S(O)$_p$R$^c$, where R$^c$ is alkyl, aryl, or heteroaryl and p is 0, 1 or 2.

"Alkoxyalkyl" refers to alkyl groups as defined above wherein at least one of the hydrogen atoms of the alkyl group is replaced by an alkoxy group as defined above. Representative examples of alkoxyalkyl groups include but are not limited to methoxymethyl, methoxyethyl, ethoxymethyl and the like.

"Aryloxyalkyl" refers to the group -alkyl-O-aryl. Representative examples of aryloxyalkyl include but are not limited to phenoxymethyl, naphthyloxymethyl, phenoxyethyl, naphthyloxyethyl and the like.

"Di alkylamino" refers to an amino group, to which two same or different straight chain or branched chain alkyl groups with 1 to 6 carbon atoms are bound. Representative examples of di alkylamino include but are not limited to dimethylamino, diethylamino, methylethylamino, dipropylamino, dibutylamino and the like.

"Cycloalkylalkyl" refers to an alkyl radical as defined above which is substituted by a cycloalkyl radical as defined above. Representative examples of cycloalkylalkyl include but are not limited to cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

"Aminoallyl" refers to an amino group that is attached to (C$_{1-6}$)alkylene as defined herein. Representative examples of aminoalkyl include but are not limited to aminomethyl, aminoethyl, 1-aminopropyl, 2-aminopropyl, and the like. The amino moiety of aminoalkyl may be substituted once or twice with alkyl to provide alkylaminoalkyl and dialkylaminoalkyl respectively. Representative examples of alkylaminoalkyl include but are not limited to methylaminomethyl, methylaminoethyl, methylaminopropyl, ethylaminoethyl and the like. Representative examples of dialkylaminoalkyl include but are not limited to dimethylaminomethyl, dimethylaminoethyl, dimethylaminopropyl, N-methyl-N-ethylaminoethyl and the like.

The term "aryl" refers to an aromatic carbocyclic group of 6 to 20 carbon atoms having a single ring (e.g. phenyl) or multiple rings (e.g. biphenyl), or multiple condensed (fused) rings (e.g. naphthyl or anthranyl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained the aryl or arylene groups may optionally be substituted with 1, 2, 3, 4 or 5 substituents, preferably 1, 2 or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, carboxy, carboxyalkyl, —SO$_3$H, aryl, aryloxy, heteroaryl, aminosulfonyl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$ where each R$^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl; where R$^b$ is hydrogen, alkyl, aryl, heterocyclyl or heteroaryl and p is 0, 1 or 2. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, $CF_3$, amino, substituted amino, cyano, and —S(O)$_p$R$^c$ where R$^c$ is hydrogen, alkyl, aryl, or heteroaryl and p is 0, 1 or 2.

The term "arylalkyl" refers to an aryl group covalently linked to an alkylene group, where aryl and alkylene are defined herein.

"Optionally substituted arylalkyl" refers to an optionally substituted aryl group covalently linked to an optionally substituted alkylene group. Such arylalkyl groups are exemplified by benzyl, phenethyl, naphthylmethyl, and the like.

The term "aryloxy" refers to the group aryl-O— wherein the aryl group is as defined above, and includes optionally substituted aryl groups as also defined above.

The term "arylthio" refers to the group —S-aryl, where aryl is as defined herein including optionally substituted aryl groups as also defined above.

The term "substituted amino" refers to the group —NR'R' where each R' is independently selected from the group consisting of hydrogen, alkyl, cycloalkyl, carboxyalkyl, alkoxycarbonyl, aryl, heteroaryl and heterocyclyl. Unless otherwise constrained by the definition, all substituents may optionally be further substituted by 1, 2 or 3 substituents independently selected from alkyl, carboxy, carboxyalkyl, aminocarbonyl, hydroxy, alkoxy, halogen, $CF_3$, amino, substituted amino, cyano, and —S(O)$_p$R$^c$, where R$^c$ is alkyl, aryl, or heteroaryl and p is 0, 1 or 2.

The term "carboxyalkyl" refers to the group -alkylene-C(O)OH.

The term "alkylcarboxyalkyl" refers to the group -alkylene-C(O)OR$^d$ where R$^d$ is alkyl, cycloalkyl, wherein alkyl, cycloalkyl are as defined herein, and may be optionally further substituted by alkyl, halogen, $CF_3$, amino, substituted amino, cyano, or —S(O)$_p$R$^c$, in which R$^c$ is alkyl, aryl, or heteroaryl and p is 0, 1 or 2.

The term "heteroaryl" refers to an aromatic cyclic group having 1, 2, 3, 4, 5, 6, 7, 8, 9, 10, 11, 12, 13, 14, or 15 carbon atoms and 1, 2, 3 or 4 heteroatoms selected from oxygen, nitrogen and sulfur within at least one ring. Such heteroaryl groups can have a single ring (e.g. pyridyl or furyl) or multiple condensed rings (e.g. indolizinyl, benzothiazolyl, or benzothienyl). Examples of heteroaryls include, but are not limited to [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, quinoxaline, quinazoline, cinnoline, pteridine, carbazole, carboline, phenanthridine, acridine, phenanthroline, isothiazole, phenazine, isoxazole, phenoxazine, phenothiazine, furan, thiophene, oxazole, thiazole, triazole, triazine and the like.

The term "heteroarylene" refers to a diradical of a heteroaryl group as defined above.

Unless otherwise constrained the heteroaryl or heterarylene groups can be optionally substituted with 1, 2, 3, 4 or 5 substituents, preferably 1, 2 or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, thiocarbonyl, carboxy, carboxyalkyl, —SO$_3$H, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$, where each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; where R$^b$ is hydrogen, alkyl, aryl, heterocyclyl or heteroaryl, and p is 0, 1 or 2. Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and —$S(O)_pR^c$, where $R^c$ is alkyl, aryl, or heteroaryl and n is 0, 1 or 2.

The term "heteroarylalkyl" refers to a heteroaryl group covalently linked to an alkylene group, where heteroaryl and alkylene are defined herein.

"Optionally substituted heteroarylalkyl" refers to an optionally substituted heteroaryl group covalently linked to an optionally substituted alkylene group. Such heteroarylalkyl groups are exemplified by 3-pyridylmethyl, quinolin-8-ylethyl, 4-methoxythiazol-2-ylpropyl, and the like.

The term "heterocyclyl" refers to a saturated or partially unsaturated group having a single ring or multiple condensed rings, unless otherwise mentioned, having from 1 to 40 carbon atoms and from 1 to 10 hetero atoms, preferably 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholinyl, piperidinyl, piperazinyl, dihydropyridinyl, tetrahydroquinolinyl and the like. Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, oxo, —C(O)R where R is hydrogen, hydroxyl, alkoxy, alkyl and cyclocalkyl, thiocarbonyl, carboxy, carboxyalkyl, aryl, aryloxy, heteroaryl, aminosulfonyl, aminocarbonylamino, heteroaryloxy, heterocyclyl, heterocyclyloxy, hydroxyamino, alkoxyamino, nitro, and —$S(O)_pR^b$, where $R^b$ is hydrogen, alkyl, aryl, heterocyclyl or heteroaryl and p is 0, 1 or 2. Unless otherwise constrained by the definition, all substituents may optionally be further substituted by 1-3 substituents selected from alkyl, carboxy; carboxyalkyl, aminocarbonyl, hydroxy, alkoxy, halogen, $CF_3$, amino, substituted amino, cyano, and —$S(O)R^c$, where $R^c$ is alkyl, aryl, or heteroaryl and n is 0, 1 or 2.

The term "heterocyclylalkyl" refers to a heterocyclyl group covalently linked to an alkylene group, where heterocyclyl and alkylene are defined herein.

"Optionally substituted heterocyclylalkyl" refers to an optionally substituted heterocyclyl group covalently linked to an optionally substituted alkylene group.

The term "heteroaryloxy" refers to the group heteroaryl-O—.

The term "thiol" refers to the group —SH.

The term "substituted alkylthio" refers to the group —S-substituted alkyl.

The term "heteroarylthio" refers to the group —S-heteroaryl wherein the heteroaryl group is as defined above including optionally substituted heteroaryl groups as also defined above.

The term "sulfoxide" refers to a group —S(O).

"Substituted sulfoxide" refers to a group —S(O)R, in which R is substituted alkyl, substituted aryl, or substituted heteroaryl, as defined herein.

The term "sulfone" refers to a group —$S(O)_2R$.

The term "substituted sulfone" refers to a group —$S(O)_2R$, in which R is alkyl, aryl, or heteroaryl.

The compounds of the present invention may have the ability to crystallize in more than one form, a characteristic known as polymorphism, and all such polymorphic forms ("polymorphs") are encompassed within the scope of the invention. Polymorphism generally can occur as a response to changes in temperature or pressure or both, and can also result from variations in the crystallization process. Polymorphs can be distinguished by various physical characteristics, and typically the x-ray diffraction patterns, solubility behavior, and melting point of the compound are used to distinguish polymorphs.

The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component, enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds.

Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the invention are congeners, analogs, hydrolysis products, metabolites and precursor or prodrugs of the compound. In general, unless otherwise indicated, all physical forms are equivalent for the uses contemplated herein and are intended to be within the scope of the present invention.

"Prodrug" refers to a derivative of a drug molecule as, for example, esters, carbonates, carbamates, ureas, amides or phosphates that requires a transformation within the body to release the active drug. Prodrugs are frequently, although not necessarily, pharmacologically inactive until converted to the parent drug. Prodrugs may be obtained by bonding a promoiety (defined herein) typically via a functional group, to a drug.

"Promoiety" refers to a group bonded to a drug, typically to a functional group of the drug, via bond(s) that are cleavable under specified conditions of use. The bond(s) between the drug and promoiety may be cleaved by enzymatic or non enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach or the agent may be supplied exogenously.

"Pharmaceutically acceptable salt" embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the invention are quaternary ammonium compounds wherein an equivalent of an anion (X—) is associated with the positive charge of the N atom. X— may be an anion of various mineral acids such as, for example, chloride, bromide, iodide, sulphate, nitrate, phosphate, or an anion of an organic acid such as, for example, acetate, maleate, fumarate, citrate, oxalate, succinate, tartarate, malate, mandelate, trifluoroacetate, methanesulphonate and p-toluenesulphonate. X— is preferably an anion selected from chloride, bromide, iodide, sulphate, nitrate, acetate, maleate, oxalate, succinate or trifluoroacetate. More preferably X— is chloride, bromide, trifluoroacetate or methanesulphonate.

The present invention provides compounds of formula I, or its tautomers, polymorphs, stereoisomers, prodrugs, solvate or a pharmaceutically acceptable salts thereof, pharmaceutical compositions containing them and methods of treating conditions and diseases that are mediated by adenosine receptor activity,

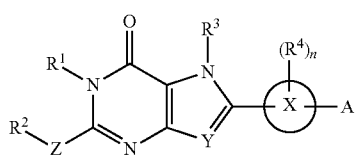

(I)

wherein

Y is selected from N or CR; R is selected from H, hydroxy, alkoxy, alkyl, aryl;

$R^1$ is selected from a group consisting of alkyl, alkenyl and alkynyl, wherein one or more methylene groups is optionally replaced by groups selected from —O—, —S(O)$_p$—, NR$^a$R$^a$, or —C(O), and wherein heteroatom is not adjacent to N in the ring; p is selected from 0, 1 or 2;
  wherein alkyl, alkenyl and alkynyl are unsubstituted or independently substituted with alkoxy, acyl, acylamino, acyloxy, amino, monoalkylamino, dialkylamino, aminocarbonyl, alkoxycarbonylamino, azido, cyano, halogen, haloalkyl, hydroxy, hydroxyalkyl, keto, thiocarbonyl, carboxy, alkylcarboxy, carboxyalkyl, —SO$_3$H, aminocarbonylamino, hydroxyamino, alkoxyamino, or nitro;

Z is selected from a bond, —O—, —S(O)$_p$—, —NR$^a$, —NR$^a$C(O)— or —NR$^a$S(O)$_2$—;

$R^2$ is selected from a group consisting of alkyl, alkenyl, alkynyl, haloalkyl, aryl, arylalkyl, hydroxyalkyl, carboxyalkyl, cycloalkyl, cycloalkylalkyl, heterocyclyl, heterocyclylalkyl, heteroaryl and heteroarylalkyl;
  wherein alkyl, alkenyl, alkynyl, cycloalkyl, cycloalkylalkyl, arylalkyl, aryl, heteroaryl, heteroarylalkyl, heterocyclyl, and heterocyclylalkyl are unsubstituted or independently substituted with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, haloalkyl, perhaloalkyl, CF$_3$, OCF$_3$, hydroxy; hydroxyalkyl, keto, thiocarbonyl, carboxy, alkylcarboxy, carboxyalkyl, —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, —S(O)$_2$NR$^b$R$^b$, —NR$^b$S(O)$_2$R$^b$ or —S(O)$_p$R$^c$;
  wherein each substituent is unsubstituted or substituted with 1, 2, or 3 substituents independently selected from alkyl, carboxy, carboxyalkyl, aminocarbonyl, hydroxy, alkoxy, halogen, CF$_3$, amino, substituted amino, cyano or —S(O)$_p$R$^d$;

$R^3$ is selected from a group consisting of hydrogen, alkyl, alkenyl, alkynyl, alkoxyalkyl and arylalkyl;
  wherein alkyl, alkenyl, alkynyl, alkoxyalkyl and arylalkyl are unsubstituted or independently substituted with hydroxyl, alkyl, alkenyl, alkynyl or alkoxy;

X is selected from (C$_3$-C$_{12}$)cycloalkyl or (C$_1$-C$_{10}$)heterocyclyl wherein the heterocycle is connected through a carbon atom to the core ring;

$R^4$ is selected from hydrogen, cyano, hydroxyl, halogen, alkyl, alkenyl, alkynyl, haloalkyl, hydroxyalkyl, alkoxyalkyl, carboxy, carboxyalkyl, alkoxy or haloalkoxy;

A is selected from a bond, (C$_1$-C$_6$)alkyl, (C$_2$-C$_6$)alkenyl or (C$_2$-C$_6$)alkynyl group;
  wherein 1 to 4 methylene groups are optionally replaced by groups independently selected from O, —S(O)$_p$—, —N(R$^a$)—, or —C(O)—;
  wherein A is substituted with B; B is selected from hydrogen, heterocyclyl, cycloalkyl, aryl or heteroaryl;
    wherein heterocyclyl, cycloalkyl, aryl and heteroaryl are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy, —SO3H, aryl, aryloxy, cycloalkyloxy, heteroaryl, aminocarbonylamino, heteroaryloxy, heterocyclyl, heterocyclyloxy, hydroxyamino, alkoxyamino, nitro, S(O)$_2$NR$^b$R$^b$, —NR$^b$S(O)$_2$R$^b$ or —S(O)$_p$R$^c$;
      wherein each substituent is unsubstituted or substituted with 1, 2, or 3 substituents independently selected from alkyl, carboxy, carboxyalkyl, aminocarbonyl, hydroxy, alkoxy, halogen, CF$_3$, amino, substituted amino, cyano or —S(O)$_p$R$^d$;

each R$^a$ is independently selected from the group consisting of hydrogen and alkyl;

each R$^b$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl;

R$^c$ is hydrogen, alkyl, aryl, heteroaryl or heterocyclyl;

R$^d$ is alkyl, aryl, or heteroaryl;

n is 1 or 2; and p is 0, 1 or 2;

with the proviso that— i. if A is bond, B and R$^4$ are each hydrogen, then Z is not a bond; and ii. if Z is a bond, then R$^2$ is not an alkyl, substituted with amino or substituted amino.

According to an embodiment, the present disclosure relates to compounds of formula (I) wherein:

Y is N;

R$^1$ is an alkyl wherein one or more methylene groups is optionally replaced by groups selected from —O—, —S(O)$_p$—, NR$^a$R$^a$, or —C(O) and wherein heteroatom is not adjacent to N in the ring; p is selected from 0, 1 or 2;

wherein alkyl is unsubstituted or substituted with alkoxy, acyl, acylamino, acyloxy, amino, monoalkylamino, dialkylamino, aminocarbonyl, alkoxycarbonylamino, azido, cyano, halogen, haloalkyl, hydroxy, hydroxyalkyl, keto, thiocarbonyl, carboxy, alkylcarboxy, carboxyalkyl, —SO$_3$H, aminocarbonylamino, hydroxyamino, alkoxyamino, or nitro;

Z is selected from —O—, —S(O)$_p$—, —NR$^a$, —NR$^a$C(O)— or —NR$^a$S(O)$_2$—;

R$^2$ is selected from a group consisting of alkyl, haloalkyl, aryl, arylalkyl, hydroxyalkyl, carboxyalkyl, cycloalkyl, cycloalkylalkyl, heterocyclyl, heterocyclylalkyl, heteroaryl and heteroarylalkyl;

wherein alkyl, cycloalkyl, cycloalkylalkyl, arylalkyl, aryl, heteroaryl, heteroarylalkyl, heterocyclyl, and heterocyclylalkyl are unsubstituted or independently substituted with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, haloalkyl, perhaloalkyl, CF$_3$, OCF$_3$, hydroxy, hydroxyalkyl, keto, thiocarbonyl, carboxy, alkylcarboxy, carboxyalkyl, —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, —S(O)$_2$NR$^b$R$^b$, —NR$^b$S(O)$_2$R$^b$ or —S(O)$_p$R$^c$;

R$^3$ is selected from hydrogen or alkyl;

X is a (C$_3$-C$_{12}$)cycloalkyl;

R$^4$ is selected from hydrogen, hydroxyl, halogen, alkyl, haloalkyl, hydroxyalkyl, alkoxyalkyl, carboxy, carboxyalkyl, alkoxy or haloalkoxy;

A is selected from a bond, (C$_1$-C$_6$)alkylene, (C$_2$-C$_6$)alkenylene or (C$_2$-C$_6$)alkynylene group wherein 1 to 4 methylene groups are optionally replaced by groups independently selected from O, —S(O)$_p$, —N(R$^a$)—, or —C(O)—;

wherein A is optionally substituted with B; B is selected from heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO3H, aryl, aryloxy, cycloalkyloxy, heteroaryl, aminocarbonylamino, heteroaryloxy, heterocyclyl, heterocyclyloxy, hydroxyamino, alkoxyamino, nitro, S(O)$_2$NR$^b$R$^b$, —NR$^b$S(O)$_2$R$^b$ and —S(O)$_p$R$^c$;

wherein each substituent is unsubstituted or substituted with 1, 2, or 3 substituents independently selected from alkyl, carboxy, carboxyalkyl, aminocarbonyl, hydroxy, alkoxy, halogen, CF$_3$, amino, substituted amino, cyano or —S(O)$_p$R$^d$;

each R$^a$ is independently selected from the group consisting of hydrogen and alkyl;

each R$^b$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl;

R$^c$ is hydrogen, alkyl, aryl, heteroaryl or heterocyclyl;

R$^d$ is alkyl, aryl, or heteroaryl;

n is 1 or 2; and p is 0, 1 or 2.

According to another embodiment of the present invention, it provides compounds of formula (I) wherein:

Y is N;

R$^1$ is an alkyl wherein one or more methylene groups is optionally replaced by groups selected from —O—, —S(O)$_p$—, NR$^a$R$^a$, or —C(O) and wherein heteroatom is not adjacent to N in the ring; p is selected from 0, 1 or 2;

Z is —O—;

R$^2$ is selected from a group consisting of alkyl, haloalkyl, aryl, arylalkyl, hydroxyalkyl, carboxyalkyl, cycloalkyl, cycloalkylalkyl, heterocyclyl, heterocyclylalkyl, heteroaryl and heteroarylalkyl;

wherein alkyl, cycloalkyl, cycloalkylalkyl, arylalkyl, aryl, heteroaryl, heteroarylalkyl, heterocyclyl, and heterocyclylalkyl are unsubstituted or substituted independently with alkyl, alkoxy, cycloalkyl, acyl, acylamino, acyloxy, amino, monoalkylamino, dialkylamino, aminocarbonyl, alkoxycarbonylamino, cyano, halogen, haloalkyl, perhaloalkyl, CF$_3$; OCF$_3$, hydroxy, hydroxyalkyl, carboxy, alkylcarboxy, carboxyalkyl, —SO$_3$H, aryl, heteroaryl, aminocarbonylamino, heterocyclyl, hydroxyamino, alkoxyamino, nitro, —S(O)$_2$NR$^b$R$^b$, —NR$^b$S(O)$_2$R$^b$ or —S(O)$_p$R$^c$;

R$^3$ is selected from hydrogen or alkyl;

X is a (C$_3$-C$_{12}$)cycloalkyl;

R$^4$ is selected from hydrogen, hydroxyl, halogen, alkyl, haloalkyl, hydroxyalkyl, alkoxyalkyl, carboxy, carboxyalkyl, alkoxy or haloalkoxy;

A is selected from a bond, (C$_1$-C$_6$)alkylene, (C$_2$-C$_6$)alkenylene or (C$_2$-C$_6$)alkynylene group wherein 1 to 4 methylene groups, are optionally replaced by group independently selected from O, —S(O)$_p$—, —N(R$^a$)—, or —C(O)—;

wherein A is optionally substituted with B; B is selected from, heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, S(O)$_2$NR$^b$R$^b$, —NR$^b$S(O)$_2$R$^b$ or —S(O)$_p$R$^c$;

wherein each substituent is unsubstituted or substituted with 1, 2, or 3 substituents independently selected from alkyl, carboxy, carboxyalkyl, aminocarbonyl, hydroxy, alkoxy, halogen, CF$_3$, amino, substituted amino, cyano or —S(O)$_p$R$^d$;

each R$^a$ is independently selected from the group consisting of hydrogen and alkyl;

each R$^b$ is independently selected from the group consisting of hydrogen and alkyl;

R$^c$ is hydrogen, alkyl, aryl, heteroaryl or heterocyclyl;

R$^d$ is alkyl, aryl, or heteroaryl;

n is 1 or 2; and p is 0, 1 or 2.

In another embodiment of the present invention, it provides compounds of formula (I) wherein:

Y is N;

R$^1$ is an alkyl wherein one or more methylene groups is optionally replaced by groups selected from —O—, —S(O)$_p$—, NR$^a$R$^a$, or —C(O) and wherein heteroatom is not adjacent to N in the ring; p is selected from 0, 1 or 2;

wherein alkyl is unsubstituted or substituted with alkoxy, acyl, acylamino, acyloxy, amino, monoalkylamino, dialkylamino, aminocarbonyl, alkoxycarbonylamino, azido, cyano, halogen, haloalkyl, hydroxy, hydroxyalkyl, keto, thiocarbonyl, carboxy, alkylcarboxy, carboxyalkyl, —SO$_3$H, aminocarbonylamino, hydroxyamino, alkoxyamino, or nitro;

Z is selected from —S(O)$_p$—, —NR$^a$, —NR$^a$C(O)— or —NR$^a$S(O)$_2$—; p is selected from 0, 1 or 2;

R$^2$ is selected from a group consisting of alkyl, haloalkyl, aryl, arylalkyl, hydroxyalkyl, carboxyalkyl, cycloalkyl, cycloalkylalkyl, heterocyclyl, heterocyclylalkyl, heteroaryl and heteroarylalkyl;

wherein alkyl, cycloalkyl, cycloalkylalkyl, arylalkyl, aryl, heteroaryl, heteroarylalkyl, heterocyclyl, and heterocyclylalkyl are unsubstituted or substituted independently with alkyl, alkoxy, cycloalkyl, acyl, acylamino, acyloxy, amino, monoalkylamino, dialkylamino, aminocarbonyl, alkoxycarbonylamino, cyano, halogen, haloalkyl, perhaloalkyl, CF$_3$, OCF$_3$, hydroxy, hydroxyalkyl, carboxy, alkylcarboxy, carboxyalkyl, —SO$_3$H, aryl, heteroaryl, aminocarbonylamino, heterocyclyl, hydroxyamino, alkoxyamino, nitro, —S(O)$_2$NR$^b$R$^b$, —NR$^b$S(O)$_2$R$^b$ or —S(O)$_p$R$^c$;

R$^3$ is selected from hydrogen or alkyl;

X is a (C$_3$-C$_{12}$)cycloalkyl;

R$^4$ is selected from hydrogen, hydroxyl, halogen, alkyl, haloalkyl, hydroxyalkyl, alkoxyalkyl, carboxy, carboxyalkyl, alkoxy or haloalkoxy;

A is selected from a bond, (C$_1$-C$_6$)alkylene, (C$_2$-C$_6$)alkenylene or (C$_2$-C$_6$)alkynylene group wherein 1 to 4 methylene groups are optionally replaced by group independently selected from O, —S(O)$_p$—, —N(R$^a$)—, or —C(O)—;

wherein A is optionally substituted with B; B is selected from heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, S(O)$_2$NR$^b$R$^b$, —NR$^b$S(O)$_p$R$^c$;

wherein each substituent is unsubstituted or substituted with 1, 2, or 3 substituents independently selected from alkyl, carboxy, carboxyalkyl, aminocarbonyl, hydroxy, alkoxy, halogen, CF$_3$, amino, substituted amino, cyano or —S(O)$_p$R$^d$;

each R$^a$ is independently selected from the group consisting of hydrogen and alkyl;

each R$^b$ is independently selected from the group consisting of hydrogen and alkyl;

R$^c$ is hydrogen, alkyl, aryl, heteroaryl or heterocyclyl;

R$^d$ is alkyl, aryl, or heteroaryl;

n is 1 or 2; and p is 0, 1 or 2.

According to an embodiment of the present invention, it provides compounds of formula (I) wherein:

Y is N;

R$^1$ is an alkyl;

Z is selected from a bond, —O— or —NR$^a$;

R$^2$ is selected from a group consisting of alkyl, haloalkyl, aryl, arylalkyl, hydroxyalkyl, carboxyalkyl, cycloalkyl, cycloalkylalkyl, heterocyclyl, heterocyclylalkyl, heteroaryl and heteroarylalkyl;

wherein alkyl, cycloalkyl, cycloalkylalkyl, arylalkyl, aryl, heteroaryl, heteroarylalkyl, heterocyclyl, and heterocyclylalkyl are unsubstituted or substituted independently with alkyl, alkoxy, cycloalkyl, acyl, acylamino, acyloxy, amino, monoalkylamino, dialkylamino, aminocarbonyl, alkoxycarbonylamino, cyano, halogen, haloalkyl, perhaloalkyl, CF$_3$, OCF$_3$, hydroxy, hydroxyalkyl, carboxy, alkylcarboxy, carboxyalkyl, —SO$_3$H, aryl, heteroaryl, aminocarbonylamino, heterocyclyl, hydroxyamino, alkoxyamino, nitro, —S(O)$_2$NR$^b$R$^b$, —NR$^b$S(O)$_2$R$^b$ or —S(O)$_p$R$^c$;

R$^3$ is selected from hydrogen or alkyl;

X is selected from:

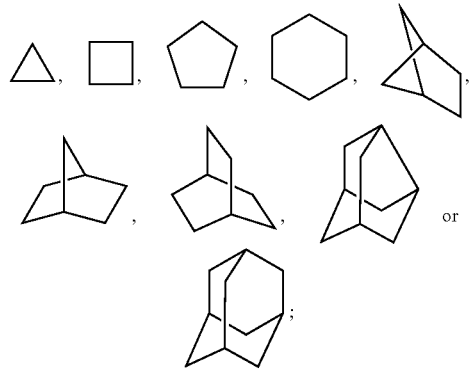

R$^4$ is selected from hydrogen, hydroxyl, halogen, alkyl, haloalkyl, hydroxyalkyl, alkoxyalkyl, carboxy, carboxyalkyl, alkoxy or haloalkoxy;

A is selected from a bond or (C$_1$-C$_6$)alkylene group wherein 1 to 4 methylene groups is optionally replaced by group independently selected from O, —S(O)$_p$—, —N(R$^a$)—, or —C(O)—;

wherein A is optionally substituted with B; B is selected from heterocyclyl, cycloalkyl, aryl or heteroaryl;

wherein heterocyclyl, cycloalkyl, aryl and heteroaryl are unsubstituted or substituted independently with alkyl, alkoxy, acyl, acylamino, acyloxy, amino, monoalkylamino, dialkylamino, aminocarbonyl, alkoxycarbonylamino, cyano, halogen, hydroxy, hydroxyalkyl, carboxy, alkylcarboxy, carboxyalkyl, carboxyalkyloxy, alkylcarboxyalkyloxy —SO$_3$H, aminocarbonylamino, hydroxyamino, alkoxyamino, nitro, S(O)$_2$NR$^b$R$^b$, —NR$^b$S(O)$_2$R$^b$ and —S(O)$_p$R$^c$;

each R$^a$ is independently selected from the group consisting of hydrogen, alkyl;

each R$^b$ is independently selected from the group consisting of hydrogen and alkyl;

R$^c$ is hydrogen, alkyl, aryl, heteroaryl or heterocyclyl;

R$^d$ is alkyl, aryl, or heteroaryl;

n is 1 or 2; and p is 0, 1 or 2.

Particular embodiments of the present invention are the compounds of formula (I) which is:
8-Adamantan-1-yl-2-(2-hydroxy-ethylamino)-1-propyl-1,7-dihydro-purin-6-one,
8-Adamantan-1-yl-2-(2,4-difluoro-benzylamino)-1-propyl-1,7-dihydro-purin-6-one,
8-Cyclopentyl-2-(2-hydroxy-ethylamino)-1-propyl-1,7-dihydro-purin-6-one,
8-Cyclopentyl-2-(2,4-difluoro-benzylamino)-1-propyl-1,7-dihydro-purin-6-one,
8-Cyclopentyl-2-(3,4-difluoro-phenoxy)-1-propy hydro-purin-6-one,
8-Cyclopentyl-2-methoxy-1-propyl-1,7-dihydro-purin-6-one,
8-Cyclopentyl-2-(2-fluoro-phenoxy)-1-propyl-1,7-dihydro-purin-6-one,
8-Adamantan-1-yl-2-(4-fluoro-phenoxy)-1-propyl-1,7-dihydro-purin-6-one,
8-Adamantan-1-yl-2-(3-fluoro-phenoxy)-1-propyl-1,7-dihydro-purin-6-one,
8-Adamantan-1-yl-2-(3,4-difluoro-phenoxy)-1-propyl-1,7-dihydro-purin-6-one,
8-Cyclopentyl-2-ethoxy-1-propyl-1,7-dihydro-purin-6-one,
8-Adamantan-1-yl-2-methylamino-1-propyl-1,7-dihydro-purin-6-one,
8-Adamantan-1-yl-2-dimethylamino-1-propyl-1,7-dihydro-purin-6-one,
(8-Cyclopentyl-6-oxo-1-propyl-6,7-dihydro-1H-purin-2-yloxy)-acetic acid ethyl ester,
(8-Cyclopentyl-6-oxo-1-propyl-6,7-dihydro-1H-purin-2-yloxy)-acetic acid,
8-Bicyclo[2.2.1]hept-2-yl-2-chloro-1-propyl-1,7-dihydro-purin-6-one,
(8-Cyclopentyl-6-oxo-1-propyl-6,7-dihydro-1H-purin-2-ylamino)-acetic acid ethyl ester,
(8-Cyclopentyl-6-oxo-1-propyl-6,7-dihydro-1H-purin-2-ylamino)-acetic acid,
(8-Adamantan-1-yl-6-oxo-1-propyl-6,7-dihydro-1H-purin-2-yloxy)-acetic acid,
8-Cyclopentyl-1-propyl-2-(2-trifluoromethyl-benzylamino)-1,7-dihydro-purin-6-one,
8-Cyclopentyl-1-propyl-2-(4-trifluoromethyl-benzylamino)-1,7-dihydro-purin-6-one,
8-Cyclopentyl-2-(2,6-difluoro-benzylamino)-1-propyl-1,7-dihydro-Aurin-6-one,
8-Cyclopentyl-2-(2-methoxy-benzylamino)-1-propyl-1,7-dihydro-purin-6-one,
8-Cyclopentyl-1-propyl-2-(2-trifluoromethoxy-benzylamino)-1,7-dihydro-purin-6-one,
8-Cyclopentyl-2-(4-fluoro-benzylamino)-1-propyl-1,7-dihydro-purin-6-one,
8-Cyclopentyl-2-phenethylamino-1-propyl-1,7-dihydro-purin-6-one,
8-Cyclopentyl-2-(4-methyl-benzylamino)-1-propyl-1,7-dihydro-purin-6-one,
8-Cyclopentyl-1-propyl-2-[(thiophen-2-ylmethyl)-amino]-1,7-dihydro-purin-6-one,
4-[(8-Cyclopentyl-6-oxo-1-propyl-6,7-dihydro-1H-purin-2-ylamino)-methyl]-benzoic acid methyl ester,
4-[(8-Cyclopentyl-6-oxo-1-propyl-6,7-dihydro-1H-purin-2-ylamino)-methyl]-benzoic acid,
8-Cyclohexyl-2-cyclopentyloxy-1-propyl-1,7-dihydro-purin-6-one,
8-Cyclopentyl-2-phenylamino-1-propyl-1,7-dihydro-purin-6-one,
8-Cyclopentyl-2-(4-fluoro-phenylamino)-1-propyl-1,7-dihydro-purin-6-one,
2-(3-Chloro-benzylamino)-8-cyclopentyl-1-propyl-1,7-dihydro-purin-6-one,
8-Cyclopentyl-2-cyclopentyloxy-1-propyl-1,7-dihydro-purin-6-one,
8-Cyclopentyl-2-(3-fluoro-phenoxy)-1-propyl-1,7-dihydro-purin-6-one,
8-Cyclopentyl-2-(3-methoxy-phenoxy)-1-propyl-1,7-dihydro-purin-6-one,
8-Cyclohexyl-2-(3-fluoro-phenoxy)-1-propyl-1,7-dihydro-purin-6-one,
2-(3-Fluoro-phenoxy)-8-(hexahydro-2,5-methano-pentalen-3a-yl)-1-propyl-1,7-dihydro-purin-6-one,
2-(3,4-Difluoro-phenoxy)-8-(hexahydro-2,5-methano-pentalen-3a-yl)-1-propyl-1,7-dihydro-purin-6-one,
8-(Hexahydro-2,5-methano-pentalen-3a-yl)-2-(4-methyl-benzylamino)-1-propyl-1,7-dihydro-purin-6-one,
8-(Hexahydro-2,5-methano-pentalen-3a-yl)-1-propyl-2-(4-trifluoromethyl-benzylamino)-1,7-dihydro-purin-6-one,
2-Cyclopentyloxy-8-(hexahydro-2,5-methano-pentalen-3a-yl)-1-propyl-1,7-dihydro-purin-6-one,
8-Cyclohexyl-2-(4-fluoro-benzylamino)-1-propyl-1,7-dihydro-purin-6-one,
2-(8-Cyclohexyl-6-oxo-1-propyl-6,7-dihydro-1H-purin-2-ylamino)-3-(3-fluoro-phenyl)-propionic acid,
4-[8-(Hexahydro-2,5-methano-pentalen-3a-yl)-6-oxo-1-propyl-6,7-dihydro-1H-purin-2-yloxy]-benzoic acid,
3-[8-(Hexahydro-2,5-methano-pentalen-3a-yl)-6-oxo-1-propyl-6,7-dihydro-1H-purin-2-yloxy]-benzoic acid,
{4-[8-(Hexahydro-2,5-methano-pentalen-3a-yl)-6-oxo-1-propyl-6,7-dihydro-1H-purin-2-yloxy]-phenyl}-acetic acid,
8-Cyclohexyl-1-propyl-2-(pyridin-3-yloxy)-1,7-dihydro-purin-6-one,
2-Cyclopentyloxy-8-cyclopropyl-1-propyl-1,7-dihydro-purin-6-one,
8-Cyclohexyl-2-(4-fluoro-phenoxy)-1-propyl-1,7-dihydro-purin-6-one,
8-Cyclohexyl-2-(3-methoxy-phenoxy)-1-propyl-1,7-dihydro-purin-6-one,
4-(8-Cyclohexyl-6-oxo-1-propyl-6,7-dihydro-1H-purin-2-yloxy)-benzoic acid,
8-Cyclohexyl-1-propyl-2-m-tolyloxy-1,7-dihydro-purin-6-one,
N-[4-(8-Cyclohexyl-6-oxo-1-propyl-6,7-dihydro-1H-purin-2-yloxy)-phenyl]-acetamide,
2-Cyclohexyl-5-[4-(1-hydroxy-ethyl)-phenoxy]-6-propyl-1,6-dihydro-imidazo[4,5-b]pyridin-7-one,
8-Cyclohexyl-2-(2,4-dichloro-phenoxy)-1-propyl-1,7-dihydro-purin-6-one,
8-Cyclohexyl-2-(4-fluoro-2-methoxy-phenoxy)-1-propyl-1,7-dihydro-purin-6-one,
2-(2-Chloro-4-fluoro-phenoxy)-8-cyclohexyl-1-propyl-1,7-dihydro-purin-6-one,
8-Cyclohexyl-2-(3,4-dimethyl-phenoxy)-1-propyl-1,7-dihydro-purin-6-one,
8-Cyclopentyl-1-propyl-2-(3-trifluoromethyl-phenoxy)-1,7-dihydro-purin-6-one,
8-Cyclopentyl-2-(4-fluoro-2-methoxy-phenoxy)-1-propyl-1,7-dihydro-purin-6-one,
4-[2-(3-Methoxy-phenoxy)-6-oxo-1-propyl-6,7-dihydro-1H-purin-8-yl]-bicyclo[2.2.2]octane-1-carboxylic acid,
8-Cyclopentyl-2-(2,4-dichloro-phenoxy)-1-propyl-1,7-dihydro-purin-6-one,
2-(4-Chloro-2-methoxy-phenoxy)-8-cyclopentyl-1-propyl-1,7-dihydro-purin-6-one,
2-(2-Chloro-4-fluoro-phenoxy)-8-cyclopentyl-1-propyl-1,7-dihydro-purin-6-one, 8-Cyclopentyl-2-(3,4-dimethyl-phenoxy)-1-propyl-1,7-dihydro-purin-6-one,
4-(8-Cyclopentyl-6-oxo-1-propyl-6,7-dihydro-1H-purin-2-yloxy)-benzamide,
8-Cyclopentyl-2-(6-methyl-pyridin-3-yloxy)-1-propyl-1,7-dihydro-purin-6-one,
2-(5-Chloro-pyridin-3-yloxy)-8-cyclopentyl-1-propyl-1,7-dihydro-purin-6-one,
8-Cyclopentyl-2-(1H-indol-5-yloxy)-1-propyl-1,7-dihydro-purin-6-one,
8-Cyclopentyl-2-(4-fluoro-3-trifluoromethyl-phenoxy)-1-propyl-1,7-dihydro-purin-6-one,
8-Cyclohexyl-1-propyl-2-(3-trifluoromethyl-phenoxy)-1,7-dihydro-purin-6-one,
2-(Benzo[1,3]dioxol-5-yloxy)-8-cyclohexyl-1-propyl-1,7-dihydro-purin-6-one,
4-(8-Cyclohexyl-6-oxo-1-propyl-6,7-dihydro-1H-purin-2-yloxy)-benzenesulfonamide,
8-Cyclohexyl-1-propyl-2-[(S)-(tetrahydro-furan-3-yl)oxy]-1,7-dihydro-purin-6-one,
2-(3-Acetyl-phenoxy)-8-cyclohexyl-1-propyl-1,7-dihydro-purin-6-one,
8-Cyclohexyl-2-[3-(1-hydroxy-ethyl)-phenoxy]-1-propyl-1,7-dihydro-purin-6-one,
6-Cyclohexyl-2-((R)-3-methyl-tetrahydro-furan-3-yloxy)-3-propyl-3,5-dihydro-pyrrolo[3,2-d]pyrimidin-4-one,
8-Cyclopentyl-2-(5-methyl-pyridin-2-yloxy)-1-propyl-1,7-dihydro-purin-6-one,
[3-(8-Cyclopentyl-6-oxo-1-propyl-6,7-dihydro-1H-purin-2-yloxy)-phenyl]-acetic acid,
[4-(8-Cyclopentyl-6-oxo-1-propyl-6,7-dihydro-1H-purin-2-yloxy)-3-fluoro-phenyl]-acetic acid,
8-Cyclopentyl-2-(6-methyl-pyridin-2-yloxy)-1-propyl-1,7-dihydro-purin-6-one,
8-Cyclopentyl-2-(4-fluoro-3-methyl-phenoxy)-1-propyl-1,7-dihydro-purin-6-one,
2-(Benzo[1,3]dioxol-5-yloxy)-8-cyclopentyl-1-propyl-1,7-dihydro-purin-6-one,
8-Cyclopentyl-2-(4-fluoro-2-trifluoromethyl-phenoxy)-1-propyl-1,7-dihydro-purin-6-one,
8-Cyclopentyl-1-propyl-2-(3-trifluoromethoxy-phenoxy)-1,7-dihydro-purin-6-one,
4-[2-(3-Fluoro-phenoxy)-6-oxo-1-propyl-6,7-dihydro-1H-purin-8-yl]-bicyclo[2.2.2]octane-1-carboxylic acid,
4-(8-Cyclopentyl-6-oxo-1-propyl-6,7-dihydro-1H-purin-2-yloxy)-benzenesulfonamide,
8-Cyclopentyl-2-(1-methyl-pyrrolidin-3-yloxy)-1-propyl-7-dihydro-purin-6-one,
8-Cyclopentyl-2-(1-methyl-piperidin-4-yloxy)-1-propyl-1,7-dihydro-purin-6-one,
8-Cyclopentyl-1-propyl-2-(tetrahydro-furan-3-yloxy)-1,7-dihydro-purin-6-one,
8-Cyclopentyl-1-propyl-2-(tetrahydro-pyran-4-yloxy)-1,7-dihydro-purin-6-one,
8-Cyclopentyl-2-(3-hydroxy-phenoxy)-1-propyl-1,7-dihydro-purin-6-one,
8-(3,4-Dihydroxy-cyclopentyl)-2-(3-methoxy-phenoxy)-1-propyl-1,7-dihydro-purin-6-one,
8-Cyclopentyl-1-propyl-2-(3-trifluoromethyl-henylamino)-1,7-dihydro-purin-6-one,
8-Cyclopentyl-2-(3-fluoro-phenylamino)-1-propyl-1,7-dihydro-purin-6-one,
3-(8-Cyclopentyl-6-oxo-1-propyl-6,7-dihydro-1H-purin-2-yloxy)-benzoic acid methyl ester,
2-(3-Acetyl-phenoxy)-8-cyclopentyl-1-propyl-1,7-dihydro-purin-6-one,
8-Cyclopentyl-2-[3-(1-hydroxy-ethyl)-phenoxy]-1-propyl-1,7-dihydro-purin-6-one,
8-Cyclopentyl-2-[3-(1-hydroxy-1-methyl-ethyl)-phenoxy]-1-propyl-1,7-dihydro-purin-6-one,
3-(8-Cyclopentyl-6-oxo-1-propyl-6,7-dihydro-1H-purin-2-yloxy)-benzoic acid,
3-(8-Cyclopentyl-6-oxo-1-propyl-6,7-dihydro-1H-purin-2-yloxy)-benzamide,
8-Cyclopentyl-1-propyl-2-(6-trifluoromethyl-pyridin-2-yloxy)-1,7-dihydro-purin-6-one,
8-Cyclopentyl-1-propyl-2-(5-trifluoromethyl-pyridin-2-yloxy)-1,7-dihydro-purin-6-one,
8-Cyclopentyl-2-(2-methyl-pyridin-3-yloxy)-1-propyl-1,7-dihydro-purin-6-one,
3-(8-Cyclopentyl-6-oxo-1-propyl-6,7-dihydro-1H-purin-2-yloxy)-benzonitrile,
8-Cyclopentyl-2-(1H-indol-7-yloxy)-1-propyl-1,7-dihydro-purin-6-one,
8-Cyclopentyl-2-(1H-indol-4-yloxy)-1-propyl-1,7-dihydro-purin-6-one,
8-Cyclopentyl-2-(3-hydroxy-cyclopentyloxy)-1-propyl-1,7-dihydro-purin-6-one,
8-Cyclopentyl-1-propyl-2-[(S)-(tetrahydro-furan-3-yl)oxy]-1,7-dihydro-purin-6-one,
8-Cyclopentyl-1-propyl-2-[(R)-(tetrahydro-furan-3-yl)oxy]-1,7-dihydro-purin-6-one,
2-(6-Chloro-pyridin-2-yloxy)-8-cyclopentyl-1-propyl-1,7-dihydro-purin-6-one,
2-Chloro-8-cyclopentyl-1-isobutyl-1,7-dihydro-purin-6-one,
8-[4-(5-Chloro-pyridin-2-yloxymethyl)-bicyclo[2.2.2]oct-1-yl]-2-(3,4-difluoro-phenoxy)-1-propyl-1,7-dihydro-purin-6-one,
2-Cyclopentyloxy-1-propyl-8-[4-(pyridin-2-yloxymethyl)-bicyclo[2.2.2]oct-1-yl]-1,7-dihydro-purin-6-one,
8-[4-(5-Chloro-pyridin-2-yloxymethyl)-bicyclo[2.2.2]oct-1-yl]-2-(2-methyl-pyridin-3-yloxy)-1-propyl-1,7-dihydro-purin-6-one,
8-Cyclopentyl-2-(4-methyl-pyridin-2-yloxy)-1-propyl-1,7-dihydro-purin-6-one,
8-Cyclopentyl-2-(2-methyl-1-oxy-pyridin-3-yloxy)-1-propyl-1,7-dihydro-purin-6-one,
8-Cyclopentyl-2-(2-oxo-1,2-dihydro-pyridin-4-yloxy)-1-propyl-1,7-dihydro-purin-6-one,
8-Cyclopentyl-2-(2-oxo-1,2-dihydro-pyridin-3-yloxy)-1-propyl-1,7-dihydro-purin-6-one,
2-(2-Chloro-pyridin-3-yloxy)-8-cyclopentyl-1-propyl-1,7-dihydro-purin-6-one,
8-Cyclopentyl-1-propyl-2-o-tolyloxy-1,7-dihydro-purin-6-one,
8-Cyclopentyl-1-isobutyl-2-(2-methyl-pyridin-3-yloxy)-1,7-dihydro-purin-6-one,
8-Cyclopentyl-2-(4-fluoro-2-isoxazol-5-yl-phenoxy)-1-propyl-1,7-dihydro-purin-6-one,
2-(8-Chloro-quinolin-2-yloxy)-8-cyclopentyl-1-propyl-1,7-dihydro-purin-6-one,
8-Cyclopentyl-2-[4-fluoro-2-(1H-pyrazol-3-yl)-phenoxy]-1-propyl-1,7-dihydro-purin-6-one,
8-Cyclopentyl-2-[4-fluoro-2-(2H-pyrazol-3-yl)-phenoxy]-1-propyl-1,7-dihydro-purin-6-one,
8-Cyclopentyl-2-(2,6-dimethyl-pyridin-3-yloxy)-1-propyl-1,7-dihydro-purin-6-one,
2-Benzyloxy-8-cyclopentyl-1-propyl-1,7-dihydro-purin-6-one,
8-Cyclopentyl-2-(3,5-difluoro-benzyloxy)-1-propyl-1,7-dihydro-purin-6-one, 8-Cyclopentyl-1-propyl-2-(pyridin-3-ylmethoxy)-1,7-dihydro-purin-6-one,
2-But-2-ynyloxy-8-cyclopentyl-1-propyl-1,7-dihydro-purin-6-one,
8-Cyclopentyl-1-propyl-2-(pyrimidin-2-yloxy)-1,7-dihydro-purin-6-one,
8-Cyclopentyl-1-propyl-2-(pyridin-2-ylsulfanyl)-1,7-dihydro-purin-6-one,
8-Cyclopentyl-2-(1H-imidazol-2-ylsulfanyl)-1-propyl-1,7-dihydro-purin-6-one,
8-Cyclopentyl-2-ethanesulfonyl-1-propyl-1,7-dihydro-purin-6-one,
8-Cyclopentyl-2-ethylsulfanyl-1-propyl-1,7-dihydro-purin-6-one,
2-Cyclohexylsulfanyl-8-cyclopentyl-1-propyl-1,7-dihydro-purin-6-one,
(8-Cyclopentyl-6-oxo-1-propyl-6,7-dihydro-1H-purin-2-ylsulfanyl)-acetic acid ethyl ester,
8-Cyclopentyl-1-propyl-2-(pyrimidin-2-ylamino)-1,7-dihydro-purin-6-one,
3-(8-Cyclopentyl-6-oxo-1-propyl-6,7-dihydro-1H-purin-2-yloxy)-pyridine-2-carboxylic acid amide,
2-Benzyloxy-8-cyclohexyl-1-propyl-1,7-dihydro-purin-6-one,
8-Cyclohexyl-1-propyl-2-(3-trifluoromethyl-benzyloxy)-1,7-dihydro-purine-6-one,
8-Cyclohexyl-1-propyl-2-(pyridin-4-ylmethoxy)-1,7-dihydro-purin-6-one,
8-Cyclohexyl-1-propyl-2-(thiazol-2-ylsulfanyl)-1,7-dihydro-purin-6-one,
(8-Cyclohexyl-6-oxo-1-propyl-6,7-dihydro-1H-purin-2-ylsulfanyl)-acetic acid,
8-Cyclohexyl-1-propyl-2-(pyridin-3-ylamino)-1,7-dihydro-purin-6-one,
8-Adamantan-1-yl-2-benzyloxy-1-propyl-1,7-dihydro-purin-6-one,
8-Adamantan-1-yl-2-(3-methoxy-benzyloxy)-1-propyl-1,7-dihydro-purin-6-one,
8-Adamantan-1-yl-1-propyl-2-(pyridin-3-ylsulfanyl)-1,7-dihydro-purin-6-one,
8-Adamantan-1-yl-1-propyl-2-(pyridin-4-ylamino)-1,7-dihydro-purin-6-one,
3-[8-(Hexahydro-2,5-methano-pentalen-2-yl)-6-oxo-1-propyl-6,7-dihydro-1H-purin-2-yloxymethyl]-benzoic acid ethyl ester,
3-[8-(Hexahydro-2,5-methano-pentalen-2-yl)-6-oxo-1-propyl-6,7-dihydro-1H-purin-2-yloxy]-pyridine-2-carboxylic acid,
3-[8-(Hexahydro-2,5-methano-pentalen-3a-yl)-6-oxo-1-propyl-6,7-dihydro-1H-purin-2-yloxymethyl]-benzoic acid ethyl ester,
3-[8-(Hexahydro-2,5-methano-pentalen-3a-yl)-6-oxo-1-propyl-6,7-dihydro-1H-purin-2-yloxy]-pyridine-2-carboxylic acid,
8-Bicyclo[2.2.1]hept-2-yl-2-ethylsulfanyl-1-propyl-1,7-dihydro-purin-6-one,
8-Bicyclo[2.2.1]hept-2-yl-2-(3-chloro-benzyloxy)-1-propyl-1,7-dihydro-purin-6-one,
8-Bicyclo[2.2.1]hept-2-yl-2-cyclohexylsulfanyl-1-propyl-1,7-dihydro-purin-6-one,
8-(Hexahydro-2,5-methano-pentalen-3a-yl)-2-(1H-imidazol-2-yloxy)-1-propyl-1,7-dihydro-purin-6-one,
8-Bicyclo[2.2.1]hept-2-yl-1-propyl-2-(pyrimidin-2-yloxy)-1,7-dihydro-purin-6-one,
8-Bicyclo[2.2.1]hept-2-yl-1-propyl-2-([1,3,4]thiadiazol-2-yloxy)-1,7-dihydro-purin-6-one,
2-(4-Methyl-benzyloxy)-8-piperidin-4-yl-1-propyl-1,7-dihydro-purin-6-one,
2-Cyclopentylsulfanyl-8-piperidin-4-yl-1-propyl-1,7-dihydro-purin-6-one,
2-(2-Hydroxy-ethylsulfanyl)-8-piperidin-4-yl-1-propyl-1,7-dihydro-purin-6-one,
8-Piperidin-4-yl-1-propyl-2-(thiazol-2-yloxy)-1,7-dihydro-purin-6-one,
8-Piperidin-4-yl-1-propyl-2-(pyrimidin-2-ylamino)-1,7-dihydro-purin-6-one,
2-(6-Methoxy-pyridin-3-yloxy)-8-piperidin-4-yl-1-propyl-1,7-dihydro-purin-6-one,
8-(1-Methyl-piperidin-4-yl)-1-propyl-2-(pyridin-4-ylamino)-1,7-dihydro-purin-6-one,
8-(1-Methyl-piperidin-4-yl)-1-propyl-2-(pyridin-4-yloxy)-1,7-dihydro-purin-6-one,
2-(3-Methyl-benzyloxy)-8-(1-methyl-piperidin-4-yl)-1-propyl-1,7-dihydro-purin-6-one,
8-(1-Methyl-piperidin-4-yl)-1-propyl-2-(pyridin-4-ylsulfanyl)-1,7-dihydro-purin-6-one,
3-(6-Oxo-2-phenoxy-1-propyl-6,7-dihydro-1H-purin-8-yl)-cyclopentane carboxylic acid,
3-(6-Oxo-2-phenylamino-1-propyl-6,7-dihydro-1H-purin-8-yl)-cyclopentane carboxylic acid,
3-(2-Benzyloxy-6-oxo-1-propyl-6,7-dihydro-1H-purin-8-yl)-cyclopentane carboxylic acid,
3-(2-Cyclopentylsulfanyl-6-oxo-1-propyl-6,7-dihydro-1H-purin-8-yl)-cyclopentane carboxylic acid,
3-(2-Benzylamino-6-oxo-1-propyl-6,7-dihydro-1H-purin-8-yl)-cyclopentane carboxylic acid,
8-(3-Hydroxymethyl-cyclopentyl)-2-phenoxy-1-propyl-1,7-dihydro-purin-6-one,
8-(3-Hydroxymethyl-cyclopentyl)-2-phenylamine-1-propyl-1,7-dihydro-purin-6-one,
4-(6-Oxo-2-phenylamino-1-propyl-6,7-dihydro-1H-purin-8-yl)-cyclohexane carboxylic acid,
4-(6-Oxo-2-phenoxy-1-propyl-6,7-dihydro-1H-purin-8-yl)-cyclohexane carboxylic acid,
[4-(2-Benzyloxy-6-oxo-1-propyl-6,7-dihydro-1H-purin-8-yl)-cyclohexyl]-acetic acid,
2-Benzyloxy-8-cyclopentyl-1-(2-hydroxy-ethyl)-1,7-dihydro-purin-6-one,
3-(8-Cyclopentyl-6-oxo-2-phenoxy-6,7-dihydro-purin-1-yl)-propionic acid,
3-(8-Cyclohexyl-6-oxo-2-phenoxy-6,7-dihydro-purin-1-yl)-propionic acid,
3-(8-Adamantan-1-yl-6-oxo-2-phenoxy-6,7-dihydro-purin-1-yl)-propionic acid,
3-[8-(Hexahydro-2,5-methano-pentalen-3a-yl)-6-oxo-2-phenoxy-6,7-dihydro-purin-1-yl]-propionic acid,
3-(8-Bicyclo[2.2.1]hept-2-yl-6-oxo-2-phenoxy-6,7-dihydro-purin-1-yl)-propionic acid,
3-(4-[2-(3-Methoxy-phenoxy)-6-oxo-1-propyl-6,7-dihydro-1H-purin-8-yl]-bicyclo[2.2.2]oct-1-yl)-propionic acid,
3-[4-(2-Cyclopentyloxy-6-oxo-1-propyl-6,7-dihydro-1H-purin-8-yl)-bicyclo[2.2.2]oct-1-yl]-propionic acid,
3-[4-(2-Cyclopentyloxy-6-oxo-1-propyl-6,7-dihydro-1H-purin-8-yl)-bicyclo[2.2.2]oct-1-yl]-propionamide,
2-(3-Fluoro-phenoxy)-1-propyl-8-[4-(thiazol-2-yloxymethyl)-bicyclo[2.2.2]oct-1-yl]-1,7-dihydro-purin-6-one,
2-{4-[2-(3-Methoxy-phenoxy)-6-oxo-1-propyl-6,7-dihydro-1H-purin-8-yl]-bicyclo[2.2.2]oct-1-ylmethoxy}-thiazole-4-carboxylic acid,
2-(4-Fluoro-benzylamino)-1-propyl-8-[4-(thiazol-2-yloxymethyl)-bicyclo[2.2.2]oct-1-yl]-1,7-dihydro-purin-6-one, 2-{4-[2-(4-Fluoro-benzylamino)-6-oxo-1-propyl-6,7-dihydro-1H-purin-8-yl]bicyclo[2.2.2]oct-1-ylmethoxy}-thiazole-5-carboxylic acid,
2-{4-[2-(3-Fluoro-phenylamino)-6-oxo-1-propyl-6,7-dihydro-1H-purin-8-yl]-bicyclo[2.2.2]oct-1-ylmethoxy}-thiazole-5-carboxylic acid,
2-[4-(2-Cyclopentyloxy-6-oxo-1-propyl-6,7-dihydro-1H-purin-8-yl)-bicyclo[2.2.2]oct-1-ylmethoxy]-thiazole-5-carboxylic acid,
1-Propyl-2-(tetrahydro-furan-3-yloxy)-8-[4-(thiazol-2-yloxymethyl)-bicyclo[2.2.2]oct-1-yl]-1,7-dihydro-purin-6-one,
2-Benzyl-1-propyl-8-[4-(thiazol-2-yloxymethyl)-bicyclo[2.2.2]oct-1-yl]-1,7-dihydro-purin-6-one,
{6-Oxo-1-propyl-8-[4-(thiazol-2-yloxymethyl)-bicyclo[2.2.2]oct-1-yl]-6,7-dihydro-1H-purin-2-ylamino}-acetic acid,
{6-Oxo-1-propyl-8-[4-(pyridin-2-yloxymethyl)-bicyclo[2.2.2]oct-1-yl]-6,7-dihydro-1H-purin-2-yloxy}-aceticacid,
1-Propyl-8-[4-(pyridin-2-yloxymethyl)-bicyclo[2.2.2]oct-1-yl]-2-(3-trifluoromethyl-phenoxy)-1,7-dihydro-purin-6-one,
2-(3-Chloro-phenylamino)-1-propyl-8-[4-(pyridin-2-yloxymethyl)-bicyclo[2.2.2]oct-1-yl]-1,7-dihydro-purin-6-one,
2-(4-Methyl-benzylamino)-1-propyl-8-[4-(pyridin-2-yloxymethyl)-bicyclo[2.2.2]oct-1-yl]-1,7-dihydro-purin-6-one,
6-{4-[2-(4-Fluoro-benzylamino)-6-oxo-1-propyl-6,7-dihydro-1H-purin-8-yl]-bicyclo[2.2.2]oct-1-ylmethoxy}-nicotinic acid,
6-{4-[6-Oxo-1-propyl-2-(tetrahydro-pyran-4-yloxy)-6,7-dihydro-1H-purin-8-yl]bicyclo[2.2.2]oct-1-ylmethoxy}-nicotinic acid,
2-Ethyl-1-propyl-8-[4-(4-trifluoromethyl-pyridin-2-yloxymethyl)-bicyclo[2.2.2]oct-1-yl]-1,7-dihydro-purin-6-one,
2-Ethyl-1-propyl-8-[4-(pyrimidin-2-yloxymethyl)-bicyclo[2.2.2]oct-1-yl]-1,7-dihydro-purin-6-one,
8-[4-(5-Chloro-pyrimidin-2-yloxymethyl)-bicyclo[2.2.2]oct-1-yl]-2-(3-fluoro-phenoxy)-1-propyl-1,7-dihydro-purin-6-one,
8-[4-(5-Chloro-pyrimidin-2-ylmethoxy)-bicyclo[2.2.2]oct-1-yl]-2-(3-fluoro-phenoxy)-1-propyl-1,7-dihydro-purin-6-one,
8-[4-(4-Fluoro-pyridin-2-ylmethoxy)-bicyclo[2.2.2]oct-1-yl]-1-propyl-2-m-tolyloxy-1,7-dihydro-purin-6-one,
6-[4-(6-Oxo-1-propyl-2-p-tolylamino-6,7-dihydro-1H-purin-8-yl)-bicyclo[2.2.2]oct-1-yloxymethyl]-nicotinic acid,
6-{4-[2-(4-Fluoro-phenoxy)-6-oxo-1-propyl-6,7-dihydro-1H-purin-8-yl]-bicyclo[2.2.2]oct-1-ylamino}-nicotinic acid,
2-Cyclopentyloxy-8-[4-(5-fluoro-pyridin-2-ylamino)-bicyclo[2.2.2]oct-1-yl]-1-propyl-1,7-dihydro-purin-6-one,
2-Cyclopentyloxy-1-propyl-8-[4-(thiazol-2-ylamino)-bicyclo[2.2.2]oct-1-yl]-1,7-dihydro-purin-6-one,
1-Propyl-8-[4-(thiazol-2-yloxy)-bicyclo[2.2.2]oct-1-yl]-2-m-tolyloxy-1,7-dihydro-purin-6-one,
1-Propyl-8-[3-(thiazol-2-yloxy)-adamantan-1-yl]-2-m-tolyloxy-1,7-dihydro-purin-6-one,
2-{3-[2-(3-Fluoro-phenylamino)-6-oxo-1-propyl-6,7-dihydro-1H-purin-8-yl]-adamantan-1-yloxy}-thiazole-5-carboxylic acid,
2-{3-[2-(3-Fluoro-phenoxy)-6-oxo-1-propyl-6,7-dihydro-1H-purin-8-yl]-adamantan-1-ylamino}-thiazole-4-carboxylic acid,
2-{3-[2-(3-Fluoro-phenoxy)-6-oxo-1-propyl-6,7-dihydro-1H-purin-8-yl]-adamantan-1-yloxymethyl}-thiazole-4-carboxylic acid,
2-Cyclohexyloxy-1-propyl-8-[3-(thiazol-2-ylmethoxy)-adamantan-1-yl]-1,7-dihydro-purin-6-one,
8-[3-(5-Fluoro-pyridin-2-yloxymethyl)-adamantan-1-yl]-2-methoxy-1-propyl-1,7-dihydro-purin-6-one,
2-(3-Fluoro-benzylamino)-8-[3-(5-fluoro-pyridin-2-yloxymethyl)-adamantan-1-yl]-1-propyl-1,7-dihydro-purin-6-one,
8-{3-[(5-Fluoro-pyridin-2-ylamino)-methyl]-adamantan-1-yl}-1-propyl-2-p-tolyloxy-1,7-dihydro-purin-6-one,
2-Benzyl-1-propyl-8-[3-(thiazol-2-ylaminomethyl)-adamantan-1-yl]-1,7-dihydro-purin-6-one,
2-(3-Fluoro-phenoxy)-1-propyl-8-[3-(3-trifluoromethyl-phenoxymethyl)-adamantan-1-yl]-1,7-dihydro-purin-6-one,
3-{3-[6-Oxo-1-propyl-2-(tetrahydro-furan-3-yloxy)-6,7-dihydro-1H-purin-8-yl]-adamantan-1-yloxymethyl}-benzoic acid,
8-[3-(3-Fluoro-benzylamino)-adamantan-1-yl]-2-methoxy-1-propyl-1,7-dihydro-purin-6-one,
2-Ethyl-8-{3-[(5-fluoro-pyridin-3-ylmethyl)-amino]-adamantan-1-yl}-1-propyl-1,7-dihydro-purin-6-one,
1-Propyl-8-{3-[(pyrimidin-5-ylmethyl)-amino]-adamantan-1-yl}-2-m-tolyloxy-1,7-dihydro-purin-6-one,
2-(4-Chloro-phenoxy)-1-propyl-8-{3-[(thiazol-2-ylmethyl)-amino]-adamantan-1-yl}-1,7-dihydro-purin-6-one,
1-Propyl-2-(pyridin-2-yloxy)-8-{3-[(thiazol-2-ylmethyl)-amino]-adamantan-1-yl}-1,7-dihydro-purin-6-one and
2-(6-Methyl-pyridin-2-yloxy)-1-propyl-8-[3-(thiazol-2-ylmethoxy)-adamantan-1-yl]-1,7-dihydro-purin-6-one.

In an embodiment of the present invention it provides a compound of formula (I) or its tautomers, polymorphs, stereoisomers, prodrugs, solvate or pharmaceutically acceptable salts thereof, for treating disease or disorder susceptible to improvement by antagonism of $A_1$ receptor.

Further embodiment of the present invention provides a compound of formula (I), or its tautomers, polymorphs, stereoisomers, prodrugs, solvate or pharmaceutically acceptable salts thereof, for treating disease or disorder susceptible to improvement by antagonism of $A_{2A}$ receptor.

Another embodiment of the present invention provides a compound of formula (I) or its tautomers, polymorphs, stereoisomers, prodrugs, solvate or pharmaceutically acceptable salts thereof, for treating disease or disorder susceptible to improvement by antagonism of $A_{2B}$ receptor.

Another embodiment of the present invention provides a compound of formula (I) or its tautomers, polymorphs, stereoisomers, prodrugs, solvate or a pharmaceutically acceptable salts thereof, which are adenosine $A_1$ and $A_{2A}$ antagonist, or adenosine $A_1$ and $A_{2B}$ antagonist, or $A_1$, $A_2A$ and $A_{2B}$ antagonist thereby providing dual or pan antagonistic activity through additive or/and synergistic effect.

Further embodiment of the present invention provides a compound of formula (I), or its tautomers, polymorphs, stereoisomers, prodrugs, solvate or a pharmaceutically acceptable salts thereof, for treating asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, autoimmune diseases.

Another embodiment of the present invention provides a compound of formula (I) for use in treatment of conditions mediated by adenosine receptor.

Yet another embodiment of the present invention provides a pharmaceutical composition comprising, as an active ingredient, at least one compound of formula (I), or its tautomers, polymorphs, stereoisomers, prodrugs, solvate or a pharmaceutically acceptable salts thereof, together with one or more pharmaceutically acceptable carriers or excipients.

Further another embodiment of the present invention provides a pharmaceutical composition comprising, a compound of formula I or its tautomers, polymorphs, stereoisomers, prodrugs, solvate or a pharmaceutically acceptable salts thereof, in combination with one or more second therapeutically active agents. The second therapeutically active agent is selected from anti-inflammatory agent, anti-diabetic agent, anti-hypertensive agent or anti-dyslipidemic agent.

Another embodiment of the present invention provides a pharmaceutical composition, wherein the second therapeutically active agent is selected from anticholinergic agent, anti-muscarinic agent, steroid, LTB4 (leukotriene B4) antagonist, dopamine receptor agonists, phosphodiesterase 4 inhibitor, beta-2 adrenergic receptor agonist, insulin, insulin derivatives and mimetics, insulin secretagogues, insulinotropic sulfonylurea receptor ligands, thiazolidone derivatives, glycogen synthase kinase-3 inhibitor, sodium-dependent glucose co-transporter inhibitor, glycogen phosphorylase A inhibitor, biguanide, alpha-glucosidase inhibitor, glucagon like peptide-1 (GLP-I), GLP-1 analogs and GLP-I mimetics, modulators of peroxisome proliferator-activated receptors, dipeptidyl peptidase IV inhibitor, stearoyl-CoA desaturase-1 inhibitor, diacylglycerol acyltransferase 1 and 2 inhibitor, acetyl CoA carboxylase 2 inhibitor, and breakers of advanced glycation end products, loop diuretics, angiotensin converting enzyme inhibitor, inhibitor of the Na—K-ATPase membrane pump such as digoxin, neutralendopeptidase (NEP) inhibitor, ACE/NEP inhibitors, angiotensin II antagonists, renin inhibitors, β-adrenergic receptor blockers, inotropic agents, calcium channel blockers, aldosterone receptor antagonists, and aldosterone synthase inhibitors, 3-hydroxy-3-methyl-glutaryl coenzyme A reductase inhibitor, HDL increasing compounds such as cholesterol ester transfer protein inhibitor, squalene synthase inhibitor, farnesoid X receptor and liver X receptor ligand, cholestyramine, fibrates, nicotinic acid, or aspirin.

The present invention also relates to the process of preparation of compounds of formula (I), or pharmaceutically acceptable salts thereof.

The compounds of formula (I) may be prepared as outlined in the Schemes 1 to 4 below:

Scheme 1:

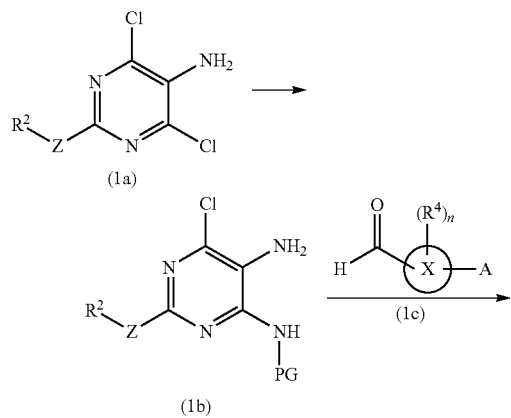

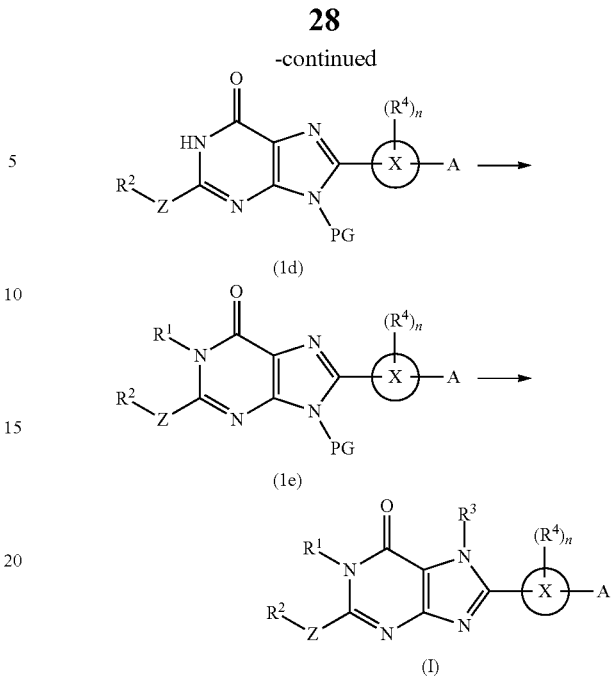

As exemplified in scheme 1 above, pyrimidine derivative of formula (1a), wherein $R^2$ is defined herein above, which is available commercially or can be prepared by well known methods in the art, may be reacted with $PG-NH_2$ such as benzylamine, allylamine and the like to obtain compound of formula (1b). The reaction may be carried out in a solvent such as ethanol, methanol, THF and the like, in an inert atmosphere. The reaction temperature may range from 40° C. to 70° C. The reaction time may range from 6 to 20 hours.

The compound of formula (1b) may be condensed with an aldehyde of formula (1c) in the presence of a suitable solvent or a mixture of solvents, preferably mixture of acetic acid and THF, then refluxed with formic acid to obtain the compound of formula (1d) wherein PG is a protective group and all other symbols are as defined herein above. The reaction temperature may range from 80° C. to 120° C. The reaction time may range from 12 to 36 hours.

The compounds of formula (1d) may be converted into compounds of formula (1e) by reacting with $R^1$-Hal wherein $R^1$ is defined herein above. The reaction may be carried out in a solvent such as acetone or DMF, in the presence of a base such as $K_2CO_3$, $Cs_2CO_3$ or in presence of a suitable organic base such as DBU. The reaction temperature may range from 20 to 40° C.

The protecting group of the compound of (1e) may be removed by means well known in the art to provide compounds of formula I, wherein $R^3$ is H, which is reacted with $R^3$—Hal wherein $R^3$ is defined herein above to provide the desired compound of formula (I) wherein $R^3$ is not H and all other symbols are as defined herein above.

Functional groups as substituents on A may be transformed to different functional groups such as an ester function being converted to an acid, amide, hydroxymethyl, keto, aldehyde as well as an ester. The said conversions may be carried out using reagents and conditions well documented in the literature.

Scheme 2:

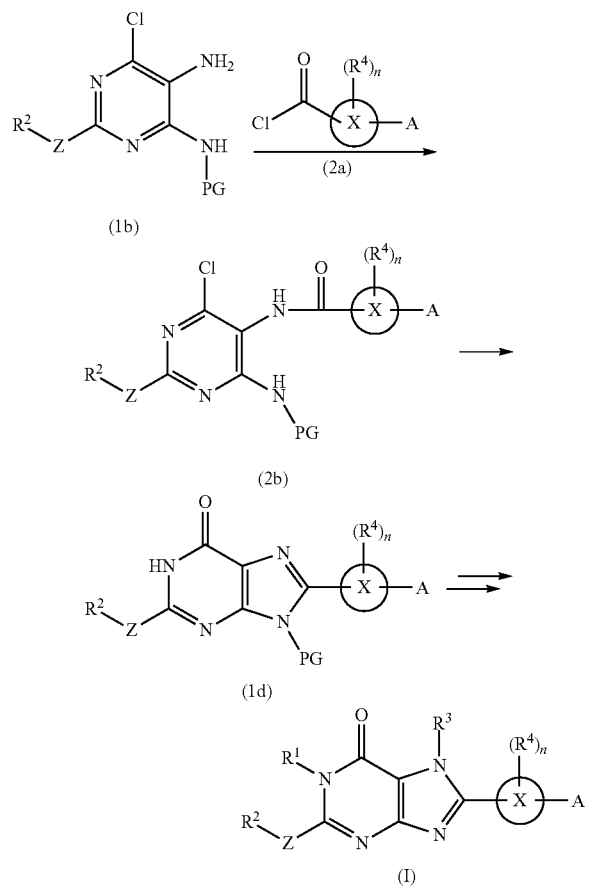

Scheme 3:

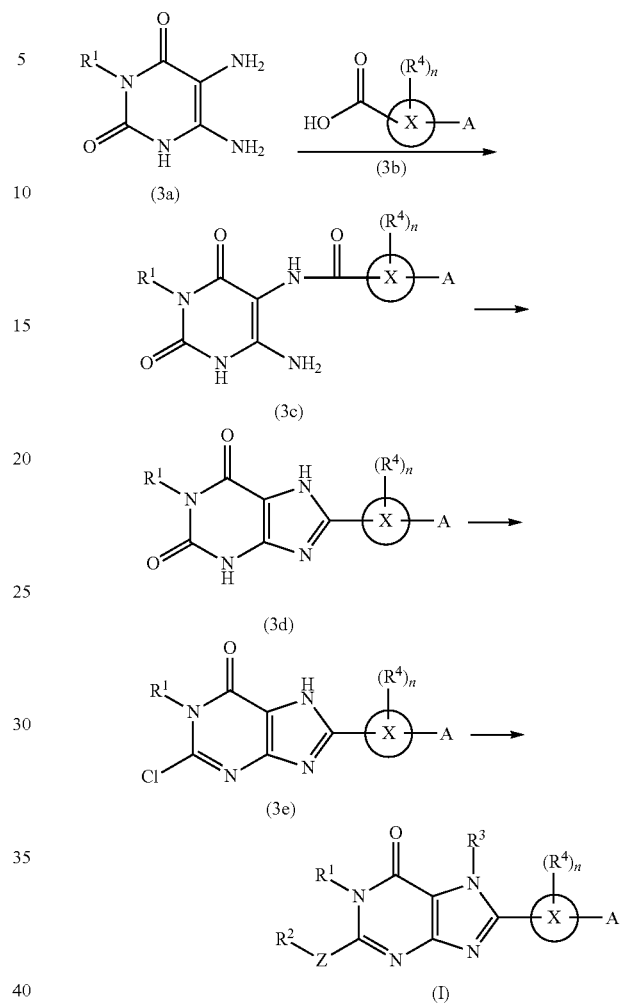

The compounds of formula (1d) may also be prepared by reacting acid chloride of formula (2a) with (1b) to provide (2b). The reaction may be carried out in a basic solvent such as pyridine, N-methylpyrrolidinone and the like or alternatively in an inert solvent such as THF, DCM, N,N-dimethyl acetamide and the like in presence of suitable organic base such as triethylamine, diisopropyl amine and the like. The reaction temperature may range from 0° C. to room temperature. The reaction time may range from 4 to 48 hours. The acid halides (2a) may be commercially available or can be prepared by conventional methods well-known to those skilled in the art. The intermediate (2b) may then be cyclized to obtain compounds of formula (1d) by refluxing in a weak acid such as formic acid, acetic acid and the like or with sulphuric acid in an appropriate solvent such as isopropanol, toluene and the like. The reaction time may range from 6-36 hours.

The compounds of formula (1d) may be converted into compounds of formula (I) as described in scheme 1 above.

Functional groups as substituents on A may be transformed to different functional groups such as an ester function being converted to an acid, amide, hydroxymethyl, keto, aldehyde as well as an ester. The said conversions may be carried out using reagents and conditions well documented in the literature.

Also, when $R^3$ is a protecting group such as benzyl, allyl and the like, it may be deprotected by using reagents and conditions well documented in the literature to obtain compounds of formula (1) wherein $R^3$ is hydrogen which may be further converted to compounds of formula (1) wherein $R^3$ is defined herein above.

The compound of formula (3a), wherein all symbols are defined earlier is prepared by means well known in the art (US2008/0194593).

A compound of formula (3a) is reacted with a carboxylic acid of formula (3b), (which is available commercially or prepared by means well known in the art), wherein all symbols are defined earlier, to yield a compound of formula (3c). The reaction may be carried out using a suitable coupling agent such as EDCI, DCC, HBTU, HATU and the like in a protic solvent such as methanol, ethanol, propanol and the like or an aprotic solvent such as DMF, $CH_2Cl_2$ and the like at a temperature in the range of 20-30° C. for 4 to 16 hours to provide compound of formula (3c).

The compound (3c) may also be prepared from reaction of (3a) with an acid halide of (3b). The reaction is carried out in a solvent such as acetonitrile, THF and the like, in the presence of tertiary base such as triethyl amine. The reaction temperature may range from 0° C. to reflux temperature of the solvent(s) used. The reaction time may range from 4 to 48 hours. After completion of reaction the product of formula (3c) is isolated by conventional methods.

The compound of formula (3c) is cyclised to obtain compounds of formula (3d) by a cyclization reaction. The reaction may be carried out in the presence of hexamethyldisilazane and ammonium sulphate for about 24-48 hours at reflux temperature.

The compound (3d) may also be prepared from reaction of (3c) with a suitable dehydrating reagent preferably phosphorous pentaoxide ($P_4O_{10}$). In general the compound of formula (3c) is dissolved in DMF and excess $P_4O_{10}$ was added to it in one portion. The reaction temperature may range from 80 to 120° C., more preferably 100° C. The reaction time may range from 5 to 40 minutes. After completion of reaction the product of formula (3d) is isolated by conventional methods.

Compounds of formula (3d) may be converted to compounds of formula (3e) by treatment with dehydrating agent such as $POCl_3$ or combination of $POCl_3$ and $PCl_5$, or $POCl_3$ and ammonium chloride, or $POCl_3$ and tetramethyl ammonium chloride at reflux temperature for about 24 to 48 hours. Alternatively (3c) may be converted into compounds of formula (3e) by reaction with dehydrating agent such as $POCl_3$ or combination of $POCl_3$ and $PCl_5$, or $POCl_3$ and ammonium chloride, or $POCl_3$ and tetramethyl ammonium chloride at reflux temperature for about 24 to 48 hours. Compounds of formula (3e) may be converted to compounds of formula (I) by reacting with $R^2$—$NH_2$, $R^2R^2NH$, $R^2OH$, $R^2$—$B(OH)_2$, $R^2MgBr$, $R^2ZnCl$, $R^2CH^2OH$, $R^2SH$, etc. wherein $R^2$ is defined herein above, by methods well known in the art to provide compounds of formula I, wherein $R^3$ is H and all other symbols are defined herein above which may be further reacted with $R^3$—Hal wherein $R^3$ is defined herein above to provide the desired compound of formula (I) wherein $R^3$ is not H and all other symbols are as defined herein above.

Functional groups as substituents on A may be transformed to different functional groups such as an ester function being converted to an acid, amide, hydroxymethyl, keto, aldehyde as well as an ester. The said conversions may be carried out using reagents and conditions well documented in the literature.

Also, when $R^3$ is a protecting group such as benzyl, allyl and the like, it may be deprotected by using reagents and conditions well documented in the literature to obtain compounds of formula (1) wherein $R^3$ is hydrogen which may be further converted to compounds of formula (1) wherein $R^3$ is defined herein above.

Scheme 4:

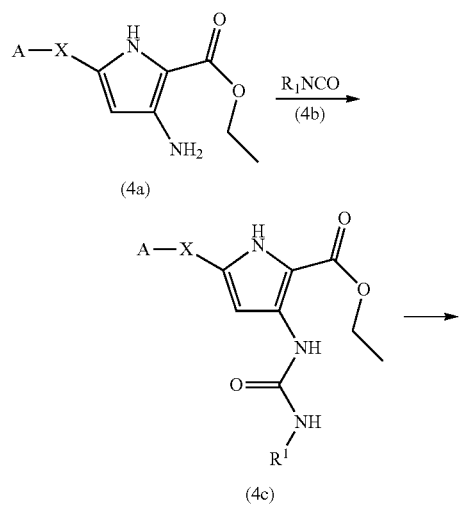

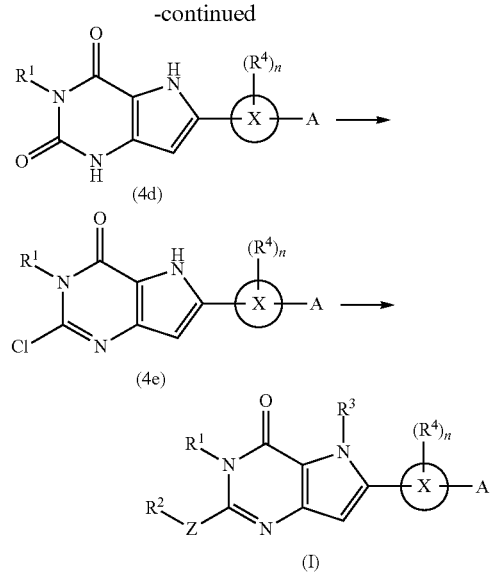

The compound of formula (4a) wherein all symbols are as defined earlier, is prepared by means well known in the art (J. Med. Chem., 2005, 48, 2420-2431, J. Org. Chem., 2000, 65, 2603-2605). The compound of formula (4a) can be converted to compound (4c) by reaction with appropriate isocyanate of formula (4b), wherein all symbols are defined earlier. The reaction may be carried out in an inert solvent, for example toluene, benzene and the like. The reaction temperature may range from room temperature to reflux temperature of the solvent used, preferably at room temperature. The reaction time may range from 1 to 24 hours. After completion of reaction, the product of formula (4c) is isolated by conventional method.

The compound of formula (4c) is then converted into a compound of general formula (4d) by a cyclization reaction. The reaction may be carried out in a protic solvent, for example methanol, ethanol, propanol and the like, preferably methanol, in presence of a base, for example alkali metal hydroxide such as potassium hydroxide, sodium hydroxide and the like, or sodium methoxide, sodium ethoxide, potassium tort-butoxide, preferably aqueous potassium hydroxide, at a temperature 50-100° C., preferably at 80° C. The reaction time may range from 1 to 12 hours, preferably about 6 to 10 hours. After completion of reaction the product of formula (4d) is isolated by conventional method.

Compounds of formula (4d) may be converted to compounds of formula (4e) by treatment with dehydrating agent $POCl_3$ or in combination with $POCl_3$-$PCl_5$, at reflux temperature for about 24 hours. After completion of reaction, (4e) is isolated conventionally.

Compounds of formula (4e) may be converted to compounds of formula (I) by reacting with $R^2$—$NH_2$, $R^2R^2NH$, $R^2$—$B(OH)_2$, $R^2MgBr$, $R^2ZnCl$, $R^2OH$ wherein $R^2$ is defined herein above, by methods well known in the art to provide compounds of formula I, wherein $R^3$ is H and all other symbols are defined herein above which may be further reacted with $R^3$—Hal wherein $R^3$ is defined herein above to provide the desired compound of formula (I) wherein $R^3$ is not H and all other symbols are as defined herein above.

Functional groups as substituents on A may be transformed to different functional groups such as an ester function being converted to an acid, amide, hydroxymethyl, keto, aldehyde as well as an ester. The said conversions may be carried out using reagents and conditions well documented in the literature.

Also, when R³ is a protecting group such as benzyl, allyl and the like, it may be deprotected by using reagents and conditions well documented in the literature to obtain compounds of formula (1) wherein R³ is hydrogen which may be further converted to compounds of formula (1) wherein R³ is as defined herein above.

Scheme 5:

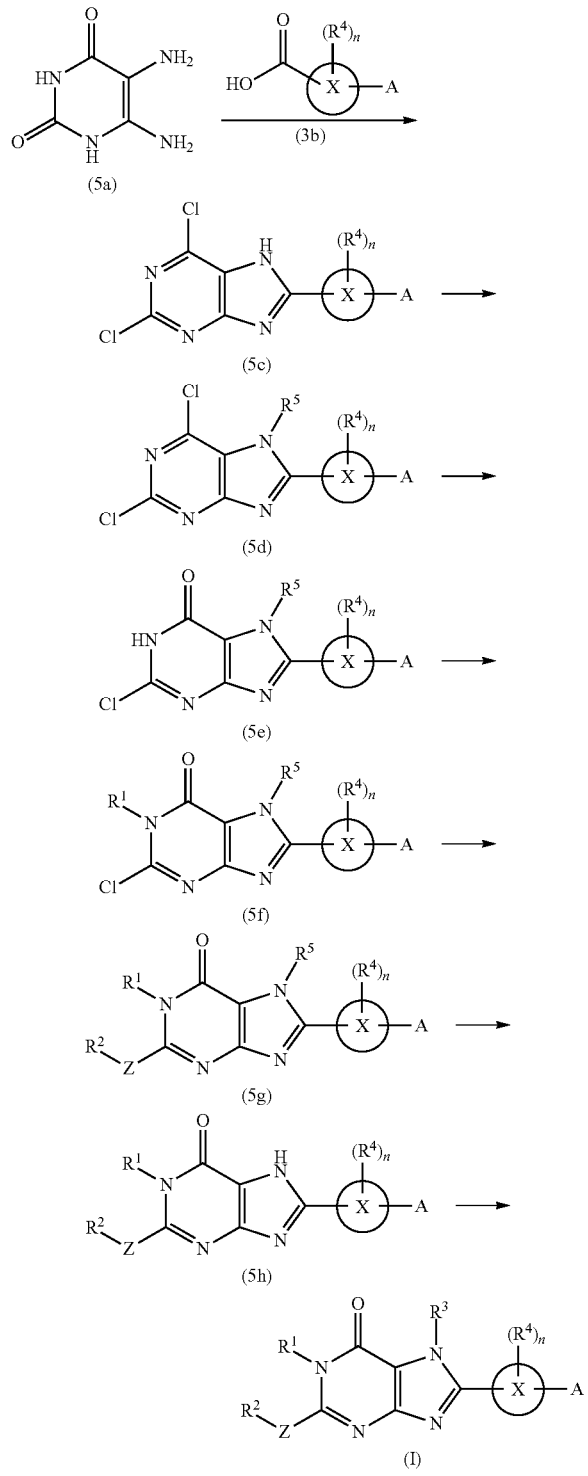

5,6-Diamino-1H-pyrimidine-2,4-dione (5a) which is available commercially or prepared by means well known in the art, may be converted to compounds of formula (5c) by treatment with compounds (3b) and dehydrating agent such as $POCl_3$ or combination of $POCl_3$ and $PCl_5$, or $POCl_3$ and ammonium chloride, or $POCl_3$ and tetramethyl ammonium chloride at reflux temperature for about 24 to 48 hours. Alternatively (5a) may be converted into compounds of formula (5c) by reacting with compounds (3b) and dehydrating agent such as $POCl_3$ or combination of $POCl_3$ and $PCl_5$, or $POCl_3$ and ammonium chloride, or $POCl_3$ and tetramethyl ammonium chloride at reflux temperature for about 24 to 48 hours.

Compounds of formula (5c) wherein all symbols are defined herein above, may be converted to compounds of formula (5d) by using suitable protecting group like trimethyl methyl silyl chloride (SEM-Cl) and the like by using solvent like DMF and the like. The compounds of formula (5d) may be converted into compounds of formula (5e) by using suitable inorganic bases like $Na_2CO_3$, $K_2CO_3$, $NaHCO_3$ and the like and a solvent such as THF, acetone, methanol and the like. Compounds of formula (5e) may be reacted with an alkylating agent R¹-LG wherein R¹ is defined herein above and LG is leaving group such as chloride, bromide, iodode, mesulate and the like, in presence of base such as $Na_2CO_3$, $K_2CO_3$, NaHCO+, NaH and solvent such as THF, acetone, DMF, NMP and the like to obtained compounds of formula (5f) wherein all the symbols are defined herein above. The compounds of formula (5f) may be reacted with $R^2—NH_2$, $R^2R^2NH$, $R^2OH$, $R^2—B(OH)_2$, $R^2MgBr$, $R^2ZnCl$, $R^2CH^2OH$, $R^2SH$, wherein R² is defined herein above, by methods well known in the art to provide compounds of formula (5g) wherein all the symbols are defined herein above. The compound of formula (5g) may be converted to compounds of formula (5h) by using suitable deprotecting agent such as HCl, TFA and the like in presence of solvent such as methanol, ethanol and the like. The compounds of formula (5h) may be converted to compound of formula (I) wherein R³ is H and all other symbols are defined herein above which may be further reacted with R³—Hal wherein R³ is defined herein above to provide the desired compound of formula (I) wherein R³ is not H and all other symbols are as defined herein above.

Wherever desired or necessary, in any of the above mentioned processes, any of the compounds of formula (I) may be converted into a pharmaceutically acceptable salt or vice versa or converting one salt form into another pharmaceutically acceptable salt form.

According to an embodiment, the compounds of the present invention are adenosine $A_1$ receptor antagonists. Thus, the present invention provides a method for the modulation of adenosine $A_1$ receptor activity in mammals which method comprises administering to a mammal in need thereof a therapeutically effective amount of compound of formula I or its tautomers, polymorphs, stereoisomers, prodrugs, solvate or a pharmaceutically acceptable salts thereof.

According to an embodiment, the compounds of the present invention are adenosine $A_{2A}$ receptor antagonists. Thus, the present invention provides a method for the modulation of adenosine $A_{2A}$ receptor activity in mammals which method comprises administering to a mammal in need thereof a therapeutically effective amount of compound of formula I or its tautomers, polymorphs, stereoisomers, prodrugs, solvate or a pharmaceutically acceptable salts thereof.

According to an embodiment, the compounds of the present invention are adenosine $A_{2B}$ receptor antagonists. Thus, the present invention provides a method for the modulation of adenosine $A_{2B}$ receptor activity in mammals which method comprises administering to a mammal in need thereof a therapeutically effective amount of compound of formula I or its tautomers, polymorphs, stereoisomers, prodrugs, solvate or a pharmaceutically acceptable salts thereof.

According to yet another embodiment, the compounds of the present invention are adenosine $A_1$ and $A_{2A}$ antagonist or adenosine $A_1$ and $A_{2B}$ antagonist or $A_1$, $A_{2A}$ and $A_{2B}$ antagonist thereby providing dual or pan antagonistic activity through additive/synergistic effect. Thus, the present invention provides a method for the modulation of adenosine $A_1$ and $A_{2A}$ or $A_1$ and $A_{2B}$ or $A_1$, $A_{2A}$ and $A_{2B}$ receptor activity in mammals which method comprises administering to a mammal in need thereof a therapeutically effective amount of compound of formula I or its tautomers, polymorphs, stereoisomers, prodrugs, solvate or a pharmaceutically acceptable salts thereof.

The present invention also provides a method of prophylactic or therapeutic treatment of disease or disorder susceptible to improvement by antagonism of adenosine receptor comprising administering an effective amount of compound of formula I or its tautomers, polymorphs, stereoisomers, prodrugs, solvate or a pharmaceutically acceptable salts thereof, to a mammal in need of such treatment.

As used throughout the specification and in the claims, the term "treatment" embraces all the different forms or modes of treatment as known to those of the pertinent art and in particular includes preventive, curative, delay of progression and palliative treatment.

The term "therapeutically effective amount" as used herein refers to an amount of a drug or a therapeutic agent that will elicit the desired biological or medical response of a tissue, system or an animal (including man) that is being sought by a researcher or clinician.

The term "mammal" or "patient" are used interchangeably herein and include, but are not limited to, humans, dogs, cats, horses, pigs, cows, sheep, monkeys, rabbits, mice and laboratory animals The preferred mammals are humans.

The present invention further provides pharmaceutical compositions comprising a therapeutically effective amount of a compound of the present invention, alone or in combination with one or more pharmaceutically acceptable carriers.

The pharmaceutical compositions according to the invention are those suitable for enteral, such as oral or rectal, transdermal and parenteral administration to mammals, including man, for the treatment of conditions mediated by the adenosine $A_1$ receptor or adenosine $A_{2A}$ receptor or adenosine $A_{2B}$ receptor. Such conditions include, but are not limited to, asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, and/or autoimmune diseases.

Generally, the concentration of the compound(s) of the present invention in a liquid composition, such as a lotion, will be from about 0.01-about 25 wt %, preferably from about 0.1-about 10 wt %. The concentration in a semi-solid or a solid composition such as a gel or a powder will be about 0.1-about 5 wt %, preferably about 0.5-about 25 wt %.

The amount of a compound of the present invention required for use in treatment will vary not only with the particular salt selected but also with the route of administration, the nature of the condition being treated and the age and condition of the patient and will be ultimately at the discretion of the administering physician or clinician. In general, a suitable dose will be in the range of from about 0.001 mg/kg/day to about 20 mg/kg/day For example, a dosage may be from about 0.002 mg/kg to about 10 mg/kg of body weight per day, from about 0.01 mg/kg/day to about 1 mg/kg/day, and from about 0.1 mg/kg/day to about 5 mg/kg/day.

The compound is conveniently administered in unit dosage form, e.g., containing 5 to 1000 μg, about 10 to about 750 μg, about 50 to about 500 μg of active ingredient per unit dosage form.

The desired dose may conveniently be presented in a single dose or as divided doses administered at appropriate intervals, for example, as two, three, four or more sub-doses per day. The sub-dose itself may be further divided, e g, into a number of discrete loosely spaced administrations; such as multiple inhalations from an insufflator or by application of a plurality of drops into the eye Dosages above or below the range cited herein above are within the scope of the present invention and may be administered to the individual patient if desired and necessary.

Accordingly, in various embodiments, the present invention provides pharmaceutical compositions as described above for the treatment of conditions mediated by adenosine receptor, such as asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, and/or autoimmune diseases.

In various embodiments, the present invention provides pharmaceutical compositions comprising a therapeutically effective amount of a compound of the invention in combination with a therapeutically effective amount of another therapeutic agent, preferably selected from anti-inflammatory agents, anti-diabetic agents, anti-hypertensive agents and anti-dyslipidemic agents.

According to an embodiment, the pharmaceutical compositions may contain a therapeutically effective amount of a compound of the invention as defined above, either alone or in a combination with another therapeutic agent, e.g., each at an effective therapeutic dose as reported in the art. Such therapeutic agents include: a) anti-inflammatory agents, such as anticholinergic or antimuscarinic agents; steroids; $LTB_4$ (leukotriene $B_4$) antagonists; dopamine receptor agonists; $PDE_4$ (phosphodiesterase 4) inhibitors; and beta-2 adrenergic receptor agonists; b) anti-diabetic agents, such as insulin, insulin derivatives and mimetics; insulin secretagogues; insulinotropic sulfonylurea receptor ligands; thiazolidone derivatives; GSK3 (glycogen synthase kinase-3) inhibitors; sodium-dependent glucose co-transporter inhibitors; glycogen phosphorylase A inhibitors; biguanides; alpha-glucosidase inhibitors; GLP-1 (glucagon like peptide-1), GLP-1 analogs and GLP-1 mimetics; modulators of PPARs (peroxisome proliferator-activated receptors); DPPIV (dipeptidyl peptidase IV) inhibitors; SCD-1 (stearoyl-CoA desaturase-1) inhibitors; DGAT1 and DGAT2 (diacylglycerol acyltransferase 1 and 2) inhibitors; ACC2 (acetyl CoA carboxylase 2) inhibitors; and breakers of AGE (advanced glycation end products); c) anti-hypertensive agents, such as loop diuretics; angiotensin converting enzyme (ACE) inhibitors; inhibitors of the Na—K-ATPase membrane pump such as digoxin; neutralendopeptidase (NEP) inhibitors; ACE/NEP inhibitors; angiotensin II antagonists; renin inhibitors; β-adrenergic receptor blockers; inotropic agents; calcium channel blockers; aldosterone receptor antagonists; and aldosterone synthase inhibitors; and d) anti-dyslipidemic agents such as 3-hydroxy-3-methyl-glutaryl coenzyme A (HMG-CoA)-reductase inhibitors; HDL increasing compounds such as cholesterol ester transfer protein (CETP) inhibitors; squalene synthase inhibitors; FXR (farnesoid X receptor) and LXR (liver X receptor) ligands; cholestyramine; fibrates; nicotinic acid; and aspirin.

As described above, a compound of the present invention may be administered either simultaneously, before or after another active ingredient, either separately by the same or different route of administration or together in the same pharmaceutical formulation.

The present invention further relates to pharmaceutical compositions as described above for use as a medicament.

The present invention further relates to use of pharmaceutical compositions or combinations as described above for the preparation of a medicament for the treatment of conditions mediated by adenosine receptor, such as asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus; obesity, inflammatory gastrointestinal tract disorders, and/or autoimmune diseases.

According to an embodiment, the present invention provides use of compound of formula (I) for the treatment of conditions mediated by adenosine receptor.

According to an embodiment, the present invention provides use of compound of formula (I) for the treatment of asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, autoimmune diseases.

According to an embodiment, the present invention provides use of compound of formula (I) for use in preparation of medicament useful in the treatment of conditions mediated by adenosine receptor.

EXAMPLES

The invention is further illustrated by the following examples which in no way should be construed as being further limiting. One skilled in the art will readily appreciate that the specific methods and results described are merely illustrative. Structures of the intermediates as well as the final compounds were confirmed by nuclear magnetic resonance spectra for proton ($^1$H NMR) and LCMS.

Preparation 1: 2-chloro-8-cyclopentyl-1-propyl-1,7-dihydro-purin-6-one

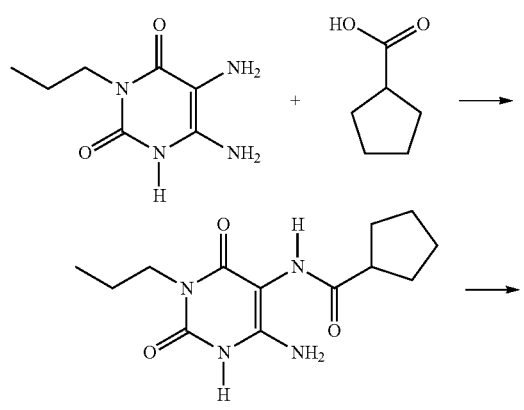

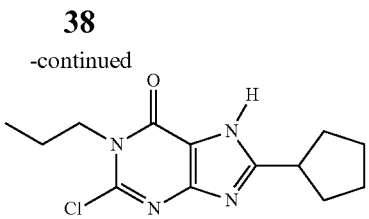

Step 1: Cyclopentane carboxylic acid (6-amino-2,4-dioxo-3-propyl-1,2,3,4-tetra hydro-pyrimidin-5-yl)-amide To a solution of 5,6-diamino-3-propyl-1H-pyrimidine-2,4-dione (0.6 g, 2.72 mmol) in methanol (50 ml) was added cyclopentane carboxylic acid (0.310 g, 2.72 mmol). The reaction mixture was cooled to 0° C. and then 1-ethyl-3(3'-dimethylaminopropyl) carbodiimide hydrochloride (EDCI.HCl) (0.78 g, 4.1 mmol) was added. The resulting reaction mixture was stirred at room temperature overnight. The reaction mixture was concentrated under reduced pressure. The residue was dissolved in water. The solid was filtered and washed thoroughly with water followed by diethyl ether. The product obtained was dried under high vacuum. The crude product (0.40 g) was used for the next step without further purification.

Step 2: Preparation of 8-cyclopentyl-2-chloro-1-propyl-1,7-dihydro-purin-6-one

To a suspension of cyclopentanecarboxylic acid (6-amino-2,4-dioxo-3-propyl-1,2,3,4-tetrahydro-pyrimidin-5-yl)-amide (0.40 g, crude) obtained from step 1 in phosphorus oxychloride (25 ml) was added phosphorus pentachloride (0.10 g) and the resulting reaction mixture was refluxed overnight. Phosphorus oxychloride was evaporated under reduced pressure. The residue was slowly quenched with water. Ethyl acetate was added and the organic layer was separated and washed thoroughly with water followed by brine. The ethyl acetate layer was dried over anhydrous sodium sulphate and concentrated under vacuum. The crude product was purified by preparative TLC using dichloromethane, methanol (9:1) as the solvent system to give 0.075 g (19% over two steps) of the product as a white solid.

$^1$HNMR (400 MHz, DMSO d6): δ 0.9 (t, J=8 Hz, 3H), 1.59-1.82 (m, 8H), 1.99 (m, 2H), 3.15 (t, J=8 Hz, 1H), 4.12 (t, J=8 Hz, 2H).

Preparations 2 to 7 were prepared following the experimental procedure as given for Preparation 1.

Preparation 2: 2-Chloro-8-cyclohexyl-1-propyl-1,7-dihydro-purin-6-one,

Preparation 3: 2-Chloro-8-cyclopropyl-1-propyl-1,7-dihydro-purin-6-one,

Preparation 4: 2-Chloro-8-(hexahydro-2,5-methano-pentalen-3a-yl)-1-propyl-1,7-dihydro-purin-6-one, Preparation 5: 8-Bicyclo-[2.2.1]-hept-2-yl-2-chloro-1-propyl-1,7-dihydro-purin-6-one, Preparation 6: 8-Adamantan-2-yl-2-chloro-1-propyl-1,7-dihydro-purin-6-one, Preparation 7: 3-[4-(2-Chloro-6-oxo-1-propyl-6,7-dihydro-1H-purin-8-yl)-bicyclo[2.2.2]oct-1-yl]-propionic acid.

Example 1

8-Cyclopentyl-2-(3,4-difluoro-phenoxy)-1-propyl-1,7-dihydro-purin-6-one

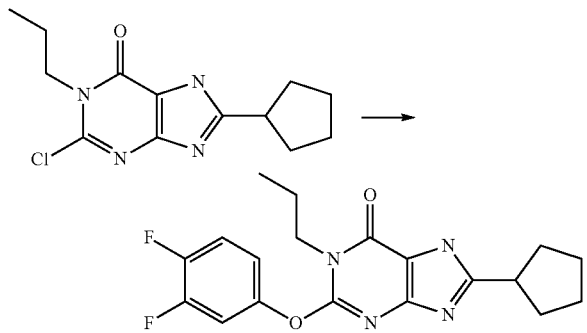

To a solution of 8-cyclopentyl-2-chloro-1-propyl-1,7-dihydro-purin-6-one (0.06 g, 0.21 mmol) in N-methyl-2-pyrrolidone (0.2 ml) was added $K_2CO_3$ (0.044 g, 0.32 mmol) followed by 3,4-difluoro phenol and the reaction mixture was heated at 130° C. overnight. The reaction mixture was diluted with ethyl acetate and water. The layers were separated and ethyl acetate layer was washed with water. The ethyl acetate layer was dried over anhydrous sodium sulphate and concentrated under vacuum. The crude product was purified by preparative TLC using 3% methanol in DCM to give the product (0.015 g, 19%) as a white solid.

$^1$HNMR (400 MHz, DMSO d6): δ 0.94 (t, J=8 Hz, 3H), 1.59-1.74 (m, 6H), 1.94 (br.s, 2H), 3.12 (m, 2H), 4.09 (br. s, 2H), 7.21 (d, J=8 Hz, 1H), 7.53-7.65 (m, 2H), 12.74 (br.s, 1H).

Example 2 to 69 was prepared following the experimental procedure as given for Example 1.

| Example No. | Structure and IUPAC name | NMR |
|---|---|---|
| 2 | 8-Cyclopentyl-2-(2-fluoro-phenoxy)-1-propyl-1,7-dihydro-purin-6-one. | $^1$HNMR (400 MHz, DMSO-d6): δ 0.96 (t, 8 Hz, 3H), 1.59 (b.s, 2H), 1.71-1.77 (b.s, 6H), 1.94 (b.s, 2H), 3.09 (b.s, 1H), 4.15 (b.s, 2H), 7.31-7.39 (m, 1H), 7.41-7.48 (m, 3H), 12.97 (b.s, 1H) |
| 3 | 8-Adamantan-1-yl-2-(4-fluoro-phenoxy)-1-propyl-1,7-dihydro-purin-6-one. | 1HNMR (400 MHz, CD3OD): 0.98-1.05 (m, 3H); 1.76-1.90 (m, 8H); 1.94-2.12 (m, 9H); 4.19-4.29 (m, 2H); 7.14-7.32 (m, 4H). |
| 4 | 8-Adamantan-1-yl-2-(3-fluoro-phenoxy)-1-propyl-1,7-dihydro-purin-6-one. | 1HNMR (400 MHz, CD3OD): 0.99-1.08 (t, J = 6.8 Hz, 3H); 1.76-1.90 (m, 8H); 1.96-2.12 (m, 9H); 4.19-4.29 (m, 2H); 7.02-7.19 (m, 3H); 7.42-7.51 (m, 1H). |

| Example No. | Structure and IUPAC name | NMR |
|---|---|---|
| 5 | 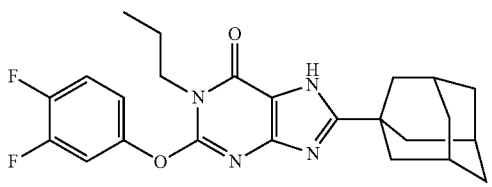 [SMILES: CCCn1c(Oc2ccc(F)c(F)c2)nc2nc(C34CC5CC(CC(C5)C3)C4)[nH]c2c1=O]<br>8-Adamantan-1-yl-2-(3, 4-difluoro-phenoxy)-1-propyl-1,7-dihydro-purin-6-one. | 1HNMR (400 MHz, CD3OD): 0.99-1.08 (t, J = 6.8 Hz, 3H); 1.76-1.90 (m, 8H); 1.96-2.12 (m, 9H); 4.19-4.27 (m, 2H); 7.08-7.15 (m, 1H); 7.42-7.51 (m, 2H). |
| 6 | 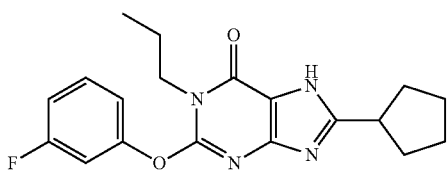 [SMILES: CCCn1c(Oc2cccc(F)c2)nc2nc(C3CCCC3)[nH]c2c1=O]<br>8-Cyclopentyl-2-(3-fluoro-phenoxy)-1-propyl-1,7-dihydro-purin-6-one. | $^1$HNMR (400 MHz, CD3OD): δ 1.05 (t, 4 Hz, 3H), 1.69-1.90 (m, 8H), 2.09-2.11 (m, 2H), 4.25 (t, 8 Hz, 2H), 7.06-7.17 (m, 3H), 7.45-7.51 (m, 1H), |
| 7 | 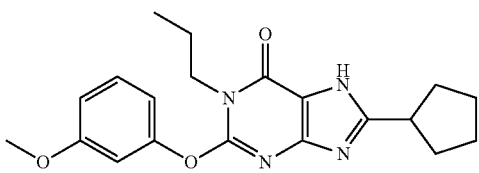 [SMILES: CCCn1c(Oc2cccc(OC)c2)nc2nc(C3CCCC3)[nH]c2c1=O]<br>8-Cyclopentyl-2-(3-methoxy-phenoxy)-1-propyl-1,7-dihydro-purin-6-one. | $^1$HNMR (400 MHz, CD3OD): δ 1.03-1.07 (t, 8 Hz, 3H), 1.69-1.72 (m, 2H), 1.77-1.89 (m, 6H), 2.05-2.12 (m, 2H), 3.15-3.21 (m, 1H), 3.82 (s, 3H), 4.25 (t, 8 Hz, 3H), 6.81-6.89 (m, 3H), |
| 8 | 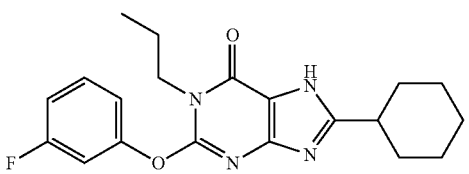 [SMILES: CCCn1c(Oc2cccc(F)c2)nc2nc(C3CCCCC3)[nH]c2c1=O]<br>8-Cyclohexyl-2-(3-fluoro-phenoxy)-1-propyl-1,7-dihydro-purin-6-one. | 1HNMR (400 MHz, CD3OD): d 1.027 (t, J = 7.4 Hz, 3H); 1.24-2.06 (m, 12H); 2.687-2.87 (m, 1H); 4.221 (t, J = 7.4 Hz, 2H); 7.024-7.15 (m, 2H); 7.418-7.492 (m, 1H). |
| 9 | 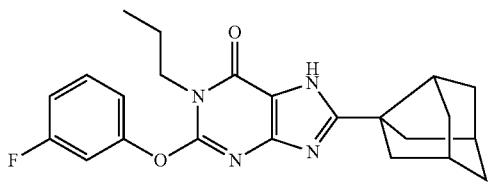 [SMILES: CCCn1c(Oc2cccc(F)c2)nc2nc(C34CC5CC(CC3C5)C4)[nH]c2c1=O]<br>2-(3-Fluoro-phenoxy)-8-(hexahydro-2,5-methano-pentalen-3a-yl)-1-propyl-1,7-dihydro-purin-6-one. | $^1$HNMR (400 MHz, CD3OD): δ 1.01 (t, 8 Hz, 3H), 1.64-1.71 (m, 4H), 1.80-1.90 (m, 2H), 1.95-2.00 (m, 4H), 2.11-2.14 (m, 2H), 2.33 (s, 2H), 4.23 (t, 8 Hz, 2H), 7.04-7.14 (m, 3H), 7.42-7.48 (m, 1H), |

| Example No. | Structure and IUPAC name | NMR |
|---|---|---|
| 10 | 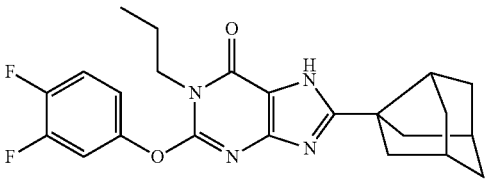 [SMILES: CCCn1c(Oc2ccc(F)c(F)c2)nc2nc(C34CC5CC(CC3C5)C4)[nH]c2c1=O]<br>2-(3,4-Difluoro-phenoxy)-8-(hexahydro-2,5-methano-pentalen-3a-yl)-1-propyl-1,7-dihydro-purin-6-one. | $^1$HNMR (400 MHz, CD3OD): δ 1.03 (t, 8 Hz, 3H), 1.67-1.74 (m, 4H), 1.84-1.89 (m, 3H), 1.97-2.02 (m, 4H), 2.35 (s, 2H), 4.24 (t, 8 Hz, 2H), 7.12-7.14 (m, 1H), 7.34-7.41 (m, 2H), |
| 11 | 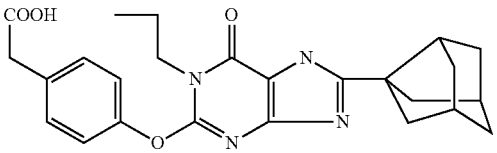 [SMILES: CCCn1c(Oc2ccc(CC(=O)O)cc2)nc2nc(C34CC5CC(CC3C5)C4)[nH]c2c1=O]<br>{4-[8-(Hexahydro-2,5-methano-pentalen-3a-yl)-6-oxo-1-propyl-6,7-dihydro-1H-purin-2-yloxy]-phenyl}-acetic acid. | $^1$HNMR (400 MHz, DMSO-d6): δ 0.94 (t, 8 Hz, 3H), 0.94 (t, 8 Hz, 3H), 1.56-1.58 (m, 4H), 1.70-1.75 (m, 2H), 1.80-1.88 (m, 4H), 2.06-2.08 (m, 3H), 2.25 (s, 2H), 3.61 (s, 2H), 4.09-4.12 (m, 2H), 7.18-7.23 (m, 2H), 7.33-7.35 (d, 8 Hz, 2H), |
| 12 | 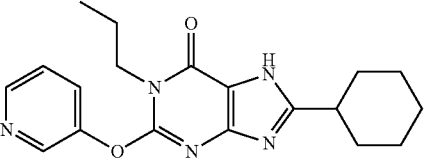 [SMILES: CCCn1c(Oc2cccnc2)nc2nc(C3CCCCC3)[nH]c2c1=O]<br>8-Cyclohexyl-1-propyl-2-(pyridin-3-yloxy)-1,7-dihydro-purin-6-one. | 1HNMR (400 MHz, DMSO d6): d 0.955 (t, J = 7.2 Hz, 3H); 1.10-1.93 (m, 12H); 2.552-2.778 (m, 1H); 4.071-4.208 (m, 2H); 7.45-7.635 (m, 1H); 7.78-7.94 (m, 1H); 8.43-8.72 (m, 2H); 12.711 & 12.964 (2s, 1H). |
| 13 | 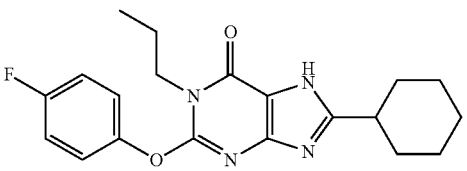 [SMILES: CCCn1c(Oc2ccc(F)cc2)nc2nc(C3CCCCC3)[nH]c2c1=O]<br>8-Cyclohexyl-2-(4-fluoro-phenoxy)-1-propyl-1,7-dihydro-purin-6-one. | 1HNMR (400 MHz, CD3OD): d 1.033 (t, J = 7.4 Hz, 3H); 1.24-2.09 (m, 12H); 2.682-2.806 (m, 1H); 4.234 (t, J = 7.4 Hz, 2H); 7.12-7.33 (m, 4H). |
| 14 | 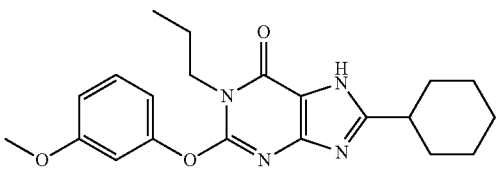 [SMILES: CCCn1c(Oc2cccc(OC)c2)nc2nc(C3CCCCC3)[nH]c2c1=O]<br>8-Cyclohexyl-2-(3-methoxy-phenoxy)-1-propyl-1,7-dihydro-purin-6-one. | 1HNMR (400 MHz, CD3OD): d 1.044 (t, J = 7.4 Hz, 3H); 1.258-2.180 (m, 12H); 2.692-2.809 (m, 1H); 3.814 (s, 3H); 4.240 (t, J = 7.6 Hz, 2H); 6.74-6.83 (m, 3H) 7.32-7.44 (m, 1H). |
| 15 | 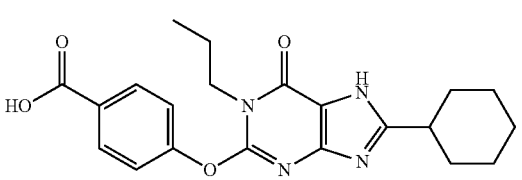 [SMILES: CCCn1c(Oc2ccc(C(=O)O)cc2)nc2nc(C3CCCCC3)[nH]c2c1=O]<br>4-(8-Cyclohexyl-6-oxo-1-propyl-6,7-dihydro-1H-purin-2-yloxy)-benzoic acid. | $^1$HNMR (400 MHz, DMSO d6): 0.94 (t, 7.8 Hz, 3H); 1.10-1.96 (m, 2H); 2.53-2.75 (m, 1H); 4.05-4.17 (m, 2H); 7.33-7.50 (m, 2H); .95-8.10 (m, 2H); 12.63-13.3 (m, 2H). |

| Example No. | Structure and IUPAC name | NMR |
|---|---|---|
| 16 | 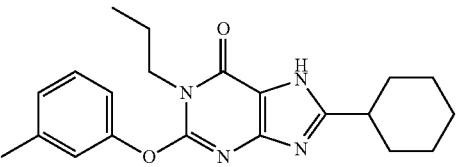 [SMILES: CCCn1c(Oc2cccc(C)c2)nc2nc(C3CCCCC3)[nH]c2c1=O]<br>8-Cyclohexyl-1-propyl-2-m-tolyloxy-1,7-dihydro-purin-6-one. | 1HNMR (400 MHz, DMSO d6): d 0.943 (t, J = 7.6 Hz, 3H); 1.128-1.96 (m, 12H); 2.345 (s, 3H); 2.54-2.76 (m, 1H); 4.103 (t, J = 7.6 Hz, 2H); 6.84-7..42 (m, 4H) 12.58-12.98 (m, 1H). |
| 17 | 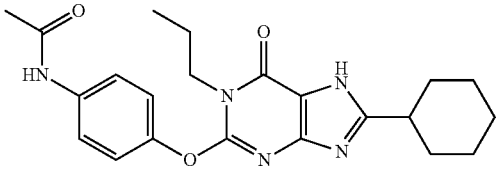 [SMILES: CCCn1c(Oc2ccc(NC(C)=O)cc2)nc2nc(C3CCCCC3)[nH]c2c1=O]<br>N-[4-(8-Cyclohexyl-6-oxo-1-propyl-6,7-dihydro-1H-purin-2-yloxy)-phenyl]-acetamide. | 1HNMR (400 MHz, DMSO d6): d 0.942 (t, J = 7.6 Hz, 3H); 1.22-2.09 (m, 12H); 2.503 (s, 3H); 2.408-2.760 (m, 1H); 4.101-4.302 (t, J = 7.00 Hz, 2H); 7.14-7.36 (m, 2H) 7.45-7.72 (m, 2H); 9.98-10.12 (m, 1H); 12.45-13.4 (m, 1H). |
| 18 | 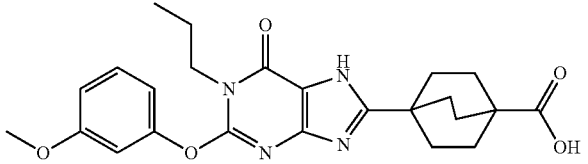 [SMILES: CCCn1c(Oc2cccc(OC)c2)nc2nc(C34CCC(C(=O)O)(CC3)CC4)[nH]c2c1=O]<br>4-[2-(3-Methoxy-phenoxy)-6-oxo-1-propyl-6,7-dihydro-1H-purin-8-yl]-bicyclo[2.2.2]octane-1-carboxylic acid. | $^1$HNMR (400 MHz, CDCl3): δ 1.02 (t, 7.6 Hz, 3H), 1.81-1.87 (m, 2H), 2.03-2.08 (m, 12H); 3.81 (s, 3H); 4.26 (t, J = 7.2 Hz, 2H); 6.73 (s, 1H); 6.79-7.32 (m, 2H); 7.26-7.32 (m, 1H); 12.49 (bs, 1H); 12.53 (bs, 1H); |
| 19 | 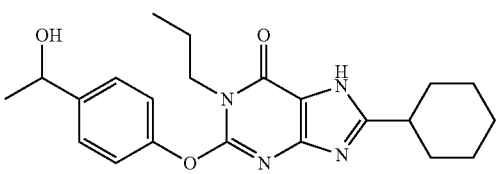 [SMILES: CCCn1c(Oc2ccc(C(C)O)cc2)nc2nc(C3CCCCC3)[nH]c2c1=O]<br>8-Cyclohexyl-2-[4-(1-hydroxy-ethyl)-phenoxy]-1-propyl-1,7-dihydro-purin-6-one. | 1HNMR (400 MHz, CD3OD): d 1.033 (t, J = 7.4 Hz, 3H); 1.23-2.0398 (m, 12H); 2.678-2.820 (m, 1H); 4.241 (t, J = 7.4 Hz, 2H); 4.82-4.872 (m, 1H); 7.178-7.24 (m, 2H); 7.42-7.64 (m, 2H. |
| 20 | 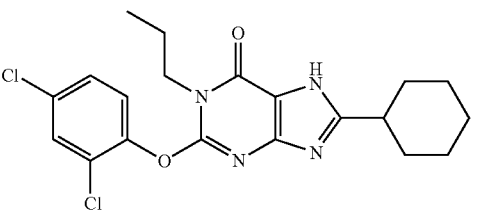 [SMILES: CCCn1c(Oc2ccc(Cl)cc2Cl)nc2nc(C3CCCCC3)[nH]c2c1=O]<br>8-Cyclohexyl-2-(2,4-dichloro-phenoxy)-1-propyl-1,7-dihydro-purin-6-one. | 1HNMR (400 MHz, DMSO d6): d 1.037 (t, J = 7.4 Hz, 3H); 1.22-2.07 (m, 12H); 2.701-2.821 (m, 1H); 4.190-4.302 (m, 2H); 7.35-7.47 (m, 2H) 7.58-7.64 (m, 1H). |

| Example No. | Structure and IUPAC name | NMR |
|---|---|---|
| 21 | 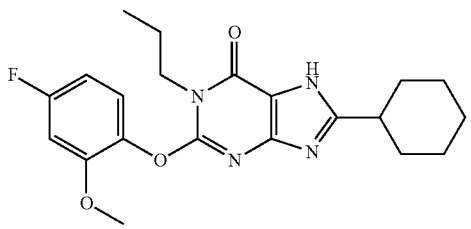 [SMILES: CCCn1c(Oc2ccc(F)cc2OC)nc2nc(C3CCCCC3)[nH]c2c1=O]<br>8-Cyclohexyl-2-(4-fluoro-2-methoxy-phenoxy)-1-propyl-1,7-dihydro-purin-6-one. | 1HNMR (400 MHz, CD3OD): d 0.974-1.056 (m, 3H); 1.238-2.004 (m, 12H); 2.698-2.798 (m, 1H); 3.749 (s, 3H); 4.18-4.24 (m, 2H); 6.7-6.74 (m, 1H); 6.901-6.97 (m, 1H); 7.14-7.24 (m, 1H). |
| 22 | 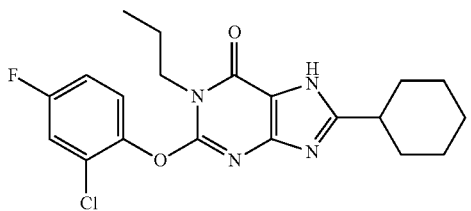 [SMILES: CCCn1c(Oc2ccc(F)cc2Cl)nc2nc(C3CCCCC3)[nH]c2c1=O]<br>2-(2-Chloro-4-fluoro-phenoxy)-8-cyclohexyl-1-propyl-1,7-dihydro-purin-6-one. | 1HNMR (400 MHz, CD3OD): d 1.029 (t, J = 7.4 Hz, 3H); 1.240-2.204 (m, 12H); 2.688-2.799 (m, 1H); 4.2-4.284 (m, 2H); 7.165-7.224 (m, 1H); 7.368-7.455 (m, 2H). |
| 23 | 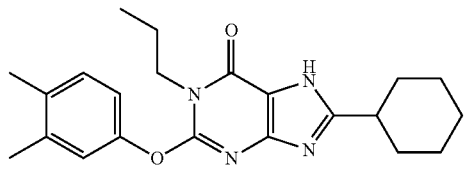 [SMILES: CCCn1c(Oc2ccc(C)c(C)c2)nc2nc(C3CCCCC3)[nH]c2c1=O]<br>8-Cyclohexyl-2-(3,4-dimethyl-phenoxy)-1-propyl-1,7-dihydro-purin-6-one. | 1HNMR (400 MHz, CD3OD): d 1.025 (t, J = 7.4 Hz, 3H); 1.209-2.198 (m, 12H); 2.273 (s, 6H); 2.688-2.809 (m, 1H); 4.16-4.262 (m, 2H); 6.89-7.032 (m; 2H); 7.15-7.201 (m, 1H). |
| 24 | 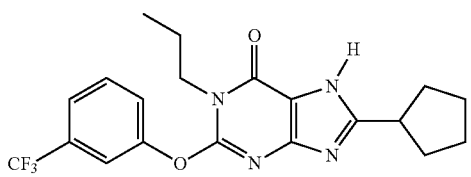<br>8-Cyclopentyl-1-propyl-2-(3-trifluoromethyl-phenoxy)-1,7-dihydro-purin-6-one | $^1$HNMR (400 MHz, CD3OD): δ 1.04 (t, 8 Hz, 3H), 1.66-1.71 (m, 2H), 1.79-1.87 (m, 6H), 2.03-2.08 (m, 1H), 3.16 (m, 1H), 4.23-4.27 (m, 2H), 7.55 (d, 8 Hz, 1H), 7.61-7.67 (m, 3H), |
| 25 | 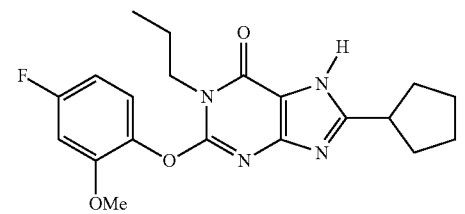 [SMILES: CCCn1c(Oc2ccc(F)cc2OC)nc2nc(C3CCCC3)[nH]c2c1=O]<br>8-Cyclopentyl-2-(4-fluoro-2-methoxy-phenoxy)-1-propyl-1,7-dihydro-purin-6-one. | $^1$HNMR (400 MHz, DMSO d6): δ 1.02 (t, 8 Hz, 3H), 1.66-1.68 (m, 2H), 1.76-1.82 (m, 3H), 1.84-1.89 (m, 3H), 2.03-2.07 (m, 2H), 3.75 (s, 3H), 4.20-4.24 (m, 2H), 6.72-6.75 (td, 1H), 6.92-6.95 (dd, 1H), 7.18-7.21 (m, 1H) |

| Example No. | Structure and IUPAC name | NMR |
|---|---|---|
| 26 | 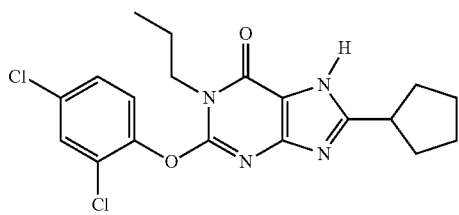 [SMILES: CCCn1c(Oc2ccc(Cl)cc2Cl)nc2nc(C3CCCC3)[nH]c2c1=O]<br>8-Cyclopentyl-2-(2,4-dichloro-phenoxy)-1-propyl-1,7-dihydro-purin-6-one. | $^1$HNMR (400 MHz, CD3OD): δ 1.04 (t, 8 Hz, 3H), 1.67-1.71 (m, 2H), 1.75-1.80 (m, 4H), 1.85-1.93 (m, 2H), 4.23-4.27 (m, 2H), 7.41 (s, 1H), 7.44 (d, 4 Hz, 1H), 7.62 (b.s, 1), |
| 27 | 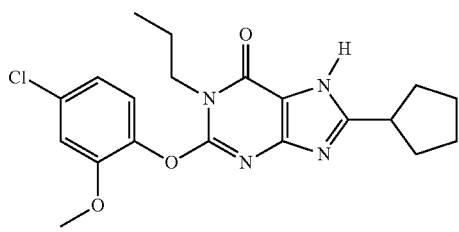 [SMILES: CCCn1c(Oc2ccc(Cl)cc2OC)nc2nc(C3CCCC3)[nH]c2c1=O]<br>2-(4-Chloro-2-methoxy-phenoxy)-8-cyclopentyl-1-propyl-1,7-dihydro-purin-6-one. | $^1$HNMR (400 MHz, DMSO d6): δ 0.91 (t, 8 Hz, 3H), 1.56-1.74 (m, 8H), 1.91 (b.s, 2H), 3.69-3.74 (m, 3H), 4.07 (d, 8 Hz, 2H), 7.05-7.08 (dd, 8 Hz, 1H), |
| 28 | 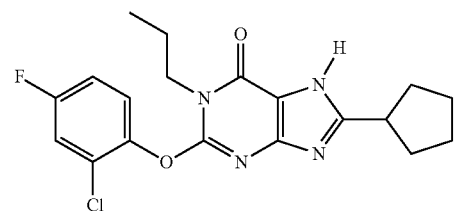 [SMILES: CCCn1c(Oc2ccc(F)cc2Cl)nc2nc(C3CCCC3)[nH]c2c1=O]<br>2-(2-Chloro-4-fluoro-phenoxy)-8-cyclopentyl-1-propyl-1,7-dihydro-purin-6-one. | $^1$HNMR (400 MHz, DMSO d6): δ 0.93 (t, 8 Hz, 3H), 1.56 (b.s, 2H), 1.68-1.75 (m, 6H), 1.91 (b.s, 2H), 4.11 (b.s, 2H), 7.34 (t, 8 Hz, 1H), 7.56 (m, 1H), 7.64-7.66 (m, 1H) |
| 29 | 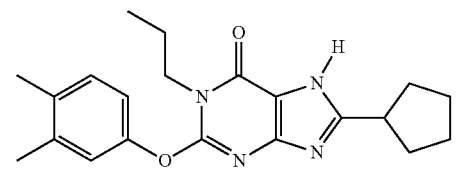 [SMILES: CCCn1c(Oc2ccc(C)c(C)c2)nc2nc(C3CCCC3)[nH]c2c1=O]<br>8-Cyclopentyl-2-(3,4-dimethyl-phenoxy)-1-propyl-1,7-dihydro-purin-6-one. | $^1$HNMR (400 MHz, DMSO d6): δ 0.92 (t, 8 Hz, 3H), 1.55-1.60 (m, 2H), 1.69-1.72 (m, 6H), 1.89-1.93 (m, 2H), 2.21-2.26 (m, 6H), 2.99-3.09 (m, 1H), 4.07 (b.s, 2H), 6.93-7.05 (m, 2H), 7.18 (d, 8 Hz, 1H), 12.9 (b.s, 1H) |
| 30 | 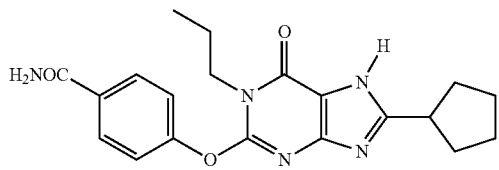 [SMILES: CCCn1c(Oc2ccc(C(N)=O)cc2)nc2nc(C3CCCC3)[nH]c2c1=O]<br>4-(8-Cyclopentyl-6-oxo-1-propyl-6,7-dihydro-1H-purin-2-yloxy)-benzamide. | $^1$HNMR (400 MHz, DMSO d6): δ 0.95 (t, 8 Hz, 3H), 1.58-1.76 (m, 8 H), 1.94 (b.s, 2H), 4.12 (b.s, 2H), 7.35-7.44 (m, 1H), 7.97 (d, 8 Hz, 3 H) |

| Example No. | Structure and IUPAC name | NMR |
|---|---|---|
| 31 | 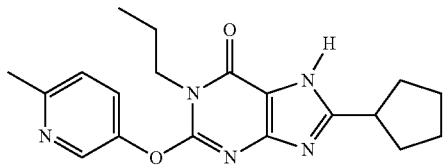 [SMILES: CCCn1c(Oc2ccc(C)nc2)nc2nc(C3CCCC3)[nH]c2c1=O]<br>8-Cyclopentyl-2-(6-methyl-pyridin-3-yloxy)-1-propyl-1,7-dihydro-purin-6-one. | $^1$HNMR (400 MHz, DMSO d6): δ 0.93 (t, 8 Hz, 3H), 1.55 1.61 (m, 2H), 1.65-1.74 (m, 6H), 1.90-1.93 (m, 3H), 2.12 (m, 1H), 3.32 (d, 8 Hz, 3H), 4.11 (d, 8 Hz, 2H), 7.36 (d, 8 Hz, 1H), 7.63-7.69 (m, 1H), 8.38-8.43 (dd, 8 Hz, 1H) |
| 32 | 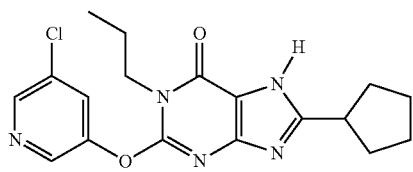 [SMILES: CCCn1c(Oc2cncc(Cl)c2)nc2nc(C3CCCC3)[nH]c2c1=O]<br>2-(5-Chloro-pyridin-3-yloxy)-8-cyclopentyl-1-propyl-1,7-dihydro purin-6-one. | $^1$HNMR (400 MHz, DMSO d6): δ 0.93 (t, 8 Hz, 3H), 1.56-1.59 (m, 2H), 1.66-1.73 (m, 2H), 3.10 (m, 1H), 4.08-4.11 (m, 2H), 8.14-8.21 (m, 1H), 8.58-8.63 (m, 1H), 13.02 (b.s, 1H) |
| 33 | 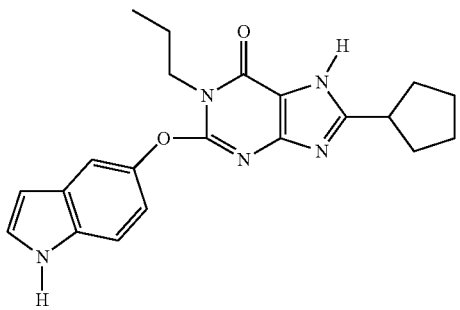 [SMILES: CCCn1c(Oc2ccc3[nH]ccc3c2)nc2nc(C3CCCC3)[nH]c2c1=O]<br>8-Cyclopentyl-2-(1H-indol-5-yloxy)-1-propyl-1,7-dihydro-purin-6-one. | $^1$HNMR (400 MHz, DMSO d6): δ 0.97 (t, 8 Hz, 3H), 1.57-1.581 (m, 8H), 1.90-1.95 (m, 2H), 3.00-3.10 (m, 1H), 4.12-4.17 (m, 2H), 6.45 (b.s, 1H), (td, 8 Hz, 4 Hz, 1H), 7.38 (b.s, 1H), 7.41-7.44 (m, 2H) |
| 34 | 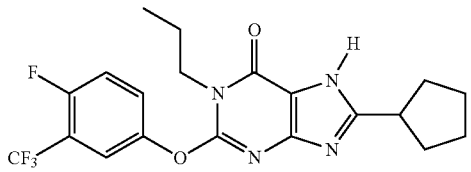 [SMILES: CCCn1c(Oc2ccc(F)c(C(F)(F)F)c2)nc2nc(C3CCCC3)[nH]c2c1=O]<br>8-Cyclopentyl-2-(4-fluoro-3-trifluoromethyl-phenoxy)-1-propyl-1,7-dihydro-purin-6-one. | $^1$HNMR (400 MHz, DMSO d6): δ 0.93 (t, 8 Hz, 3H), 1.56-1.58 (m, 2H), 1.61-1.77 (m, 6H), 1.91-1.95 (m, 2H), 3.01-3.12 (m, 1H), 4.06-4.11 (m, 2H), 7.62-7.67 (m, 1H), 7.71-7.79 (m, 1H), 7.83-7.93 (m, 1H). |
| 35 | 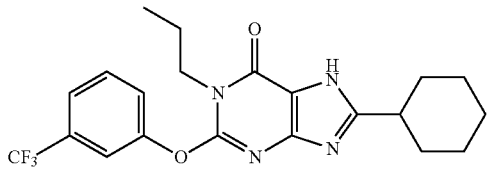 [SMILES: CCCn1c(Oc2cccc(C(F)(F)F)c2)nc2nc(C3CCCCC3)[nH]c2c1=O]<br>8-Cyclohexyl-1-propyl-2-(3-trifluoromethyl-phenoxy)-1,7-dihydro-purin-6-one. | 1HNMR (400 MHz, CD3OH): d 1.044 (t, J = 7.4 Hz, 3H); 1.24-2.098 (m, 12H); 2.678-2.809 (m, 1H); 4.16-4.322 (m, 2H); 7.585-7.717 (m, 4H). |

| Example No. | Structure and IUPAC name | NMR |
|---|---|---|
| 36 | 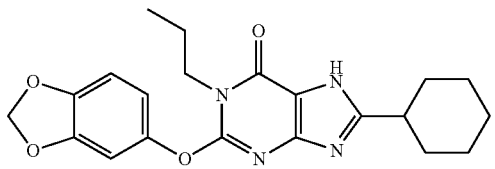 [SMILES: CCCn1c(Oc2ccc3c(c2)OCO3)nc2nc(C3CCCCC3)[nH]c2c1=O]<br>2-(Benzo[1,3]dioxol-5-yloxy)-8-cyclohexyl-1-propyl-1,7-dihydro-purin-6-one. | 1HNMR (400 MHz, CD3OD): d 1.025 (t, J = 7.4 Hz, 3H); 1.224-2.098 (m, 12H); 2.702-2.82 (m, 1H); 4.208 (t, J = 7.4 Hz, 2H); 6.001 (s, 2H); 6.63-6.710 (m, 1H); 6.764-6.88 (m, 2H). |
| 37 | 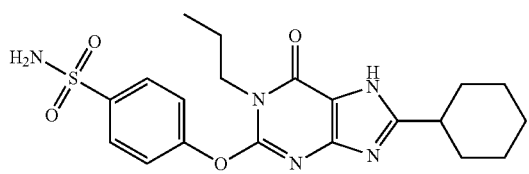 [SMILES: CCCn1c(Oc2ccc(S(N)(=O)=O)cc2)nc2nc(C3CCCCC3)[nH]c2c1=O]<br>4-(8-Cyclohexyl-6-oxo-1-propyl-6,7-dihydro-1H-purin-2-yloxy)-benzene sulfonamide. | 1HNMR (400 MHz, DMSO): d 0.930 (t, J = 7.2 Hz, 3H); 1.070-1.917 (m, 12H); 2.532-2.744 (m, 1H); 4.100 (t, J = 7.0 Hz, 2H); 7.364-7.556 (m, 4H); 7.86-7.94 (m, 2H); 12.7-13.02 (m, 1H). |
| 38 | 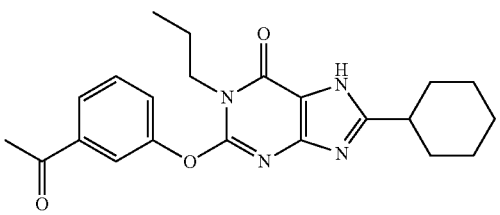 [SMILES: CCCn1c(Oc2cccc(C(C)=O)c2)nc2nc(C3CCCCC3)[nH]c2c1=O]<br>2-(3-Acetyl-phenoxy)-8-cyclohexyl-1-propyl-1,7-dihydro-purin-6-one. | 1HNMR (400 MHz, CD3OD): d 1.046 (t, J = 7.2 Hz, 3H); 1.176-1.997 (m, 12H); 2.619 (s, 3H); 2.703-2.81 (m, 1H); 4.258 (t, J = 7.2 Hz, 2H); 7.478-7.657 (m, 2H); 7.833-9.798 (m, 2H). |
| 39 | 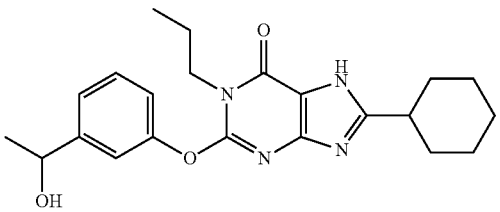 [SMILES: CCCn1c(Oc2cccc(C(C)O)c2)nc2nc(C3CCCCC3)[nH]c2c1=O]<br>8-Cyclohexyl-2-[3-(1-hydroxy-ethyl)-phenoxy]-1-propyl-1,7-dihydro-purin-6-one. | 1HNMR (400 MHz, CD3OD): d 1.036 (t, J = 7.4 Hz, 3H); 1.238-2.002 (m, 12H); 2.678-2.820 (m, 1H); 4.241 (t, J = 7.4 Hz, 2H); 4.82-4.872 (m, 1H); 7.09-7.147 (m, 1H); 7.225-7.312 (m, 2H); 7.36-7.432 (m, 1H). |
| 40 | 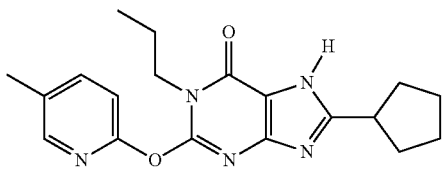 [SMILES: CCCn1c(Oc2ccc(C)cn2)nc2nc(C3CCCC3)[nH]c2c1=O]<br>8-Cyclopentyl-2-(5-methyl-pyridin-2-yloxy)-1-propyl-1,7-dihydro-purin-6-one. | $^1$HNMR (400 MHz, CD3OD): δ 1.02 (t, 8 Hz, 3H), 1.62-1.72 (m, 2H), 1.75-1.90 (m, 6H), 2.03-2.38 (m, 2H), 2.41 (s, 3H), 3.15-3.23 (m, 1H), 4.22 (t, 8 Hz, 3H), 7.22 (d, 8 Hz, 1H), 7.82 (dd, 8 Hz, 1H), 8.18 (b.s, 1H), |

| Example No. | Structure and IUPAC name | NMR |
|---|---|---|
| 41 | 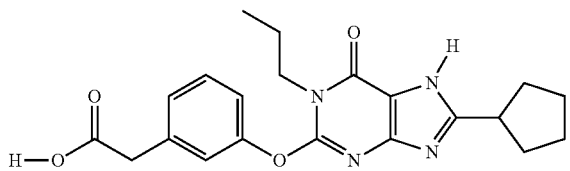 [SMILES: CCCn1c(Oc2cccc(CC(=O)O)c2)nc2nc(C3CCCC3)[nH]c2c1=O]<br>[3-(8-Cyclopentyl-6-oxo-1-propyl-6,7-dihydro-1H-purin-2-yloxy)-phenyl]-acetic acid. | $^1$HNMR (400 MHz, DMSO-d6): δ 0.95 (t, 8 Hz, 3H), 1.58-1.74 (m, 8H), 1.94 (d, 8 Hz, 2H), 3.01-3.11 (m, 1H), 3.63 (s, 2H), 4.11 (m, 2H), 7.15-7.21 (m, 3H), 7.39-7.43 (m, 1H), 12.96 (b.s, 1H) |
| 42 | 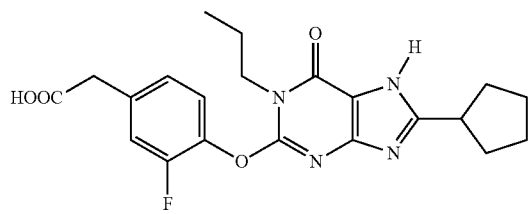 [SMILES: CCCn1c(Oc2ccc(CC(=O)O)cc2F)nc2nc(C3CCCC3)[nH]c2c1=O]<br>[4-(8-Cyclopentyl-6-oxo-1-propyl-6,7-dihydro-1H-purin-2-yloxy)-3-fluoro-phenyl]-acetic acid. | $^1$HNMR (400 MHz, DMSO d6): δ 0.94 (t, 8 Hz, 3H), 1.57-1.66 (m, 2H), 1.65-1.78 (m, 6H), 1.92-1.96 (m, 2H), 3.01-3.13 (m, 1H), 3.66 (s, 2H), 4.13 (t, 8 Hz, 2H), 7.18 (d, 8 Hz, 1H), 7.32-7.45 (m, 2H), |
| 43 | 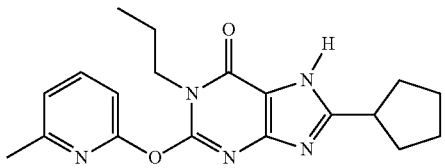 [SMILES: CCCn1c(Oc2cccc(C)n2)nc2nc(C3CCCC3)[nH]c2c1=O]<br>8-Cyclopentyl-2-(6-methyl-pyridin-2-yloxy)-1-propyl-1,7-dihydro-purin-6-one. | $^1$HNMR (400 MHz, CD3OD): δ 1.03 (t, 8 Hz, 3H), 1.68-1.77 (m, 6H), 2.04-2.10 (m, 2H), 2.5 (s, 3H), 3.15-3.23 (m, 1H), 4.22 (t, 8 Hz, 2H), 7.11 (d, 8 Hz, 1H), 7.26 (d, 8 Hz, 1H), 7.87 (t, 8 Hz, 1H), |
| 44 | 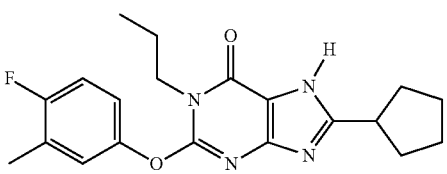 [SMILES: CCCn1c(Oc2ccc(F)c(C)c2)nc2nc(C3CCCC3)[nH]c2c1=O]<br>8-Cyclopentyl-2-(4-fluoro-3-methyl-phenoxy)-1-propyl-1,7-dihydro-purin-6-one. | $^1$HNMR (400 MHz, CD3OD): δ 1.03 (t, 8 Hz, 3H), 1.67 (m, 2H), 1.75-1.89 (m, 6H), 2.03-2.09 (m, 2H), 2.28 (s, 3H), 3.12-3.23 (m, 1H), 4.22 (t, 8 Hz, 2H), 7.03-7.15 (m, 3H), |
| 45 | 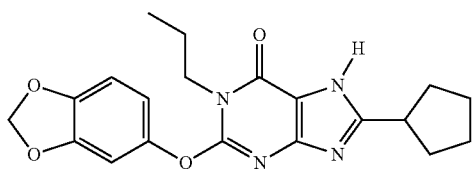 [SMILES: CCCn1c(Oc2ccc3c(c2)OCO3)nc2nc(C3CCCC3)[nH]c2c1=O]<br>2-(Benzo[1,3]dioxol-5-yloxy)-8-cyclopentyl-1-propyl-1,7-dihydro-purin-6-one. | $^1$HNMR (400 MHz,, CD3OD): δ 1.02 (t, 8 Hz, 3H), 1.66-1.72 (m, 2H), 1.75-1.88 (m, 6H), 2.03-2.09 (m, 2H), 3.17 (t, 8 Hz, 1H), 4.20 (t, 8 Hz, 2H), 5.99 (s, 2H), 6.68 (d, 8 Hz, 1H), 6.83 (t, 8 Hz, 2H), |

| Example No. | Structure and IUPAC name | NMR |
|---|---|---|
| 46 | 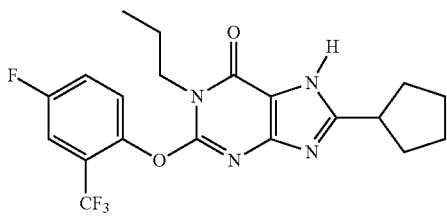 [SMILES: CCCn1c(Oc2ccc(F)cc2C(F)(F)F)nc2nc(C3CCCC3)[nH]c2c1=O]

8-Cyclopentyl-2-(2-fluoro-4-trifluoromethyl-phenoxy)-1-propyl-1,7-dihydro-purin-6-one. | $^1$HNMR (400 MHz, CD3OD): δ 1.02 (t, 8 Hz, 3H), 1.67-1.71 (m, 2H), 1.75-1.88 (m, 6H), 2.04-2.10 (m, 2H), 3.15-3.25 (m, 1H), 4.22 (t, 8 Hz, 2H), 7.49-7.60 (m, 3H), |
| 47 | 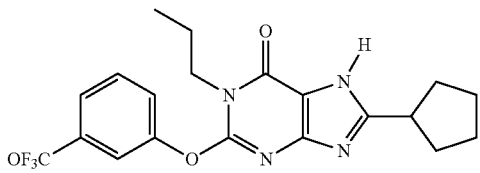

8-Cyclopentyl-1-propyl-2-(3-trifluoromethoxy-phenoxy)-1,7-dihydro-purin-6-one. | $^1$HNMR (400 MHz, CD3OD): δ 1.03 (t, 8 Hz, 3H), 1.66-1.667 (m, 2H), 1.75-1.90 (m, 6H), 2.03-2.08 (m, 2H), 3.16 (m, 1H), 4.23 (t, 8 Hz, 3H), 7.23-7.30 (m, 2H), 7.55 (t, 8 Hz, 1H) |
| 48 | 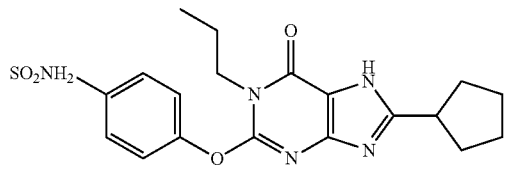 [SMILES: CCCn1c(Oc2ccc(S(N)(=O)=O)cc2)nc2nc(C3CCCC3)[nH]c2c1=O]

4-(8-Cyclopentyl-6-oxo-1-propyl-6,7-dihydro-1H-purin-2-yloxy)-benzenesulfonamide. | $^1$HNMR (400 MHz, DMSO d6): δ 0.95 (t, 8 Hz, 3H), 1.58 (m, 2H), 1.75 (m, 6H), 1.94 (m, 2H), 3.02-3.14 (m, 1H), 4.12 (m, 2H), 7.42-7.54 (m, 4H), 7.91-7.93 (m, 2H) |
| 49 | 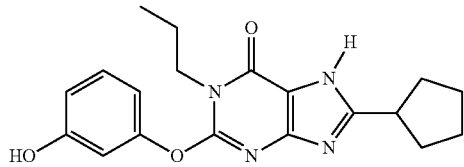

8-Cyclopentyl-2-(3-hydroxy-phenoxy)-1-propyl-1,7-dihydro-purin-6-one. | $^1$HNMR (400 MHz, DMSO d6): δ 0.93 (t, 8 Hz, 3H), 1.57-1.60 (m, 2H), 1.67-1.78 (m, 6H), 1.94 (m, 2H), 3.09 (m, 1H), 4.09 (t, 8 Hz, 2H), 6.65-6.72 (m, 3H), 7.21-7.25 (m, 1H), 9.9.5 (b.s, 1H), 12.93 (b.s, 1H), |
| 50 | 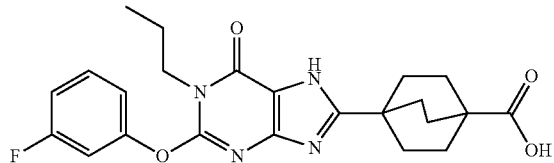 [SMILES: CCCn1c(Oc2cccc(F)c2)nc2nc(C34CCC(C(=O)O)(CC3)CC4)[nH]c2c1=O]

4-[2-(3-Fluoro-phenoxy)-6-oxo-1-propyl-6,7-dihydro-1H-purin-8-yl]-bicyclo[2.2.2]octane-1-carboxylic acid. | $^1$HNMR (400 MHz, CD3OD): δ 01.03 (t, J = 7.2 Hz, 3H); 1.82-1.91 (m, 14H); 4.23 (t, J = 8.4 Hz, 2H); 7.04-7.14 (m, 3H); 7.43-7.47 (m, 1H); |

| Example No. | Structure and IUPAC name | NMR |
|---|---|---|
| 51 | 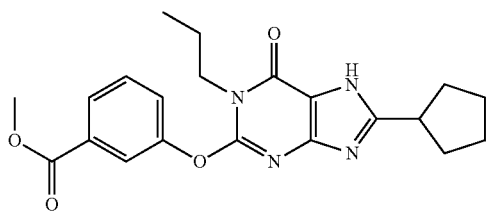 [SMILES: CCCn1c(Oc2cccc(C(=O)OC)c2)nc2nc(C3CCCC3)[nH]c2c1=O]<br>3-(8-Cyclopentyl-6-oxo-1-propyl-6,7-dihydro-1H-purin-2-yloxy)-benzoic acid methyl ester | $^1$HNMR (400 MHz, DMSO d6): δ 0.93 (t, J = 7.2 Hz, 3H), 1.54-1.74 (m, 8H), 1.90-1.92 (m, 2H), 3.04-3.08 (m, 1H), 3.85 (s, 3H), 4.10 (t, J = 7.2 Hz, 2H), 7.59-7.65 (m, 2H), 7.82 (br s, 1H), 7.88-7.90 (m, 1H), 12.9 (br s, 1H). (m + 1) = 397. |
| 52 | 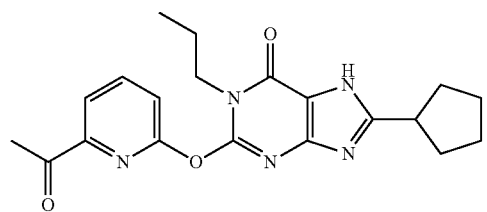 [SMILES: CCCn1c(Oc2cccc(C(C)=O)n2)nc2nc(C3CCCC3)[nH]c2c1=O]<br>2-(3-Acetyl-phenoxy)-8-cyclopentyl-1-propyl-1,7-dihydro-purin-6-one | $^1$HNMR (400 MHz, DMSO d6): δ 0.95 (t, J = 7.2 Hz, 3H), 1.55-1.79 (m, 8H), 1.90-1.95 (m, 2H), 2.60 (s, 1H), 4.13 (t, J = 7.2 Hz, 2H), 7.58-7.83 (m, 2H), 7.83 (s, 1H), 7.92 (d, J = 7.6 Hz, 1H), 12.86 (br s, 1H). (m + 1) = 381. |
| 53 | 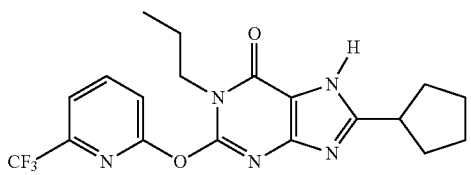<br>8-Cyclopentyl-1-propy)-2-(6-trifluoromethyl-pyridin-2-yloxy)-1,7-dihydro-purin-6-one | $^1$HNMR (400 MHz, DMSO d6): δ 0.94 (t, 8 Hz, 3H), 1.59-1.64 (m; 2H), 1.68-1.1.78 (m, 6H), 1.95-1.97 (m, 3H), 4.12 (t, 8 Hz, 3H), 7.75-7.82 (m, 1H), 7.94-7.97 (m, 1H), 8.32 (t, 8 Hz, 3H) |
| 54 | 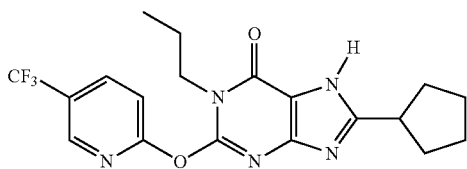 [SMILES: CCCn1c(Oc2ccc(C(F)(F)F)cn2)nc2nc(C3CCCC3)[nH]c2c1=O]<br>8-Cyclopentyl-1-propyl-2-(5-trifluoromethyl-pyridin-2-yloxy)-1,7-dihydro-purin-6-one | $^1$HNMR (400 MHz, DMSO d6): δ 0.75 (t, 8 Hz, 3H), 1.44-1.64 (m, 4H), 1.66-1.84 (m, 4H), 1.99-2.03 (m, 2H), 3.18-3.26 (m, 2H), 3.45-3.49 (m, 1H), 3.97-4.04 (m, 1H), 6.76 (d, 8 Hz, 1H), 7.91-7.95 (m, 1H), 13.42 (b.s, 1H), |
| 55 | 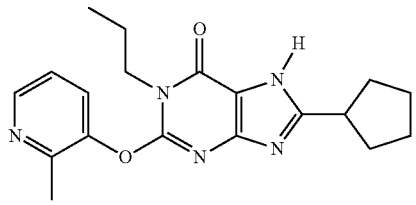 [SMILES: CCCn1c(Oc2cccnc2C)nc2nc(C3CCCC3)[nH]c2c1=O]<br>8-Cyclopentyl-2-(2-methyl-pyridin-3-yloxy)-1-propyl-1,7-dihydro-purin-6-one | $^1$HNMR (400 MHz, DMSO d6): δ 0.68 (t, 8 Hz, 3H), 1.30 (b.s, 2H), 1.40-1.50 (m, 6H), 1.65 (b.s, 2H), 2.08 (s, 3H), 2.80 (b.s, 1H), 3.87 (t, 8 Hz, 3H), 7.09 (t, 1H), 7.42 (b.s, 1H), 8.13 (b.s, 1H) |

-continued

| Example No. | Structure and IUPAC name | NMR |
|---|---|---|
| 56 | 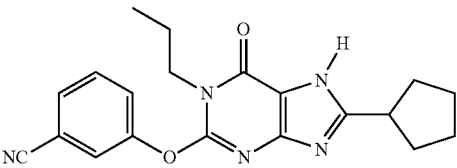 [SMILES: CCCn1c(Oc2cccc(C#N)c2)nc2nc(C3CCCC3)[nH]c2c1=O]<br>3-(8-Cyclopentyl-6-oxo-1-propyl-6,7-dihydro-1H-purin-2-yloxy)-benzonitrile | ¹HNMR (400 MHz, DMSO d6): 0.93 (t, 8 Hz, 3H), 1.55-1.60 (m, 2H), 1.70-1.78 (m, 6H), 1.92-1.93 (b.s, 2H), 3.08-3.10 (m, 1H), 4.09 (t, 8 Hz, 2H), 7.69 (d, 8 Hz, 2H), 7.79 (b.s, 1H), 7.90-7.96 (m, 1H), |
| 57 | 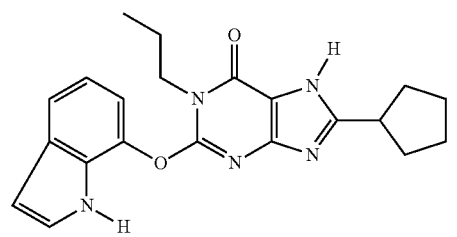 [SMILES: CCCn1c(Oc2cccc3cc[nH]c23)nc2nc(C3CCCC3)[nH]c2c1=O]<br>8-Cyclopentyl-2-(1H-indol-7-yloxy)-1-propyl-1,7-dihydro-purin-6-one | 1HNMR (400 MHz, DMSO d6): d 0.99 (t, J = 7.2 Hz, 3H); 1.56-1.91 (m, 11H); 2.99-3.11 (m, 1H); 4.17-4.22 (m, 2H); 6.50-6.53 (m, 1H); 6.94-7.05 (m, 2H); 7.35-7.37 (m, 1H); 7.48-7.51 (m, 1H); 11.25 (d, J = 41.2 Hz, 1H); 12.78 (d, J = 104.0 Hz, 1H) |
| 58 | 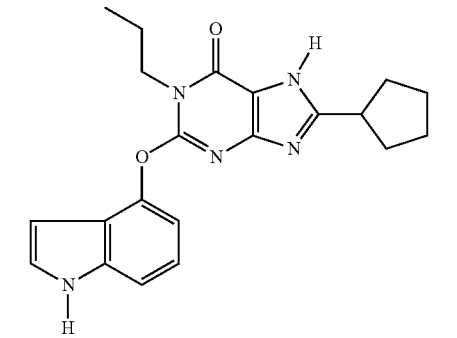 [SMILES: CCCn1c(Oc2cccc3[nH]ccc23)nc2nc(C3CCCC3)[nH]c2c1=O]<br>8-Cyclopentyl-2-(1H-indol-4-yloxy)-1-propyl-1,7-dihydro-purin-6-one | 1HNMR (400 MHz, DMSO d6): d 0.97 (t, J = 7.2 Hz, 3H); 1.52-1.92 (m, 11H); 2.96-3.09 (m, 1H); 4.16-4.20 (m, 2H); 6.19-6.23 (m, 1H); 6.85-6.90 (m, 1H); 7.09-7.13 (m, 1H); 7.31-7.35 (m, 1H); 11.35 (d, J = 8.0 Hz, 1H); 12.77 (d, J = 118.0 Hz, 1H) |
| 59 | 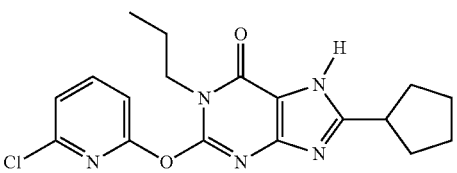 [SMILES: CCCn1c(Oc2cccc(Cl)n2)nc2nc(C3CCCC3)[nH]c2c1=O]<br>2-(6-Chloro-pyridin-2-yloxy)-8-cyclopentyl-1-propyl-1,7-dihydro-purin-6-one | ¹HNMR (400 MHz, DMSO d6): δ 0.93 (t, 8 Hz, 3H), 1.59-1.77 (m, 8H), 1.95 (b.s, 2H), 3.06-3.13 (m, 1H), 4.09 (t, 8 Hz, 2H), 7.41-7.48 (m, 2H), 7.57 (d, 8 Hz, 1H), 8.09 (t, 8 Hz, 2H), |
| 60 | 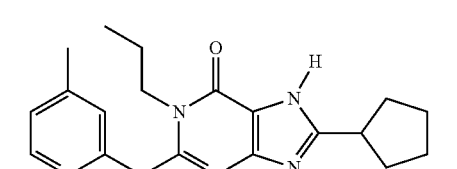<br>8-Cyclopentyl-2-(4-methyl-pyridin-2-yloxy)-1-propyl-1,7-dihydro-purin-6-one | ¹HNMR (400 MHz, DMSO d6): δ 7.42 (t, 8 Hz, 3H), 1.45-1.52 (m, 2H), 1.63-1.67 (m, 2H), 1.74-1.1.85 (m, 4H), 2.01 (m, 2H) 2.23 (s, 3H), 3.22 (t, 8 Hz, 2H), 6.32 (d, 8 Hz, 1H), 6.37 (s, 1H), 7.68-7.78 (m, 1H) |

| Example No. | Structure and IUPAC name | NMR |
|---|---|---|
| 61 | 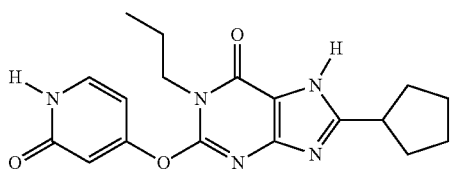 [SMILES: CCCn1c(Oc2cc[nH]c(=O)c2)nc2nc(C3CCCC3)[nH]c2c1=O]<br>8-Cyclopentyl-2-(2-oxo-1,2-dihydro-pyridin-4-yloxy)-1-propyl-1,7-dihydro-purin-6-one | $^1$HNMR (400 MHz, CD3OD): δ 1.008 (t, 8 Hz, 3H), 1.70-1.82 (m, 8H), 2.06-2.10 (m, 2H), 4.18 (t, 8 Hz, 2H), 6.42-6.46 (m, 2H), 7.52 (d, 8 Hz, 1H), |
| 62 | 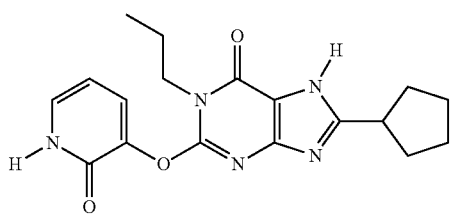 [SMILES: CCCn1c(Oc2ccc[nH]c2=O)nc2nc(C3CCCC3)[nH]c2c1=O]<br>8-Cyclopentyl-2-(2-oxo-1,2-dihydro-pyridin-3-yloxy)-1-propyl-1,7-dihydro-purin-6-one | $^1$HNMR (400 MHz, DMSO d6): δ 0.92 (t, 8 Hz, 3H), 1.58-1.60 (m, 2H), 1.68-1.79 (m, 6H), 1.93-1.96 (m, 2H), 4.06 (t, 8 Hz, 2H), 6.23-6.27 (m, 1H), 7.30-7.37 (m, 1H), 7.45-7.53 (m, 1H), 8.09 (s, 1H), 12.96 (b.s, 1H). |
| 63 | 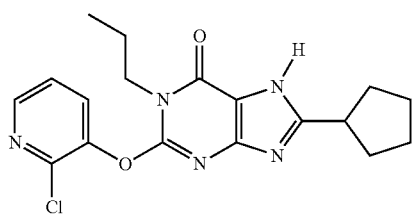 [SMILES: CCCn1c(Oc2cccnc2Cl)nc2nc(C3CCCC3)[nH]c2c1=O]<br>2-(2-Chloro-pyridin-3-yloxy)-8-cyclopentyl-1-propyl-1,7-dihydro-purin-6-one | $^1$HNMR (400 MHz, DMSO d6): δ 0.96 (t, 8 Hz, 3H), 1.57-1.63 (m, 2H), 1.67-1.84 (m, 6H), 1.92-1.99 (m, 2H), 3.02-3.14 (m, 1H), 4.15 (t, 8 Hz, 2H), 7.60-7.64 (m, 1H), 8.02-8.09 (m, 1H), 8.41-8.43 (t, 4 Hz, 1H) |
| 64 | 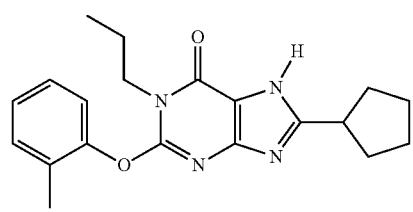 [SMILES: CCCn1c(Oc2ccccc2C)nc2nc(C3CCCC3)[nH]c2c1=O]<br>8-Cyclopentyl-1-propyl-2-o-tolyloxy-1,7-dihydro-purin-6-one | $^1$HNMR (400 MHz, DMSO d6): δ 0.96 (t, 8 Hz, 3H), 1.56-1.79 (m, 8H), 1.92-1.95 (t, 2H), 2.14 (s, 3H), 4.14 (t, 8 Hz, 2H), 7.19-7.31 (m, 3H), 7.34-7.36 (d, 8 Hz, 1H), 12.93 (b.s, 1H) |
| 65 | 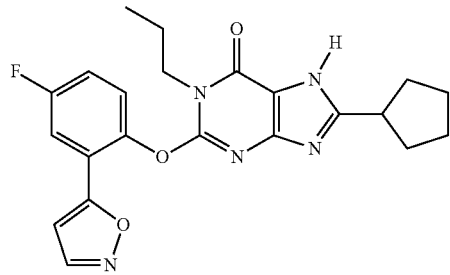 [SMILES: CCCn1c(Oc2ccc(F)cc2-c2ccno2)nc2nc(C3CCCC3)[nH]c2c1=O]<br>8-Cyclopentyl-2-(4-fluoro-2-isoxazol-5-yl-phenoxy)-1-propyl-1,7-dihydro-purin-6-one | $^1$HNMR (400 MHz, DMSO d6): δ 0.74 (t, J = 8 Hz, 3H), 1.45-1.53 (m, 2H), 1.63 (d, 8 Hz, 2H), 1.75-1.90 (m, 4H), 2.01 (d, 8 Hz, 2H), 3.16-3.13 (m, 1H), 3.62-3.66 (t, 8 Hz, 1H), 4.02-4.09 (m, 1H), 7.55-7.59 (m, 2H), 7.60-7.66 (m, 1H), 7.90-7.95 (d, 20 Hz, 2H), 13.07 (b.s, 1H) |

| Example No. | Structure and IUPAC name | NMR |
|---|---|---|
| 66 | 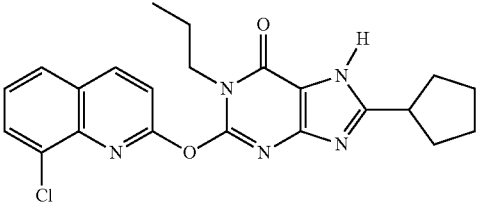 [SMILES: CCCn1c(Oc2ccc3cccc(Cl)c3n2)nc2nc(C3CCCC3)[nH]c2c1=O]<br>2-(8-Chloroquinolin-2-yloxy)-8-cyclopentyl-1-propyl-1,7-dihydro-purin-6-one | $^1$HNMR (400 MHz, DMSO d6): δ 0.98 (t, 7.2 Hz, 3H), 1.56-1.76 (m, 8H), 1.96 (t, 4 Hz, 2H), 3.06-3.15 (m, 1H), 4.16 (t, J = 8 Hz, 2H), 7.63-7.71 (m, 2H), 8.00-8.02 (d, J = 8 Hz, 1H), 8.08 (t, J = 8 Hz), 8.65-8.69 (m, 1H), |
| 67 | 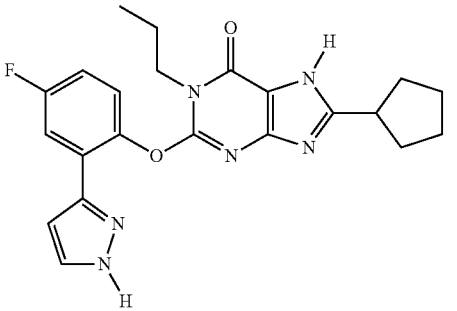 [SMILES: CCCn1c(Oc2ccc(F)cc2-c2cc[nH]n2)nc2nc(C3CCCC3)[nH]c2c1=O]<br>8-Cyclopentyl-2-[4-fluoro-2-(1H-pyrazol-3-yl)-phenoxy]-1-propyl-1,7-dihydro-purin-6-one | $^1$HNMR (400 MHz, DMSO d6): δ 0.9 (t, 7.6 Hz, 3H), 1.54-1.92 (m, 2H), 1.91 ( d, J = 8 Hz, 2H), 2.33 (b.s, 1H), 4.15 (t, 8 Hz, 2H), 6.53 (s, 1H), 7.27 (t, J = 4 Hz, 1H), 7.39 (s, 1H), 7.69-7.72 (m, 1H), 13.06 (b.s, 1H), |
| 68 | 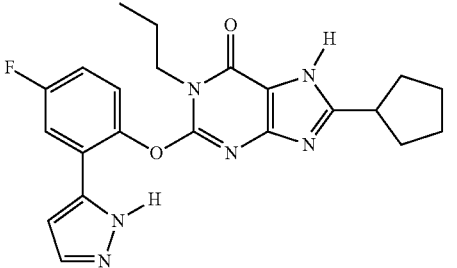 [SMILES: CCCn1c(Oc2ccc(F)cc2-c2ccn[nH]2)nc2nc(C3CCCC3)[nH]c2c1=O]<br>8-Cyclopentyl-2-[4-fluoro-2-(2H-pyrazol-3-yl)-phenoxy]-1-propyl-1,7-dihydro-purin-6-one | $^1$HNMR (400 MHz, DMSO d6): δ 0.75 (t, 8 Hz, 3H), 1.62-1.87 (m, 8H), 1.99-2.05 (m, 2H), 3.20-3.24 (m, 1H), 4.02 (t, 8 Hz, 2H), 6.96-7.00 (m, 1H), 7.06-7.18 (m, 1H), 7.19-7.64 (m, 1H), 8.37 (s, 1H), 10.12 (b.s, 1H) |
| 69 | 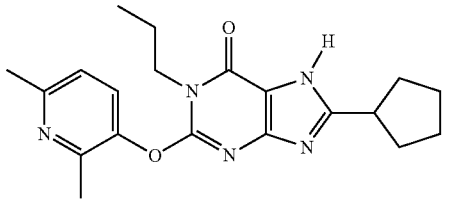 [SMILES: CCCn1c(Oc2ccc(C)nc2C)nc2nc(C3CCCC3)[nH]c2c1=O]<br>8-Cyclopentyl-2-(2,6-dimethyl-pyridin-3-yloxy)-1-propyl-1,7-dihydro-purin-6-one | $^1$HNMR (400 MHz, DMSO d6): δ 0.96 (t, J = 8 Hz, 3H), 1.56-1.62 (m, 2H), 1.70-1.77 (m, 6H), 1.93 (b.s, 2H), 2.30 (s, 3H), 2.5000-2.5008 (t, J = 1.6 Hz, 3H), 3.03-3.10 (m, 1H), 4.13 (t, 8 Hz, 2H), 7.20 (d, J = 8 Hz, 1H), 7.53-7.59 (m, 1H), 12.99 (s, 1H) |

Example 70

8-Cyclopentyl-2-[3-(1-hydroxy-ethyl)-phenoxy]-1-propyl-1,7-dihydro-purin-6-one

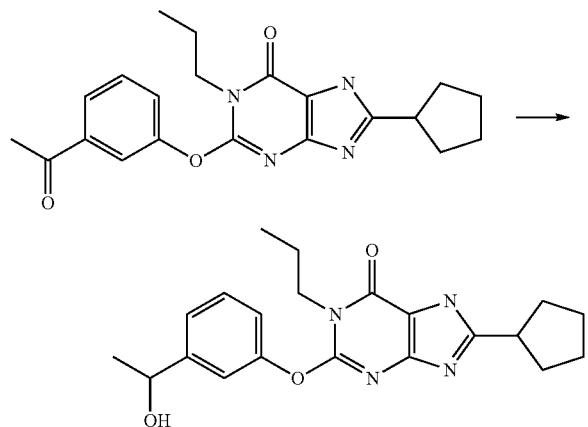

2-(3-Acetyl-phenoxy)-8-cyclopentyl-1-propyl-1,7-dihydro-purin-6-one (0.05 g, 0.178 mmol) was taken in ethanol (2 ml). To this was added NaBH$_4$ (0.02 mg, 0.525 mmol) at 0° C. and stirred at room temperature for 2 hours. The reaction mixture was quenched with saturated NH$_4$Cl and solvent was concentrated under reduced pressure. Aqueous layer was extracted with ethyl acetate and organic layer was washed with brine, dried over Na$_2$SO$_4$ and concentrated under reduced pressure. The residue was purified by preparative HPLC using 1% methanol in dichloromethane as solvent system to give the product as off white solid (0.04 g) in 85% yield.

$^1$HNMR (400 MHz, DMSO d6): δ 0.95 (t, J=7.2 Hz, 3H), 1.31 (d, J=6.4 Hz, 2H), 1.54-1.60 (m, 2H), 1.64-1.90 (m, 6H), 1.92-1.93 (m, 2H), 3.03-3.07 (m, 1H), 4.09 (t, J=7.2 Hz, 2H), 4.72-4.75 (m, 1H), 5.27 (d, J=4 Hz, 1H), 7.11 (d, J=7.6 Hz, 1H), 7.20 (s, 1H), 7.25 (d, J=8.0 Hz, 1H), 7.38 (t, J=7.6 Hz, 1H), 12.8 (br s, 1H).

(m+1)=383.

Example 71

8-Cyclopentyl-2-[3-(1-hydroxy-1-methyl-ethyl)-phenoxy]-1-propyl-1,7-dihydro-purin-6-one

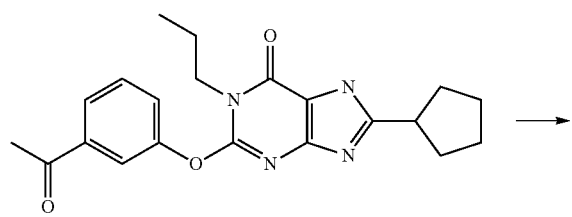

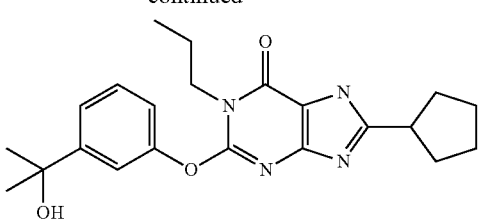

2-(3-Acetyl-phenoxy)-8-cyclopentyl-1-propyl-1,7-dihydro-purin-6-one (0.08 g, 0.21 mmol), was taken in THF. To this was added methyl magnesium bromide (30 μl, 0.25 mmol) drop wise at −70° C. and stirred for 2 hours. Another lot of methyl magnesium bromide (30 μl, 0.25 mmol) was added and stirred further for 2 hours. Reaction was quenched with saturated NH$_4$Cl solution and concentrated to evaporate THF and residue was dissolved in ethyl acetate, washed with water followed by brine and dried over anhydrous Na$_2$SO$_4$. The crude product was purified by preparative TLC to give the product (0.027 g) as an off white solid in 32% yield.

$^1$HNMR (400 MHz, DMSO d6): δ 0.95 (t, J=7.6 Hz, 3H), 1.43 (s, 6H), 1.56-1.62 (m, 2H), 1.68-1.77 (m, 6H), 1.92-1.95 (m, 2H), 3.05-3.10 (m, 1H), 4.11 (t, J=6.8 Hz, 2H), 5.15 (s, 1H), 7.11-7.16 (m, 1H), 7.33 (s, 1H), 7.37-7.41 (m, 2H) 12.8 (br s, 1H).

(m+1)=397.

Example 72

8-Cyclopentyl-1-isobutyl-2-(2-methyl-pyridin-3-yloxy)-1,7-dihydro-purin-6-one

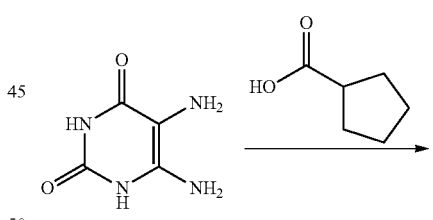

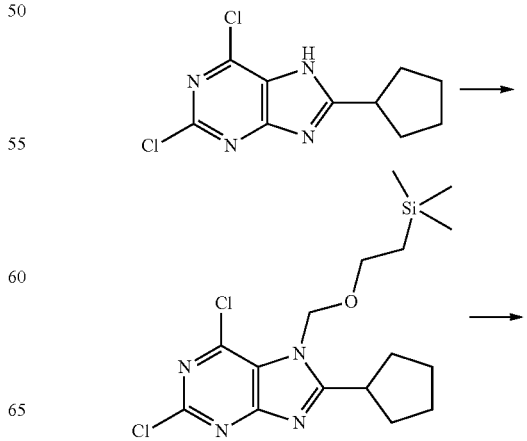

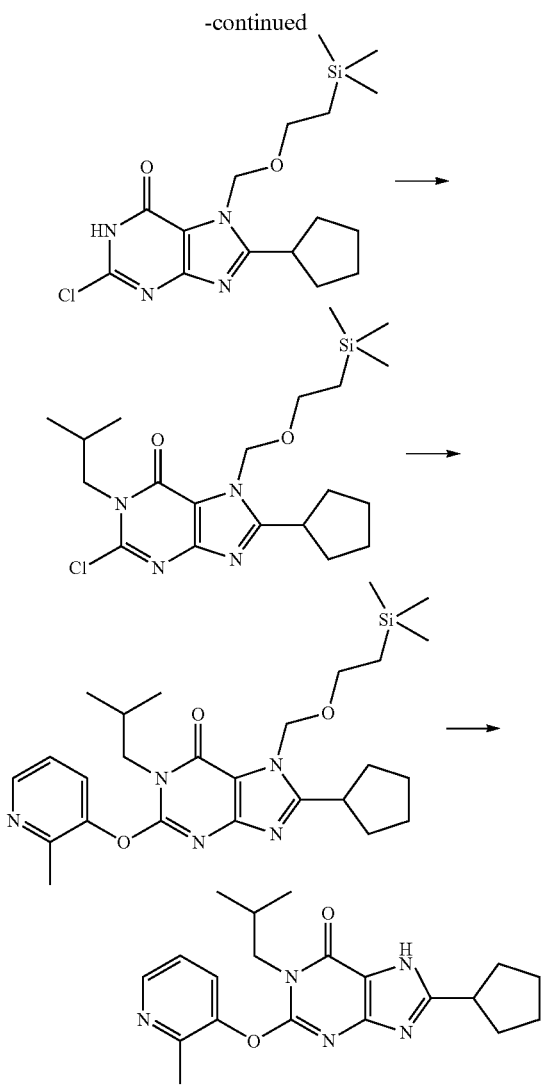

Step 1: 2,6-Dichloro-8-cyclopentyl-7H-purine

A mixture of 5,6-diamino-1H-pyrimidine-2,4-dione sulphate (10 g, 70.42 mmol) and cyclopentanecarboxylic acid (8.02 g, 70.42 mmol) was taken in POCl$_3$ and stirred at reflux temperature for 3 days under inert conditions. Reaction mixture was concentrated and quenched with water and extracted with ethyl acetate. Ethyl acetate layer was washed with brine and water, dried over anhydrous sodium sulphate and concentrated. Residue obtained was purified by coloumn chromatography to provide 2,6-dichloro-8-cyclopentyl-7H-purine (3.5 g, 20%) as brown solid.

$^1$HNMR (400 MHz, CDCl3): δ 1.25-1.81 (m, 2H); 1.85-1.93 (m, 2H); 1.98-2.07 (m, 2H); 2.20-2.25 (m, 2H); 3.42-3.45 (m, 1H); 11.50 (s, 1H).

Step 2: 2,6-Dichloro-8-cyclopentyl-7-(2-trimethylsilanyl-ethoxymethyl)-7H-purine A mixture 2,6-dichloro-8-cyclopentyl-7H-purine (0.2 g, 0.78 mmol) and potassium carbonate (0.32 g, 2.34 mmol) was taken in DMF (2.5 ml) and 2-(trimethylsilyl)ethoxymethyl chloride (0.38 g, 2.34 mmol) was added drop wise. The reaction mixture was stirred at room temperature for 4 hours, diluted with water (10 ml). The aqueous layer was extracted with ethyl acetate. The organic layer was washed with saturated brine solution and dried over Na$_2$SO$_4$ and concentrated. The residue was purified by column chromatography to obtain 2,6-dichloro-8-cyclopentyl-7-(2-trimethylsilanyl-ethoxymethyl)-7H-purine (0.12 g, 40%) as yellow oil.

$^1$HNMR (400 MHz, CDCl3): δ −0.004-(−0.01) (m, 9H); 0.9-0.97 (m, 2H); 1.75-1.80 (m, 2H); 1.96-2.0 (m, 2H); 2.04-2.15 (m, 2H); 3.40-3.44 (m, 1H); 3.56-3.66 (m, 2); 5.6 (s, 2H).

Step 3: 2-Chloro-8-cyclopentyl-7-(2-trimethylsilanyl-ethoxymethyl)-1,7-dihydro-purin-6-one To a solution of 2,6-dichloro-8-cyclopentyl-7-(2-trimethylsilanyl-ethoxymethyl)-7H-purine (0.12 g, 0.31 mmol) in dioxane (5 ml) was added aqueous solution of sodium carbonate (0.012 g, 1.24 mmol, in 4 ml water). Reaction mixture was refluxed overnight. Reaction mixture was concentrated and water was added in it and it was extracted with ethyl acetate. Ethyl acetate layer was washed with brine and water, dried over sodium sulphate, filtered and concentrated. Residue obtained was washed with ether to obtained 2-chloro-8-cyclopentyl-7-(2-trimethylsilanyl-ethoxymethyl)-1,7-dihydro-purin-6-one (0.1 g, 87%) as white solid.

$^1$HNMR (400 MHz, CDCl$_3$): δ −0.12-(−0.02) (m, 9H); 0.79-0.87 (m, 2H); 1.56-1.59 (m, 2H); 1.70-184 (m, 4H); 1.91-1.92 (m, 2H); 3.20-3.24 (m, 1H); 3.45-3.57 (m, 2); 5.28 (s, 2H).

Step 4: 2-Chloro-8-cyclopentyl-1-isobutyl-7-(2-trimethylsilanyl-ethoxymethyl)-1,7-dihydro-purin-6-one A mixture 2-chloro-8-cyclopentyl-7-(2-trimethylsilanyl-ethoxymethyl)-1,7-dihydro-purin-6-one (0.1 g, 0.27 mmol) and cesium carbonate (0.1 g, 0.30 mmol) was taken in DMF (2 ml) and isobutyl bromide (0.055 g, 0.41 mmol) was added drop wise. The reaction mixture was stirred and heated at 60° C. overnight, diluted with water (10 ml). The aqueous layer was extracted with ethyl acetate. The organic layer was washed with saturated brine solution, dried over sodium sulphate and concentrated. The residue was purified by column chromatography to provide 2-chloro-8-cyclopentyl-1-isobutyl-7-(2-trimethylsilanyl-ethoxymethyl)-1,7-dihydro-purin-6-one (0.08 g, 69%) as yellow oil.

$^1$HNMR (400 MHz, CDCl3): δ −0.037-0.00 (m, 9H); 0.82-0.93 (m, 2H); 1.04-1.06 (d, J=8 Hz, 6H); 1.70-1.72 (m, 2H); 1.88-1.91 (m, 2H); 2.03-2.12 (m, 4H); 2.25-2.29 (m, 1H); 3.33-3.42 (m, 1H); 3.54-3.58 (m, 2); 4.36-4.37 (d, J=6.8 Hz, 2H) 5.56 (s, 2H).

Step 5: 8-Cyclopentyl-1-isobutyl-2-(2-methyl-pyridin-3-yloxy)-7-(2-trimethylsilanyl-ethoxymethyl)-1,7-dihydro-purin-6-one A mixture of 2-chloro-8-cyclopentyl-1-isobutyl-7-(2-trimethylsilanyl-ethoxymethyl)-1,7-dihydro-purin-6-one (0.11 g, 0.259 mmol), N-methylpyrrolidine (1 ml), potassium carbonate (0.11 g, 0.778 mmol) and 2-methyl 3-hydroxy pyridine (0.034 g, 0.31 mmol), was heated at 85-90° C. overnight. Reaction mixture was cooled room temperature, diluted with water (10 ml), extracted with ethyl acetate. The ethyl acetate layer was washed with brine and water, dried over sodium sulphate, filtered and concentrated to obtain 8-cyclopentyl-1-isobutyl-2-(2-methyl-pyridin-3-yloxy)-7-(2-trimethylsilanyl-ethoxymethyl)-1,7-dihydro-purin-6-one (0.11 g, 75%) as crude oil.

Step 6: Preparation of 8-Cyclopentyl-1-isobutyl-2-(2-methyl-pyridin-3-yloxy)-1,7-dihydro-purin-6-one A mixture of 8-cyclopentyl-1-isobutyl-2-(2-methyl-pyridin-3-yloxy)-7-(2-trimethylsilanyl-ethoxymethyl)-1,7-dihydro-purin-6-one (0.11 g, 0.214 mmol), 2N HCl (2.5 ml), ethanol (2.5 ml) was heated at 85° C. for 4 hours. The mixture was cooled and the solvent was evaporated. The residue was diluted with water (10 ml). The aqueous layer was extracted with ethyl acetate. The organic layer was washed with saturated brine solution, dried over sodium sulphate and concentrated. The residue was purified by column chromatography to provide 8-Cyclopentyl-1-isobutyl-2-(2-methyl-pyridin-3-yloxy)-1,7-dihydro-purin-6-one (0.01 g) as white solid.

$^1$HNMR (400 MHz, CDCl$_3$): δ 0.95-0.97 (d, J=8 Hz, 6H); 1.60-1.82 (m, 6H); 1.98-2.08 (m, 3H); 2.07-2.10 (m, 1H); 2.30 (s, 3H); 3.12-3.16 (m, 1H); 3.64 (s, 3H); 4.18-4.20 (d, J=8 Hz, 2H); 7.30-7.34 (m, 1H); 7.54-7.61 (m, 1H); 8.34-8.35 (m, 1H); 12.99 (s, 1H).

Example 73

8-Cyclopentyl-2-methoxy-1-propyl-1,7-dihydro-purin-6-one

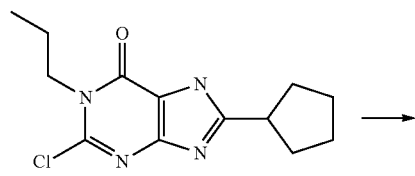

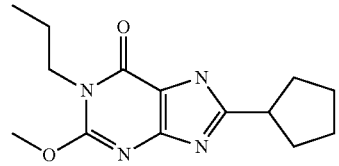

To a solution of 8-cyclopentyl-2-chloro-1-propyl-1,7-dihydro-purin-6-one (0.06 g, 0.21 mmol) in methanol (2 ml) was added NaH (60% dispersion in mineral oil, 0.085 g, 2.14 mmol) under nitrogen atmosphere and the reaction mixture was refluxed for 3 hours. After cooling to room temperature the reaction mixture was concentrated under reduced pressure. Water (10 ml) was added to the residue and the product was extracted with ethyl acetate. The organic layer was dried over anhydrous sodium sulphate and concentrated under vacuum. The crude product was purified by preparative TLC using 2% methanol in dichloromethane as solvent system to give the product (0.013 g, 22%) as a white solid.

$^1$HNMR (400 MHz, DMSO d6): δ 0.85-0.89 (m, 3H), 1.58-1.62 (br. s, 4H), 1.72-1.84 (br. d, 4H), 1.97 (br. s, 2H), 3.11 (m, 1H), 3.96 (br. s, 2H), 3.97 (s, 3H).

Examples 74 to 88 were prepared following the experimental procedure as given for Example 73.

| Example No. | Structure and IUPAC name | NMR |
|---|---|---|
| 74 | 8-Cyclopentyl-2-ethoxy-1-propyl-1,7-dihydro-purin-6-one. | $^1$HNMR (400 MHz, DMSO-d6): δ 0.87 (b.s, 3H), 1.24 (b.s, 2H), 1.37 (b.s, 3H), 1.61 (b.s, 4H), 1.74-1.82 (m, 3H), 1.98 (b.s, 2H), 3.10-3.14 (m, 1H), 3.94 (b.s, 2H), 4.41-4.43 (m, 2H), |
| 75 | 8-Cyclopentyl-2-cyclopentyloxy-1-propyl-1,7-dihydro-purin-6-one. | $^1$HNMR (400 MHz, CD3OD): δ 0.94 (t, 8 Hz, 3H), 1.64-2.11 (m, 18H), '3.12-3.35 (m, 2H), 3.99-4.03 (m, 2H), |
| 76 | 8-Cyclopentyl-2-cyclopentyloxy-1-propyl-1,7-dihydro-purin-6-one. | 1HNMR (400 MHz, DMSO d6): d 0.838 (t, J = 7.6 Hz 3H); 1.208-1.972 (m, 20H); 2.589-2.770 (m, 1H); 3.790-3.968 (m, 2H); 5.35-5.44 (m, 1H); 12.56-12.82 (m, 1H). |

| Example No. | Structure and IUPAC name | NMR |
|---|---|---|
| 77 | 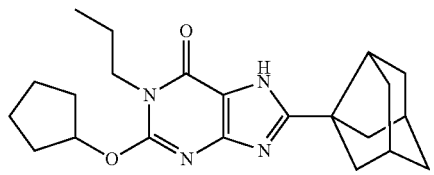<br>2-Cyclopentyloxy-8-(hexahydro-2,5-methano-pentalen-3a-yl)-1-propyl-1,7-dihydro-purin-6-one. | $^1$HNMR (400 MHz, CD3OD): δ 0.95 (t, 8 Hz, 3H), 1.63-1.86 (m, 11H), 1.93-2.03 (m, 8H), 2.16-2.19 (m, 2H), 2.36 (m, 2H), 2.70 (m, 1H), 4.02 (t, 8 Hz, 2H), |
| 78 | 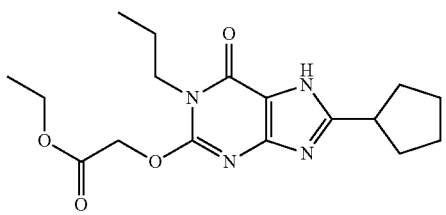<br>(8-Cyclopentyl-6-oxo-1-propyl-6,7-dihydro-1H-purin-2-yloxy)-acetic acid ethyl ester. | $^1$HNMR (400 MHz, DMSO-d6): δ 0.87 (t, 8 Hz, 3H), 1.62-1.82 (m, 8H), 1.97 (b.s, 2H), 3.14 (b.s, 1H), 3.71 (s, 1H), 3.97-4.01 (t, 8 Hz, 3H), 4.14-4.19 (m, 2H), 5.05 (b.s, 2H), |
| 79 | 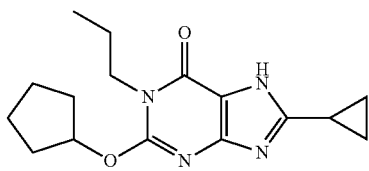<br>2-Cyclopentyloxy-8-cyclopropyl-1-propyl-1,7-dihydro-purin-6-one. | (400 MHz, DMSO) 0.63 (t, J = 7.6 Hz, 3H); 1.05-1.10 (m, 4H); 1.63-2.03 (m, 11H); 4.01 (t, J = 8.0 Hz, 2H); 5.51-5.62 (m, 1H) |
| 80 | 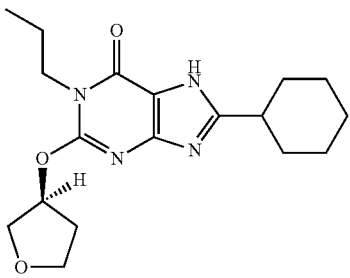<br>8-Cyclohexyl-1-propyl-2-[(R)-(tetrahydro-furan-3-yl)oxy]-1,7-dihydro-purin-6-one. | 1HNMR (400 MHz, CD3OD): d 0.945(t, J = 7.4 Hz, 3H); 1.234-2.40 (m, 12H); 2.157-2.41(m, 2H); 2.72-2.87(m, 1H); 3.85-4.12(m, 6H); 5.62-5.7(m, 1H) |
| 81 | 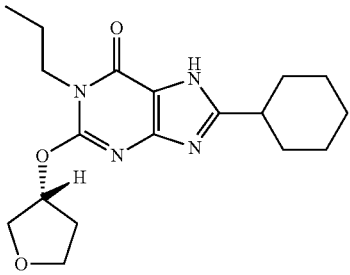<br>8-Cyclohexyl-1-propyl-2-[(S)-(tetrahydro-furan-3-yl)oxy]-1,7-dihydro-purin-6-one. | 1HNMR (400 MHz, CD3OD): d 0.945(t, J = 7.4 Hz, 3H); 1.234-2.40 (m, 12H); 2.157-2.41(m, 2H); 2.72-2.87(m, 1H); 3.85-4.12(m, 6H); 5.62-5.7(m, 1H) |

| Example No. | Structure and IUPAC name | NMR |
|---|---|---|
| 82 | 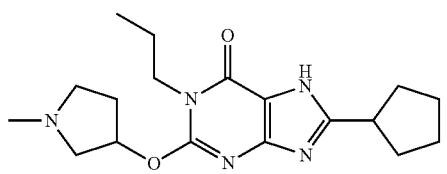<br>8-Cyclopentyl-2-(1-methyl-pyrrolidin-3-yloxy)-1-propyl-1,7-dihydro-purin-6-one. | $^1$HNMR (400 MHz, DMSO d6): δ 0.92 (t, J = 7.2 Hz, 3H), 1.58-1.85 (m, 9H), 1.94-2.02 (m, 3H), 2.39-2.42 (m, 1H), 2.77 (s, 3H), 3.12-3.18 (m, 1H), 3.34-3.53 (m, 3H), 4.15-4.23 (m, 3H), 12.9 (br s, 1H). (m + 1) = 346. |
| 83 | 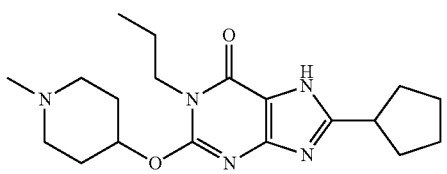<br>8-Cyclopentyl-2-(1-methyl-piperidin-4-yloxy)-1-propyl-1,7-dihydro-purin-6-one. | $^1$HNMR (400 MHz, DMSO d6): δ 0.89 (t, J = 7.2 Hz, 3H), 1.60-1.62 (m, 2H), 1.68-1.86 (m, 9H), 1.94-2.25 (m, 2H), 2.16-2.26 (m, 1H), 2.62-2.73 (m, 1H), 2.83 (s, 3H), 3.18-3.18 (m, 2H), 3.30-3.33 (m, 3H), 4.95-4.05 (m, 1H), 4.3-4.4 (m, 1H), 13.0 (br s, 1H). (m + 1) = 360. |
| 84 | 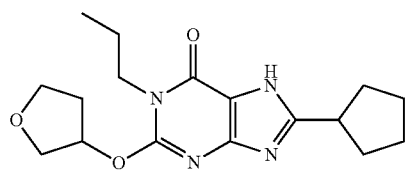<br>8-Cyclopentyl-1-propyl-2-(tetrahydro-furan-3-yloxy)-1,7-dihydro-purin-6-one. | $^1$HNMR (400 MHz, DMSO d6): δ 0.83 (t, J = 7.2 Hz, 3H), 1.52-1.59 (m, 4H), 1.69-1.78 (m, 4H), 1.94-1.96 (m, 2H), 2.05-2.12 (m, 1H), 2.17-2.25 (m, 1H), 3.04-3.15 (m, 1H), 3.78-3.92 (m, 6H), 5.51-5.52 (m, 1H). (m + 1) = 333. |
| 85 | 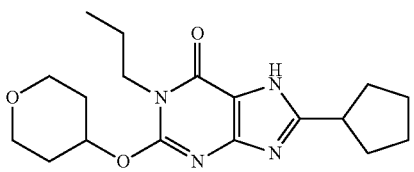<br>8-Cyclopentyl-1-propyl-2-(tetrahydro-pyran-4-yloxy)-1,7-dihydro-purin-6-one. | $^1$HNMR (400 MHz, DMSO d6): δ 0.86 (t, J = 7.6 Hz, 3H), 1.21-1.81 (m, 10H), 1.93-2.03 (m, 4H), 3.05-3.11 (m, 1H), 3.51-3.56 (m, 2H), 3.77-3.82 (m, 2H), 3.93(t, J = 6.8 Hz, 2H), 5.20-5.22 (m, 1H), 12.8 (br s, 1H). (m + 1) = 346. |
| 86 | 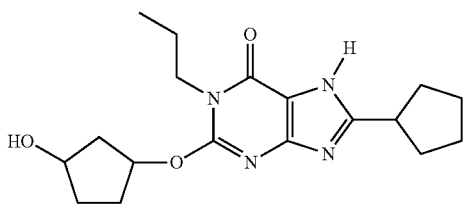<br>8-Cyclopentyl-2-(3-hydroxy-cyclopentyloxy)-1-propyl-1,7-dihydro-purin-6-one | 1HNMR (400 MHz, DMSO d6): d 0.83 (t, J = 7.2 Hz, 3H); 1.21 (s, 2H); 1.51-1.61 (m, 4H); 1.70-1.81 (m, 4H); 1.87-1.96 (m, 4H); 2.12-2.20 (m, 1H); 3.02-3.12 (m, 1H); 3.84-3.93 (m, 2H); 4.26-4.28 (m, 1H); 4.65-4.69 (m, 1H); 5.40-5.44 (m, 1H); 12.70 (m, 1H) |

| Example No. | Structure and IUPAC name | NMR |
|---|---|---|
| 87 | 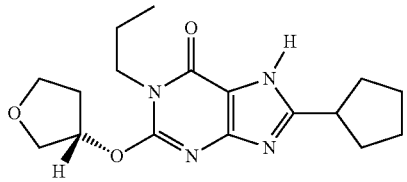<br>8-Cyclopentyl-1-propyl-2-[(S)-(tetrahydro-furan-3-yl)oxy]-1,7-dihydro-purin-6-one | $^1$HNMR (400 MHz, DMSO d6): δ 0.83 (t, 8 Hz, 3H), 1.53-1.80 (m, 8H), 1.94-2.48 (m, 5H), 3.07-3.11 (m, 1H), 3.78-3.91 (m, 5H), 5.51 (b.s, 1H), |
| 88 | 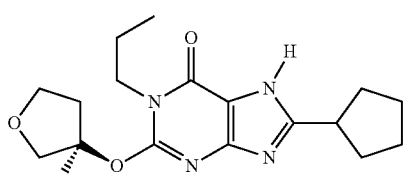<br>8-Cyclopentyl-1-propyl-2-[(R)-(tetrahydro-furan-3-yl)oxy]-1,7-dihydro-purin-6-one | $^1$HNMR (400 MHz, CD3OD): δ 0.85 (t, 8 Hz, 3H), 1.22-1.25 (m, 3H), 1.55-1.64 (m, 3H), 1.70-1.82 (m, 3H), 1.93-2.00 (m, 2H), 2.08-2.13 (m, 1H), 2.21-2.27 (m, 1H), 3.11 (m, 1H), 3.79-3.93 (m, 5H), 5.52-5.54 (m, 1H), |

Example 89

8-Adamantan-1-yl-2-(2-hydroxy-ethylamino)-1-propyl-1,7-dihydro-purin-6-one

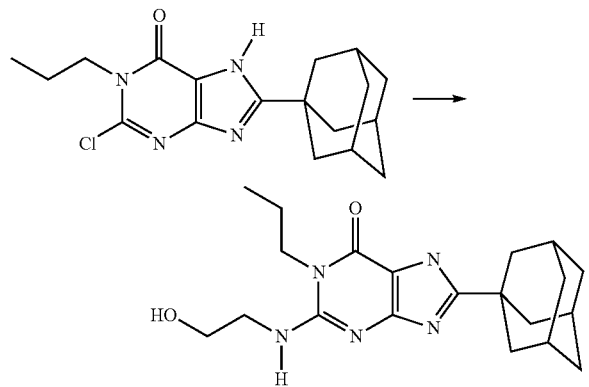

To a solution of 8-adamantan-2-yl-2-chloro-1-propyl-1,7-dihydro-purin-6-one (0.06 g, 0.17 mmol) in N-methyl-2-pyrrolidone (0.2 ml) was added ethanol amine followed by diisopropylethylamine (0.07 g, 0.52 mmol) and the reaction mixture was heated at 130° C. for 2 hours. The reaction mixture was then diluted with water and extracted with ethyl acetate. Ethyl acetate layer was dried over anhydrous sodium sulphate and concentrated under vacuum. The crude product was purified by preparative TLC using 2% methanol in dichloromethane as the solvent system to give the desired product (0.01 g, 15%) as an off-white solid.

$^1$HNMR (400 MHz, DMSO d6): δ 0.88 (t, J=8 Hz, 3H), 1.54 (br.s, 2H), 1.71 (br.s, 6H), 1.92-2.01 (m, 9H), 3.38 (br. s, 2H), 3.56 (br. s, 2H), 3.9 (br. s, 2H), 4.85 (s, 1H), 6.85 (s, 1H), 12.12 (s, 1H).

Examples 90 to 107 were prepared following the experimental procedure as given for Example 89.

| Example No. | Structure and IUPAC name | NMR |
|---|---|---|
| 90 | 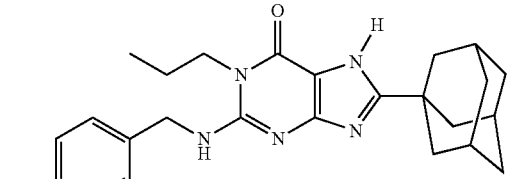<br>8-Adamantan-1-yl-2-(2,4-difluoro-benzylamino)-1-propyl-1,7-dihydro-purin-6-one. | 1HNMR (400 MHz, DMSO d6): δ 0.91 (t, 8 Hz, 3H), 1.58 (br. s, 2H), 1.71 (br.s, 6H), 1.92-2.01 (m, 9H), 3.98 (br.s, 2H), 4.56 (s, 2H), 7.03 (t, 8 Hz, 1H), 7.22 (t, 8 Hz, 1H), 7.31-7.37 (m, 1H), 7.48 (br.s, 1H), 12.07 (s, 1H) |

| Example No. | Structure and IUPAC name | NMR |
|---|---|---|
| 91 | 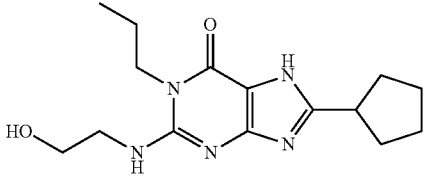<br>8-Cyclopentyl-2-(2-hydroxy-ethylamino)-1-propyl-1,7-dihydro-purin-6-one. | $^1$HNMR (400 MHz, DMSO-d6): δ 0.88 (b.s, 3H), 1.54-1.77 (b.s, 8H), 1.93 (b.s, 2H), 3.14 (b.s, 1H), 3.55 (b, s, 3H), 3.90 (b.s, 2H), 4.72 (b.s, 1H), 6.86 (b.s, 1H), 12.15 (b.s, 1H) |
| 92 | 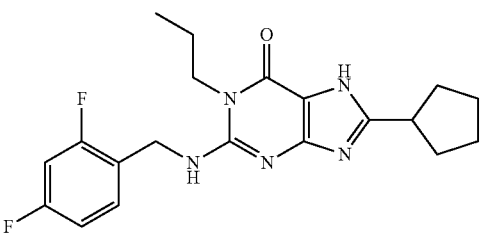<br>8-Cyclopentyl-2-(2,4-difluoro-benzylamino)-1-propyl-1,7-dihydro-purin-6-one. | $^1$HNMR (400 MHz, DMSO-d6): δ 0.91 (t, 8 Hz, 3H), 1.58 (b.s, 4H), 1.70-1.75 (b.s, 4H), 1.91 (b.s, 1H), 3.33 (m, 2H), 3.97 (b.s, 2H), 4.55 (b.s, 2H), 7.03 (b.s, 1H), 7.21 (b.s, 1H), 7.33 (b.s, 1H), |
| 93 | 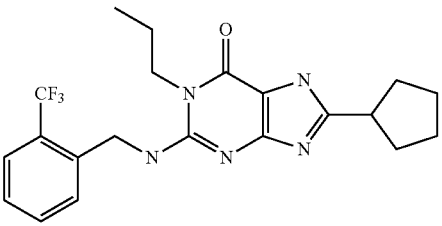<br>8-Cyclopentyl-1-propyl-2-(2-trifluoromethyl-benzylamino)-1,7-dihydro-purin-6-one. | $^1$HNMR (400 MHz, DMSO-d6): δ 0.94 (t, 8 Hz, 3H), 1.55-1.75 (m, 8H), 1.91 (b.s, 2H), 2.95-3.04 (m, 1H), 4.01 (b.s, 2H), 4.76 (s, 2H), 7.41-7.47 (m, 2H), 7.58-7.64 (m, 2H) |
| 94 | 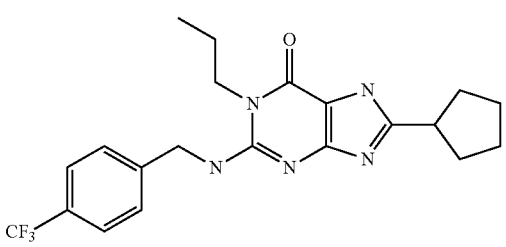<br>8-Cyclopentyl-1-propyl-2-(4-trifluoromethyl-benzylamino)-1,7-dihydro-purin-6-one. | $^1$HNMR (400 MHz, DMSO-d6): δ 0.92 (t, 8 Hz, 3H), 1.58-1.74 (m, 8H), 1.89 (b.s, 2H), 2.96-3.04 (m, 1H), 3.98 (b.s, 2H), 4.64 (b.s, 2H), 7.52 (s, 2H), 7.64-7.69 (m, 2H), 12.1 (b.s, 1H) |
| 95 | 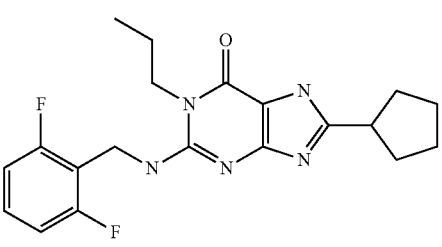<br>8-Cyclopentyl-2-(2,6-difluoro-benzylamino)-1-propyl-1,7-dihydro-purin-6-one. | $^1$HNMR (400 MHz, DMSO-d6): δ 0.84 (t, 8 Hz, 3H), 1.46-1.79 (m, 8H), 1.92 (b.s, 2H), 2.98-3.08 (m, 1H), 3.92 (t, 8 Hz, 2H), 5.58 (b.s, 2H), 7.08 (t, 8 Hz, 2H), 7.37 (b.s, 1H), 12.44 (b.s, 1H) |

| Example No. | Structure and IUPAC name | NMR |
|---|---|---|
| 96 | 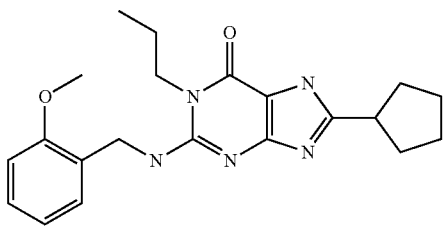<br>8-Cyclopentyl-2-(2-methoxy-benzylamino)-1-propyl-1,7-dihydro-purin-6-one. | $^{1}$HNMR (400 MHz, DMSO-d6): δ 0.93 (t, 8 Hz, 3H), 1.54-1.76 (m, 8H), 1.88-1.92 (m, 2H), 2.92-3.05 (m, 1H), 3.85 (s, 3H), 3.99 (b.s, 2H), 4.50 (b.s, 2H), 6.85-6.89 (m, 1H), 6.96-7.00 (m, 1H), 7.05-7.09 (m, 1H), 7.17-7.22 (m, 1H), 12.43 (b.s, 1H), |
| 97 | 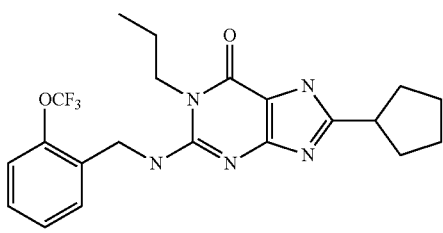<br>8-Cyclopentyl-1-propyl-2-(2-trifluoromethoxy-benzylamino)-1,7-dihydro-purin-6-one. | $^{1}$HNMR (400 MHz, DMSO-d6): δ 0.93 (t, 8 Hz, 3H), 1.56-1.76 (m, 8H), 1.90 (b.s, 2H), 2.96-3.04 (m, 1H), 3.97-4.01 (m, 2H), 4.63 (b.s, 2H), 7.36 (b.s, 3H), 7.51 (b.s, 1H), 12.48 (b.s, 1H), |
| 98 | 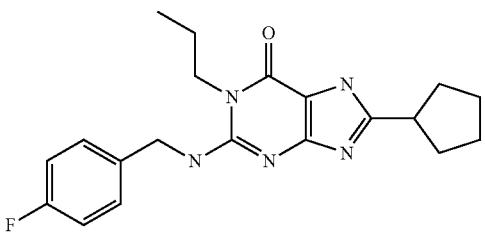<br>8-Cyclopentyl-2-(4-fluoro-benzylamino)-1-propyl-1,7-dihydro-purin-6-one. | $^{1}$HNMR (400 MHz, CD3OD): δ 0.90 (t, 8 Hz, 3H), 1.56-1.62 (m, 4H), 1.67-1.75 (m, 4H), 1.92 (b.s, 2H), 2.97-3.05 (m, 1H), 3.97 (b.s, 2H), 4.53 (b.s, 2H), 7.13 (t, 8 Hz, 2H), 7.31-7.37 (m, 2H) |
| 99 | 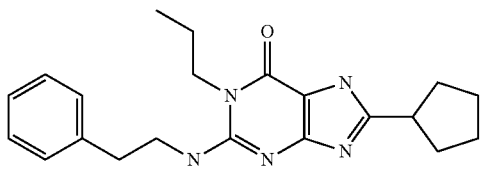<br>8-Cyclopentyl-2-phenethylamino-1-propyl-1,7-dihydro-purin-6-one. | $^{1}$HNMR (400 MHz, CD3OD): δ 0.84 (t, 8 Hz, 3H), 1.41-1.47 (m, 2H), 1.59-1.61 (m, 2H), 1.70-1.81 (m, 4H), 1.94 (b.s, 2H), 2.91 (t, 8 Hz, 2H), 3.01-3.037 (m, 1H), 3.52-3.56 (m, 2H), 3.87 (b.s, 2H), 7.19-7.24 (m, 3H), 7.29-7.32 (m, 2H), 12.41 (b.s, 1H), |
| 100 | 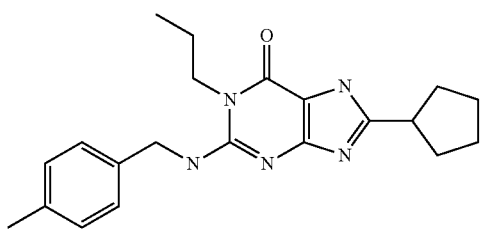<br>8-Cyclopentyl-2-(4-methyl-benzylamino)-1-propyl-1,7-dihydro-purin-6-one. | $^{1}$HNMR (400 MHz, CD3OD): δ 0.90 (t, 8 Hz, 3H), 1.56-1.58 (m, 4H), 1.69-1.75 (m, 4H), 1.91 (b.s, 2H), 2.26 (s, 3H), 2.99 (m, 1H), 3.97 (b.s, 2H), 4.51 (b.s, 2H), 7.11 (d, 8 Hz, 2H), 7.18 (d, 8 Hz, 2H), 12.41 (b.s, 1H) |

| Example No. | Structure and IUPAC name | NMR |
|---|---|---|
| 101 | 8-Cyclopentyl-1-propyl-2-[(thiophen-2-ylmethyl)-amino]-1,7-dihydro-purin-6-one. | ¹HNMR (400 MHz, CD3OD): δ 0.95 (t, 8 Hz, 3H), 1.61-1.68 (m, 4H), 1.82 (b.s, 4H), 2.07 (m, 2H), 3.13-3.20 (m, 1H), 3.98 (t, 8 Hz, 3H), 4.81 (s, 2H), 6.89-6.91 m, 1H), 7.03 (b.s, 1H), 7.20-7.22 (m, 1H) |
| 102 | 2-(3-Chloro-benzylamino)-8-cyclopentyl-1-propyl-1,7-dihydro-purin-6-one. | ¹HNMR (400 MHz, CD3OD): δ 1.00 9t, 8 Hz, 3H), 1.69-1.81 (m, 8H), 2.05 (b.s, 2H), 4.04 (t, 8 Hz, 3H), 7.21-7.36 (m, 4H), |
| 103 | 8-(Hexahydro-2,5-methano-pentalen-3a-yl)-2-(4-methyl-benzylamino)-1-propyl-1,7-dihydro-purin-6-one. | ¹HNMR (400 MHz, CD3OD): δ 0.99 (t, 8 Hz, 3H), 1.67-1.73 (m, 6H), 1.99 (d, 8 Hz, 4H), 2.16 (d, 8 Hz, 2H), 2.30 (s, 3H), 2.35 (b.s, 2H), 2.66 (m, 1H), 4.05 (t, 8 Hz, 2H), 4.63 (s, 2H), 7.11 (d, 8 Hz, 2H), 7.25 (d, 8 Hz, 2H) |
| 104 | 8-(Hexahydro-2,5-methano-pentalen-3a-yl)-1-propyl-2-(4-trifluoromethyl-benzylamino)-1,7-dihydro-purin-6-one. | ¹HNMR (400 MHz, CD3OD ): δ 1.01 (t, 4 Hz, 3H), 1.64-1.76 (m, 7H), 1.95-1.98 (m, 4H), 2.11-2.14 (m, 2H), 2.32 (s, 2H), 4.06 (t, 8 Hz, 2H), 4.73 (s, 2H), 7.52 (d, 8 Hz, 2H), 7.59 (d, 2H) |
| 105 | 8-Cyclohexyl-2-(4-fluoro-benzylamino)-1-propyl-1,7-dihydro-purin-6-one. | 1HNMR (400 MHz, CD3OD): d 0.992 (t, J = 7.4 Hz, 3H); 1.23-2.03 (m, 12H); 2.66-2.802(m, 1H); 4.040 (t, J = 6.8 Hz, 2H); 4.640(s, 2H); 6.94-7.12(m, 2H); 7.33-7.46(m, 2H) |

Example 106

8-Adamantan-1-yl-2-methylamino-1-propyl-1,7-dihydro-purin-6-one

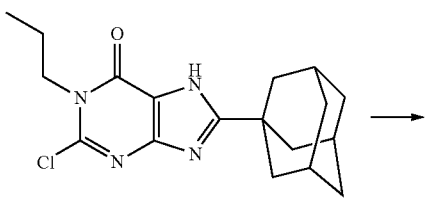

→

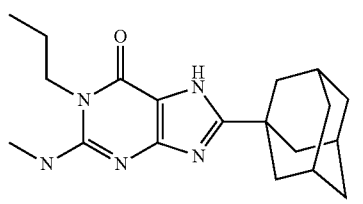

8-Adamantan-1-yl-2-chloro-1-propyl-1,7-dihydro-purin-6-one (0.05 g, 0.14 mmol) was dissolved in methanol and the resulting mixture was degassed. Methyl amine in THF (2 ml) was added and heated at 60° C. for 5 hours. The reaction mixture was concentrated and the residue was further purified by HPLC to provide the title compound as a yellow solid. (5 mg, 20%)

$^1$HNMR (400 MHz, DMSO d6): δ 0.86-0.92 (t, J=7.4 Hz, 3H); 1.48-1.58 (m, 2H); 1.67-1.77 (m, 6H); 1.81-2.06 (m, 9H); 2.8-2.85 (m, 3H); 3.82-3.96 (m, 2H); 6.6-6.95 (m, 1H); 12.16-12.22 (m, 1H).

Example 107

8-Adamantan-1-yl-2-dimethylamino-1-propyl-1,7-dihydro-purin-6-one

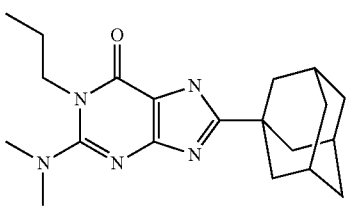 [SMILES: CCCn1c(N(C)C)nc2nc(C34CC5CC(CC(C5)C3)C4)[nH]c2c1=O]

The compound is obtained using an analogous procedure as in example 106.

$^1$HNMR (400 MHz, DMSO d6): δ 0.86-0.92 (t, J=7.4 Hz, 3H); 1.48-1.58 (m, 2H); 1.67-1.77 (m, 6H); 1.82-2.06 (m, 9H); 2.70 (s, 3H); 2.738 (s, 3H); 3.98-4.06 (m, 2H); 12.58-12.62 (m, 1H).

Example 108

8-Cyclopentyl-2-phenylamino-1-propyl-1,7-dihydro-purin-6-one

To a solution of 8-cyclopentyl-2-chloro-1-propyl-1,7-dihydro-purin-6-one (0.06 g, 0.21 mmol) in N-methyl-pyrrolidone (1 ml) was added aniline (0.20 g, 2.14 mmol) and the mixture was heated at 150° C. overnight. Water was added to the reaction mixture and the product was extracted with ethyl acetate. The ethyl acetate layer was dried over anhydrous sodium sulphate and concentrated under vacuum. The crude product was purified by preparative TLC using 5% methanol in dichloromethane to give the product (0.034 g, 47%) as a brown solid.

$^1$H NMR (400 MHz, CD$_3$OD): δ 1.01 (s, J=8 Hz, 3H), 1.68 (br. s, 2H), 1.73-1.83 (m, 6H), 2.04-2.10 (m, 2H), 3.15 (t, J=8 Hz, 1H), 4.22 (t, J=8 Hz, 2H), 7.13 (t, J=8 Hz, 1H), 7.32 (t, J=8 Hz, 2H), 7.49 (d, J=8 Hz, 2H).

Examples 109 to 111 were prepared following the experimental procedure as given for Example 108

| Example No. | Structure and IUPAC name | NMR |
|---|---|---|
| 109 | 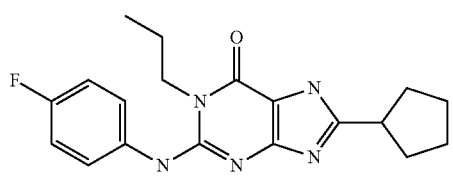<br>8-Cyclopentyl-2-(4-fluoro-phenylamino)-1-propyl-1,7-dihydro-purin-6-one | $^1$HNMR (400 MHz, CD$_3$OD): δ 1.01 (t, 8 Hz, 3H), 1.67-1.68 (m, 2H), 1.73-1.82 (m, 6H), 2.03-2.08 (m, 2H), 3.14 (t, 8 Hz, 2H), 4.19 (t, 8 Hz, 2H), 7.06 (t, 8 Hz, 2H), 7.45-7.49 (m, 2H) |

| Example No. | Structure and IUPAC name | NMR |
|---|---|---|
| 110 | 8-Cyclopentyl-1-propyl-2-(3-trifluoromethyl-henylamino)-1,7-dihydro-purin-6-one | ¹HNMR (400 MHz, DMSO d6): δ 0.89 (t, J = 7.2 Hz, 3H), 1.58-1.78 (m, 8H), 1.93 (br s, 1H), 2.98-3.05 (m, 1H), 4.09-4.16 (m, 2H), 7.97-7.44 (m, 1H), 7.55 (t, J = 8.0 Hz, 1H), 7.81-7.88 (m, 2H). (m + 1) = 406. |
| 111 | 8-Cyclopentyl-2-(3-fluoro-phenylamino)-1-propyl-1,7-dihydro-purin-6-one | ¹HNMR (400 MHz, DMSO d6): δ 0.87 (t, J = 7.6 Hz, 3H), 1.55-1.80 (m, 8H), 1.92-1.97 (m, 2H), 3.03-3.07 (m, 1H), 4.13-4.17 (m, 2H), 6.83-6.87 (m, 1H), 7.30-7.35 (m, 2H), 7.47-7.49 (m, 1H), 8.6 (br s, 1H), 12.4 (br s, 1H). (m + 1) = 356. |

Example 112

3-[8-(Hexahydro-2,5-methano-pentalen-3a-yl)-6-oxo-1-propyl-6,7-dihydro-1H-purin-2-yloxy]-benzoic acid

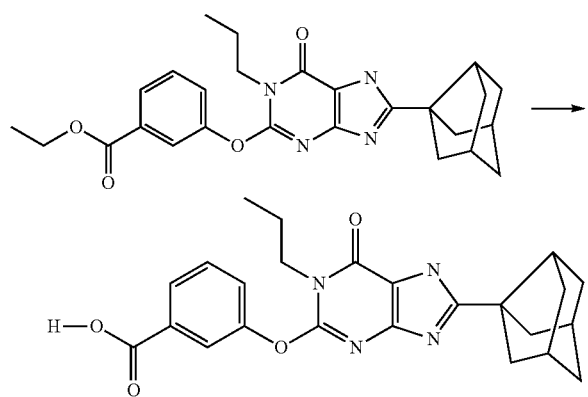

To a solution of 3-[8-(Hexahydro-2,5-methano-pentalen-3a-yl)-6-oxo-1-propyl-6,7-dihydro-1H-purin-2-yloxy]-benzoic acid ethyl ester (prepared by following similar, procedure as Example 1, 0.073 g, 0.157 mmol) in a mixture of ethanol (5 ml) water (5 ml) and THF (5 ml) was added sodium hydroxide (0.019 g, 0.473 mmol) and the reaction mixture was heated at 50° C. overnight. The reaction mixture after cooling to room temperature was concentrated under vacuum to remove THF. The aqueous layer was acidified with 1N HCl. The precipitate obtained was extracted with ethylacetate. The ethyl acetate layer was dried over anhydrous sodium sulphate and concentrated under vacuum. The crude product was purified by column chromatography using 5% methanol in DCM as the eluant to give the product (0.041 g, 59%) as an off white solid.

¹HNMR (400 MHz, DMSO d6): δ 0.95 (t, J=8 Hz, 3H), 1.58 (d J=8 Hz, 4H), 1.75 (q, J=8 Hz, 2H), 1.87 (d, J=8 Hz, 4H), 2.08 (d, J=8 Hz, 2H), 2.27 (s, 2H), 2.55 (m, 1H), 4.14 (t, J=8 Hz, 2H), 7.60 (m, 2H), 7.64 (s, 1H), 7.89 (m, 1H).

Examples 113 to 115 were prepared following the experimental procedure as given for Example 112.

| Example No. | Structure and IUPAC name | NMR |
|---|---|---|
| 113 | 8-Adamantyl-6-oxo-1-propyl-6,7-dihydro-1H-purin-2-yloxy)-acetic acid. | 1HNMR (400 MHz, DMSO d6): d 0.85-0.92 (t, J = 7.4 Hz, 3H); 1.62-1.78(m, 8H); 1.92-2.090(m, 9H); 3.94-4.02(m, 2H); 4.92-4.98(m, 2H); 12.60-12.80(m, 1H); 13.02-13.25(bs, 1H) |

| Example No. | Structure and IUPAC name | NMR |
|---|---|---|
| 114 | (8-Cyclopentyl-6-oxo-1-propyl-6,7-dihydro-1H-purin-2-yloxy)-acetic acid. | ¹HNMR (400 MHz, DMSO-d6): δ 0.89 (t, 8 Hz, 3H), 1.62-1.81 (m, 6H), 1.97 (b.s, 2H), 3.06-3.17 (m, 1H), 3.98 (t, 8 Hz, 2H), 4.93 (s, 2H), 12.9 (b.s, 1H) |
| 115 | 3-(8-Cyclopentyl-6-oxo-1-propyl-6,7-dihydro-1H-purin-2-yloxy)-benzoic acid | ¹HNMR (400 MHz, DMSO d6): δ 0.93 (t, J = 7.2 Hz, 3H), 1.55-1.58 (m, 2H), 1.64-1.73 (m, 6H), 1.75-1.94 (m, 2H), 3.0-3.11 (m, 1H), 4.09-4.13 (m, 2H), 7.53-7.62 (m, 2H), 7.79(d, J = 14 Hz, 1H), 7.88 (d, J = 7.6 Hz, 1H), 12.9 (br s, 1H), 13.2 (br s, 1H). (m + 1) = 383. |

Example 116

4-[8-(Hexahydro-2,5-methano-pentalen-3a-yl)-6-oxo-1-propyl-6,7-dihydro-1H-purin-2-yloxy]-benzoic acid:4366

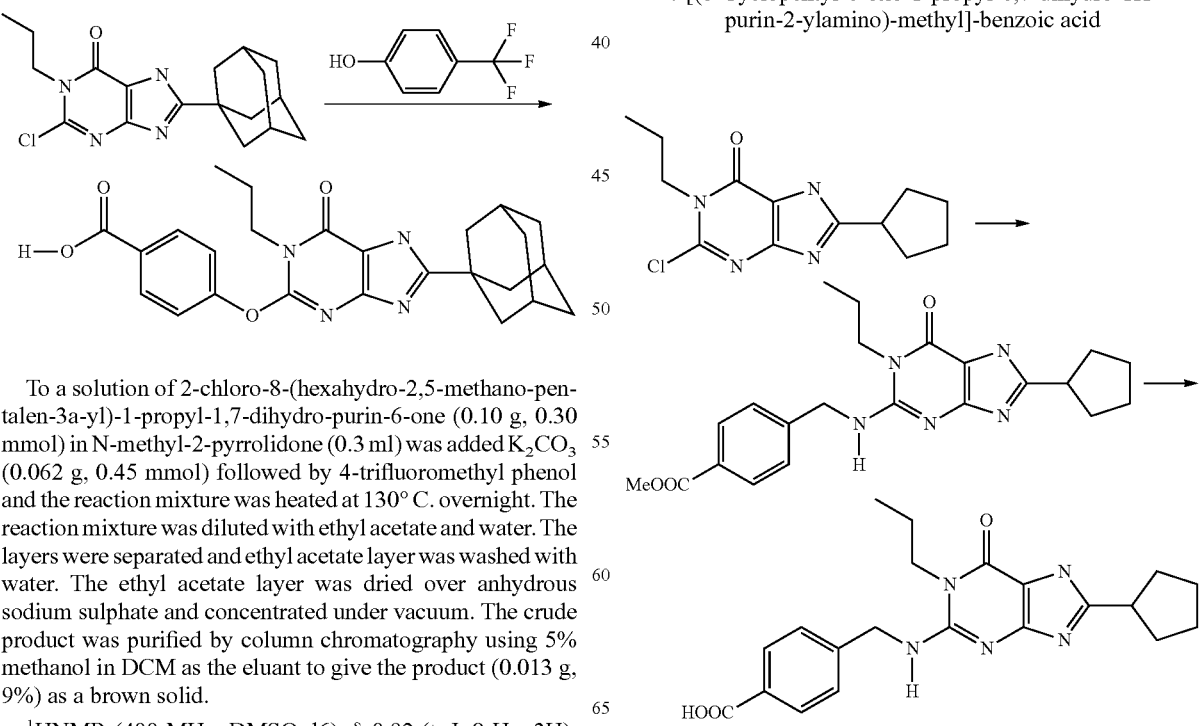

To a solution of 2-chloro-8-(hexahydro-2,5-methano-pentalen-3a-yl)-1-propyl-1,7-dihydro-purin-6-one (0.10 g, 0.30 mmol) in N-methyl-2-pyrrolidone (0.3 ml) was added $K_2CO_3$ (0.062 g, 0.45 mmol) followed by 4-trifluoromethyl phenol and the reaction mixture was heated at 130° C. overnight. The reaction mixture was diluted with ethyl acetate and water. The layers were separated and ethyl acetate layer was washed with water. The ethyl acetate layer was dried over anhydrous sodium sulphate and concentrated under vacuum. The crude product was purified by column chromatography using 5% methanol in DCM as the eluant to give the product (0.013 g, 9%) as a brown solid.

¹HNMR (400 MHz, DMSO d6): δ 0.92 (t, J=8 Hz, 3H), 1.57 (s, 4H), 1.72-1.87 (m, 6H), 2.04-2.09 (m, 3H), 2.30 (s, 2H), 2.5 (s, 1H), 4.1 (br., s, 2H), 7.34-7.40 (m, 2H), 8.0 (s, 2H), 12.7 (s, 1H), 12.9 (s, 1H)

Example 117

4-[(8-Cyclopentyl-6-oxo-1-propyl-6,7-dihydro-1H-purin-2-ylamino)-methyl]-benzoic acid

Step 1: 4-[(8-Cyclopentyl-6-oxo-1-propyl-6,7-dihydro-1H-purin-2-ylamino)-methyl]-benzoic acid methyl ester To a solution of 8-cyclopentyl-2-chloro-1-propyl-1,7-dihydro-purin-6-one (0.15 g, 0.535 mmol) in N-methyl-pyrrolidone (1 ml) was added methyl-4-(amino methyl)benzoate hydrochloride (0.216 g, 1.07 mmol) followed by diisopropylethylamine (242 mg, 1.874 mmol) and the resulting reaction mixture was heated at 150° C. overnight. To the reaction mixture was added water and the product was extracted with ethyl acetate. The ethyl acetate layer was dried over anhydrous sodium sulphate and concentrated under vacuum. The crude product was purified by preparative TLC using 5% methanol in dichloromethane as solvent system to give the product (0.11 g, 50%) as an off white solid.

$^1$HNMR (400 MHz, CD$_3$OD): δ 1.01 (t, J=8 Hz, 3H), 1.68-1.83 (m, 8H), 2.04-2.08 (m, 2H), 3.14 (t, J=8 Hz, 1H), 3.89 (s, 3H), 4.07 (t, J=8 Hz, 2H), 4.73 (s, 2H), 7.47 (d, J=8 Hz, 2H), 7.83 (d, J=8 Hz, 2H).

Step 2: Preparation of 4-[(8-cyclopentyl-6-oxo-1-propyl-6,7-dihydro-1H-purin-2-ylamino)-methyl]-benzoic acid To a solution of 4-[(8-cyclopentyl-6-oxo-1-propyl-6,7-dihydro-1H-purin-2-ylamino)-methyl]-benzoic acid methyl ester (0.081 g, 0.198 mmol) in a mixture of MeOH/H2O/THF (5 ml each) was added NaOH (0.024 g, 0.594 mmol) and the resulting reaction mixture was refluxed overnight. The reaction mixture was concentrated under reduced pressure. The residue was dissolved in water and neutralized with 1N HCl and then extracted with ethyl acetate. The ethyl acetate layer was dried over anhydrous sodium sulphate and concentrated under vacuum. The crude product was purified by washing repeatedly with diethyl ether to give the product (0.025 g, 32%) as an off white solid.

$^1$H NMR (400 MHz, CD$_3$OD): δ 1.00 (t, J=8 Hz, 3H), 1.68-1.81 (m, 7H), 1.99 (s 1H), 2.06-2.10 (m, 2H), 3.16 (t, J=8 Hz, 1H), 4.06 (t, J=8 Hz, 2H), 4.73 (s, 2H), 7.44 (d, 8 Hz, 2H), 7.95 (d, J=-8 Hz, 2H).

Example 118

(8-Cyclopentyl-6-oxo-1-propyl-6,7-dihydro-1H-purin-2-ylamino)-acetic acid

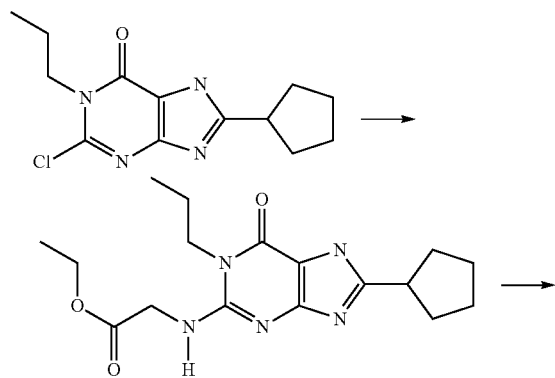

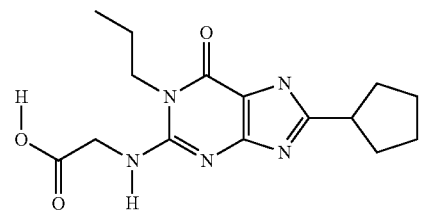

Step 1: (8-Cyclopentyl-6-oxo-1-propyl-6,7-dihydro-1H-purin-2-ylamino)-acetic acid ethyl ester To a solution of 8-cyclopentyl-2-chloro-1-propyl-1,7-dihydro-purin-6-one (0.10 g, 0.357 mmol) in N-methylpyrrolidone (2 ml) was added glycine ethyl ester (0.074 g, 0.532 mmol) followed by diisopropyl ethylamine (0.18 ml, 1.07 mmol). The resulting reaction mixture was heated at 130° C. overnight. To the reaction mixture was added ethyl acetate followed by water. The layers were separated. The ethyl acetate layer was washed thrice with water. The organic layer was dried over anhydrous sodium sulphate and concentrated under vacuum. The crude product was purified by preparative TLC using 5% methanol in dichloromethane as the solvent system to give the product (0.060 g, 48%) as an off white solid.

$^1$HNMR (400 MHz, DMSO d6): δ 0.87 (t, J=8 Hz, 3H), 1.19 (t, J=8 Hz, 3H), 1.59 (br. s, 4H), 1.70-1.79 (m, 4H), 1.93 (br. s, 2H), 3.33 (br. s, 1H), 3.93 (s, 2H), 4.03 (t, J=8 Hz, 2H), 4.1 (q, J=8 Hz, 2H), 7.4 (br. s, 1H), 12.2 (br. s, 1H).

Step 2: (8-Cyclopentyl-6-oxo-1-propyl-6,7-dihydro-1H-purin-2-ylamino)-acetic acid To a solution of (8-cyclopentyl-6-oxo-1-propyl-6,7-dihydro-1H-purin-2-ylamino)-acetic acid ethyl ester (0.05 g, 0.144 mmol) prepared in the previous step in a mixture of water (5 ml), THF (5 ml) and ethanol (5 ml) was added sodium hydroxide (0.017 g, 0.425 mmol) and the resulting reaction mixture was heated at 50-60° C. overnight. The solvent was evaporated under reduced pressure and the residue was dissolved in 2 ml of water. The solution obtained was neutralized with 1N HCl. The solid formed was extracted with ethyl acetate. The ethyl acetate layer was washed with water and dried over anhydrous sodium sulphate and concentrated under vacuum. The crude product was purified by crystallization with dichloromethane/ether/methanol mixture to give the product (0.006 g, 13%) as a pale yellow solid.

$^1$HNMR (400 MHz, DMSO d6): δ 0.90 (t, J=8 Hz, 3H), 1.56-1.73 (m, 4H), 1.74-1.88 (m, 4H), 1.89-2.01 (br. s, 2H), 3.01-3.10 (m, 1H), 3.2 (s, 1H), 3.93 (br. s, 3H), 7.25 (br. s, 1H), 12.2 (s, 1H).

Example 119

2-(8-Cyclohexyl-6-oxo-1-propyl-6,7-dihydro-1H-purin-2-ylamino)-3-(3-fluoro-phenyl)-propionic acid

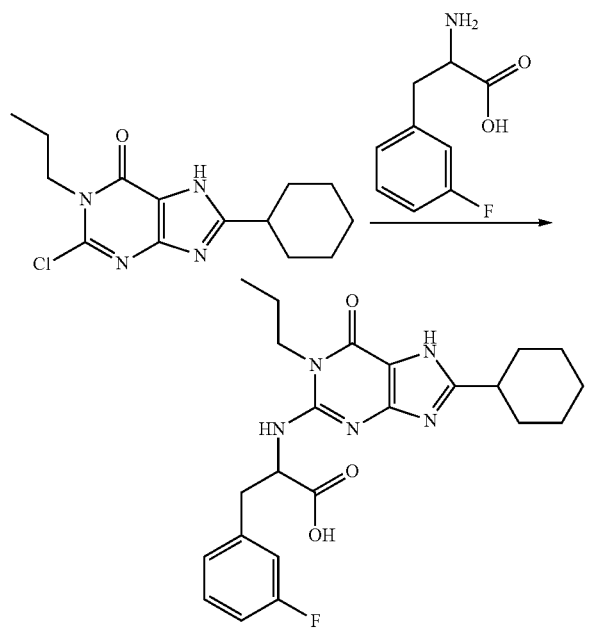

To a solution of 2-Amino-3-(3-fluoro-phenyl)-propionic acid (112 mg, 0.612 mmol) and $K_2CO_3$ (140 mg, 1.02 mmol) in water (5 ml) was added 2-Chloro-8-cyclohexyl-1-propyl-1,7-dihydro-purin-6-one (150 mg, 0.51 mmol). The reaction mixture was stirred at refluxing temperature for overnight. Aqueous ammonium chloride was added to the reaction mixture. The solid obtained was filtered and dried. The crude product was purified by preparative HPLC to obtain 4 mg (~2%) of pure product as pink solid.

$^1$HNMR (400 MHz, $CD_3OD$): δ 0.85 (t, J=7.2 Hz, 3H), 1.28-1.31 (m, 2H), 1.28-1.62 (m, 4H), 1.72-1.76 (m, 2H), 1.81-1.89 (m, 2H), 1.94-2.2 (m, 2H), 2.71-2.80 (m, 1H), 3.19-3.26 (m, 2H), 3.38-3.43 (m, 2H), 3.84-3.94 (m, 1H), 4.01-4.12 (m, 1H), 6.89-6.94 (m, 1H), 6.98-7.00 (m, 1H), 7.04-7.06 (m, 1H), 7.23-7.28 (m, 1H).

Example 120

8-(3,4-Dihydroxy-cyclopentyl)-2-(3-methoxy-phenoxy)-1-propyl-1,7-dihydro-purin-6-one

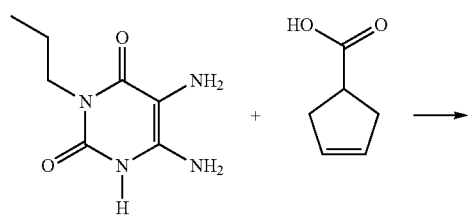

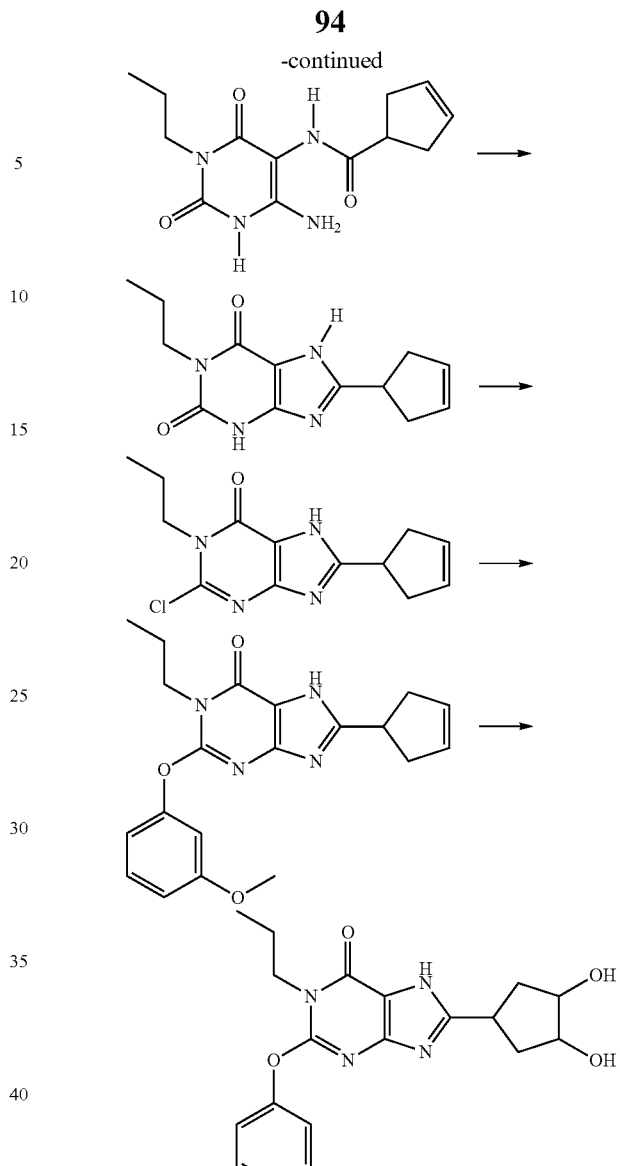

Step 1: Cyclopent-3-enecarboxylic acid (6-amino-2,4-dioxo-3-propyl-1,2,3,4-tetrahydro-pyrimidin-5-yl)-amide Same as step 1 in preparation 1

Step 2: Cyclopent-3-enyl-1-propyl-3,7-dihydro-purine-2,6-dione

To a solution of cyclopent-3-enecarboxylic acid (6-amino-2,4-dioxo-3-propyl-1,2,3,4-tetrahydro-pyrimidin-5-yl)-amide (0.5 g, 1.8 mmol) in DMF at 100° C., phosphorus pentoxide (0.64 g, 4.5 mmol) was added. Reaction mixture was stirred for one hour at same temperature. Reaction mixture was cooled to room temperature and it was further cooled to 0° C. To that ice cold water was added and stirred for 10 minutes to get precipitate. This precipitate was filtered and washed with water followed by diethyl ether. The precipitate so obtained was dried under high vacuum.

1HNMR (400 MHz, DMSO-d6): δ 0.85 (t, 8 Hz, 3H), 1.49-1.56 (m, 2H), 2.57-2.62 (m, 2H), 2.63-2.75 (m, 2H), 3.48-3.53 (m, 1H), 3.78 (t, 8 Hz, 2H), 5.73 (s, 2H), 11.71 (s, 1H); 13.02 (s, 1H).

Step 3: 2-Chloro-8-cyclopent-3-enyl-1-propyl-1,7-dihydro-purin-6-one

Same as step 2 in preparation 1.

Step 4: 8-Cyclopent-3-enyl-2-(3-methoxy-phenoxy)-1-propyl-1,7-dihydro-purin-6-one Same as Example 1

1HNMR (400 MHz, DMSO-d6): δ 0.92 (t, 8 Hz, 3H), 1.69-1.75 (m, 2H), 2.57-2.71 (m, 4H), 3.43-3.50 (m, 1H), 3.76 (s, 3H), 4.08 (t, 8 Hz, 2H), 5.70 (s, 2H), 6.80-6.92 (m, 3H), 7.34 (t, 8 Hz, 1H), 12.92 (s, 1H)

Step 5: 8-(3,4-Dihydroxy-cyclopentyl)-2-(3-methoxy-phenoxy)-1-propyl-1,7-dihydro-purin-6-one To a solution of 8-cyclopent-3-enyl-2-(3-methoxy-phenoxy)-1-propyl-1,7-dihydro-purin-6-one (0.075 g, 0.20 mmol) and N-methyl morpholine N-oxide (0.036 g, 0.30 mmol) in a mixture of acetone, t-butanol, and water in the ratio 60:1:1, catalytic amount of osmium tetroxide (2 mg) was added. Reaction mixture was allowed to stir for 2 hours at room temperature. The reaction mixture was quenched with saturated sodium sulphite solution and was diluted with ethyl acetate and water. The ethyl acetate layer was washed with water, dried over anhydrous sodium sulphate and concentrated under vacuum. The crude product was purified by preparative TLC using 3% methanol in DCM to give the product (0.014 g, 13%) as light green solid.

¹HNMR (400 MHz, DMSO d6): δ 0.94 (t, 8 Hz, 3H), 1.71-1.76 (m, 2H), 1.89-1.92 (m, 4H), 3.40 (b.s, 1H), 6.84-6.90 (m, 3H), 7.34-7.38 (t, 8 Hz, 3H)

Example 121

8-[4-(5-Chloro-pyridin-2-yloxymethyl)-bicyclo[2.2.2]oct-1-yl]-2-(3,4-difluoro-phenoxy)-1-propyl-1,7-dihydro-purin-6-one

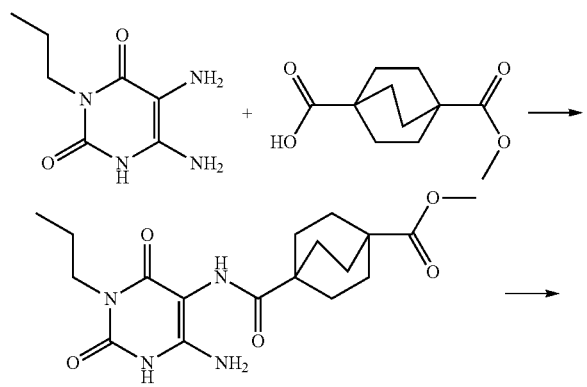

Step 1: 4-(6-Amino-2,4-dioxo-3-propyl-1,2,3,4-tetrahydro-pyrimidin-5-ylcarbamoyl)-bicyclo[2.2.2]octane-1-carboxylic acid methyl ester Same as step 1 in preparation 1.

Step 2: 4-(2,6-Dioxo-1-propyl-2,3,6,7-tetrahydro-1H-purin-8-yl)-bicyclo[2.2.2]Octane-1-carboxylic acid methyl ester Same as step 2 in example 11.

1HNMR (400 MHz, DMSO-d6): δ 0.87 (t, 8 Hz, 3H), 1.50-1.55 (m, 2H), 1.76-1.94 (m, 12H), 3.59 (s, 3H), 3.77 (t, 8 Hz, 2H), 11.72 (b.s, 1H), 12.82 (br.s, 1H).

Step 3: 8-(4-Hydroxymethyl-bicyclo[2.2.2]oct-1-yl)-1-propyl-3,7-dihydro-purine-2,6-dione To a solution of 4-(2,6-dioxo-1-propyl-2,3,6,7-tetrahydro-1H-purin-8-yl)-bicyclo[2.2.2]octane-1-carboxylic acid

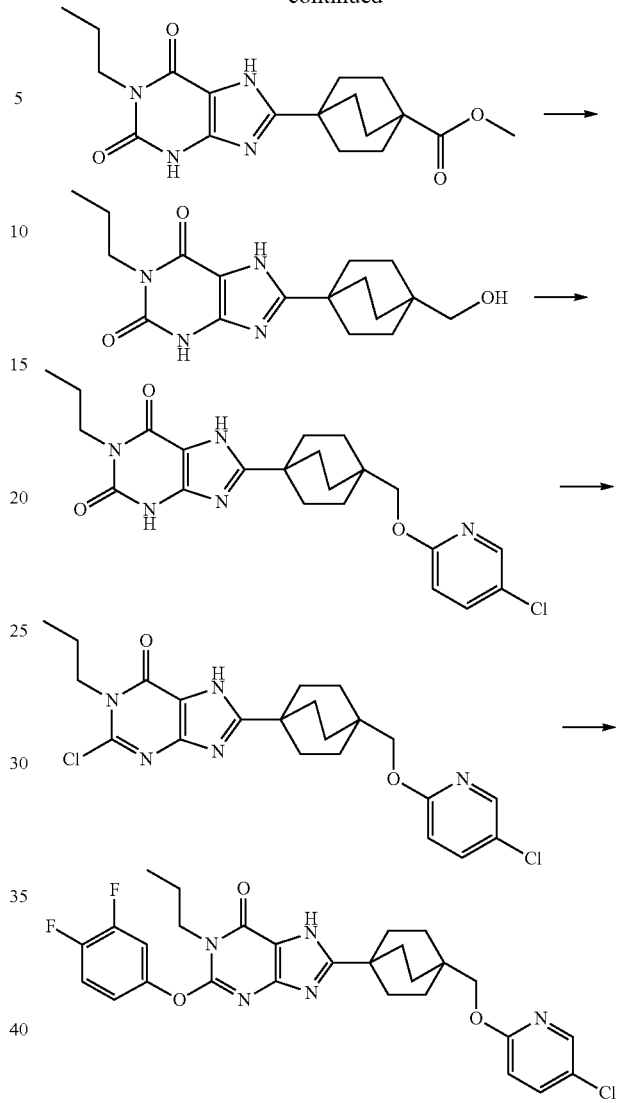

methyl ester (2.4 g, 0.006 moles) in THF (35 ml), methanol (0.4 ml) was added. To this mixture, lithium borohydride (1.45 g, 0.066 mole) was added slowly and refluxed overnight. Reaction mixture was concentrated under reduced pressure and quenched with 1N HCl. Water was added to the residue and extracted with ethyl acetate. Organic layer was dried over anhydrous sodium sulphate and concentrated under vacuum.

1HNMR (400 MHz, DMSO-d6): δ 0.83 (t, 8 Hz, 3H), 1.21 (s, 2H), 1.33-1.40 (m, 5H), 1.51 (d, 8 Hz, 2H), 1.78-1.82 (m, 5H), 3.045 (d, 4 Hz, 2H), 3.75 (t, 8 Hz, 2H), 11.67 (b.s, 1H), 12.71 (br.s, 1H).

Step 4: Synthesis of 8-[4-(5-Chloro-pyridin-2-yloxymethyl)-bicyclo[2.2.2]oct-1-yl]-1-propyl-3,7-dihydro-purine-2,6-dione To a solution of 8-(4-hydroxymethyl-bicyclo[2.2.2]oct-1-yl)-1-propyl-3,7-dihydro-purine-2,6-dione (0.2 g, 0.60 mmol) in DMF (4 ml) was added NaH (60% dispersion in mineral oil, 0.079 g, 1.98 mmol) at room temperature followed by 2-bromo-5-chloro-pyridine and maintained at 120° C. overnight. Reaction mixture was concentrated under reduced pressure quenched with water and was extracted with ethyl acetate. The organic layer was dried over anhydrous sodium sulphate and concentrated under vacuum. The crude product was purified by column chromatography using 2% methanol in dichloromethane as solvent system.

1HNMR (400 MHz, DMSO-d6): δ 0.83 (t, J=8 Hz, 3H), 1.48-1.57 (m, 8H), 1.84-1.88 (m, 6H), 3.75 (t, J=8 Hz, 2H), 3.91 (s, 2H), 6.86 (d, J=8 Hz, 1H), 1.76-1.79 (m, 1H), 8.16 (d, J=4 Hz, 1H).

Step 5: Synthesis of 2-Chloro-8-[4-(5-chloro-pyridin-2-yloxymethyl)-bicyclo[2.2.2]oct-1-yl]-1-propyl-1,7-dihydro-purin-6-one Same as Step 2 in preparation 1.

Step 6: Synthesis of 8-[4-(5-Chloro-pyridin-2-yloxymethyl)-bicyclo[2.2.2]oct-1-yl]-2-(3,4-difluoro-phenoxy)-1-propyl-1,7-dihydro-purin-6-one Same as example 1.

1HNMR (400 MHz, DMSO d6): δ 0.94 (t, 8 Hz, 3H), 1.75 (m, 6H), 1.71-1.75 (m, 2H), 1.80-1.89 (m, 6H), 3.93 (s, 2H), 4.09 (m, 2H), 6.87 (d, 8 Hz, 1H), 7.18-7.26 (m, 1H), 7.53-7.60 (m, 1H), 7.65-7.7.69 (m, 1H), 7.77-7.80 (m, 1H), 8.17 (b.s, 1H).

Examples 122 and 123 were prepared following the experimental procedure as given for Example 121.

| Example No. | Structure and IUPAC name | NMR |
|---|---|---|
| 122 | 2-Cyclopentyloxy-1-propyl-8-[4-(pyridin-2-yloxymethyl)-bicyclo[2.2.2]oct-1-yl]-1,7-dihydro-purin-6-one | 1HNMR (400 MHz, DMSO d6): δ 0.85 (t, 8 Hz, 3H), 1.29-1.37 (m, 2H), 1.57-1.60 (m, 5H), 1.67-1.73 (m, 5H), 1.89 (b.s, 11H), 3.88-3.90 (b.s, 2H), 3.94 (s, 2H), 6.81 (d, 8 Hz, 1H), 6.93-6.96 (m, 1H), 7.66-7.71 (m, 1H), 8.12-8.13 (m, 1H) |
| 123 | 8-[4-(5-Chloro-pyridin-2-yloxymethyl)-bicyclo[2.2.2]oct-1-yl]-2-(2-methyl-pyridin-3-yloxy)-1-propyl-1,7-dihydro-purin-6-one | 1HNMR (400 MHz, DMSO d6): δ 0.96 (t, 8 Hz, 3H), 1.53-1.57 (m, 5H), 1.76-1.83 (m, 7H), 2.37 (s, 3H), 3.92 (s, 2H), 4.15 (m, 2H), 6.86-6.88 (d, 8 Hz, 1H), 7.73(m, 1H) 7.77-7.78 (m, 1H), 8.17 (s, 1H), 8.415-.426 (d, 4 Hz, 1H), 12.85 (b.s, 1H) |

Example 124

8-Cyclopentyl-2-(2-methyl-1-oxy-pyridin-3-yloxy)-1-propyl-1,7-dihydro-purin-6-one

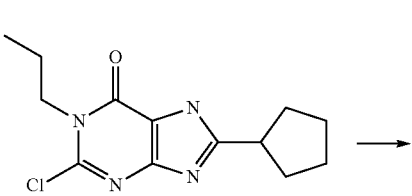

-continued

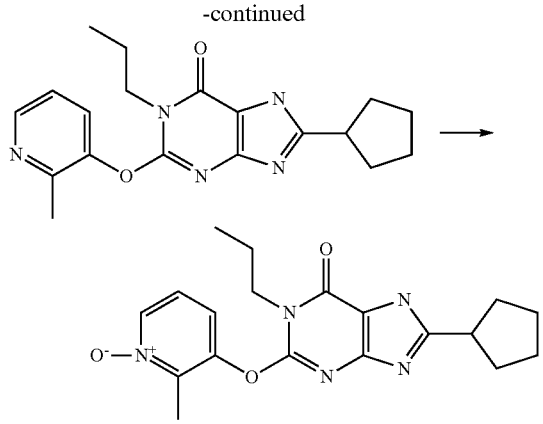

Step 1: Synthesis of 8-Cyclopentyl-2-(2-methyl-pyridin-3-yloxy)-1-propyl-1,7-dihydro-purin-6-one Same as Example 1

Step 2: Synthesis of 8-Cyclopentyl-2-(2-methyl-1-oxy-pyridin-3-yloxy)-1-propyl-1,7-dihydro-purin-6-one To a solution of m-chloroperbenzoic acid (0.04 g, 0.212 mmole) in anhydrous dichloromethane (2 ml), 8-cyclopentyl-2-(2-methyl-pyridin-3-yloxy)-1-propyl-1,7-dihydro-purin-6-one (0.05 g, 0.14 mmoles) was added. The reaction mixture was stirred at room temperature for 2 hours. To the reaction mixture 10% sodium hydroxide was added and compound was extracted into dichloromethane. This DCM fraction was dried over anhydrous sodium sulphate and was concentrated under reduced pressure. The crude product was purified by preparative T.L.C using 3% methanol in DCM to get brown solid (2 mg, 4% yield).

$^1$HNMR (400 MHz, DMSO d6+D2O): δ 0.96 (t, 8 Hz, 3H), 1.59-1.78 (m, 8H), 1.96 (m, 2H), 2.30 (s, 3H), 3.12-3.24 (m, 1H), 7.49-7.54 (m, 2H), 8.34 (d, 8 Hz, 1H)

Example 125

3-(8-Cyclopentyl-6-oxo-1-propyl-6,7-dihydro-1H-purin-2-yloxy)-benzamide

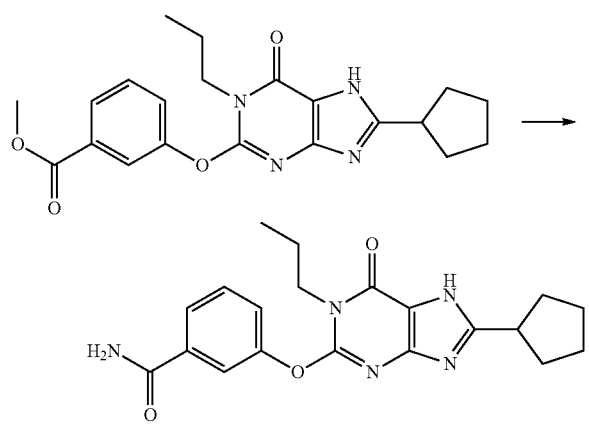

A mixture of 3-(8-Cyclopentyl-6-oxo-1-propyl-6,7-dihydro-1H-purin-2-yloxy)-benzoic acid methyl ester (0.07 g, 0.17 mmol, 1.0 eq) and 7-methyl-1,5,7-triazabicyclo[4.4.0]dec-5-ene (0.034 g, 0.247 m·mol, 1.4 eq) was taken in THF. To this was added Liq.NH3 (~3 g) through septum in sealed tube at −78° C. and then heated at 50° C. overnight. Crude reaction mixture was purified by preparative TLC to give the product as a white solid (0.04 g) in 60% yield.

Some other non-limiting examples of compounds of the present disclosure are:
2-Benzyloxy-8-cyclopentyl-1-propyl-1,7-dihydro-purin-6-one,
8-Cyclopentyl-2-(3,5-difluoro-benzyloxy)-1-propyl-1,7-dihydro-purin-6-one,
8-Cyclopentyl-1-propyl-2-(pyridin-3-ylmethoxy)-1,7-dihydro-purin-6-one,
2-But-2-ynyloxy-8-cyclopentyl-1-propyl-1,7-dihydro-purin-6-one,
8-Cyclopentyl-1-propyl-2-(pyrimidin-2-yloxy)-1,7-dihydro-purin-6-one,
8-Cyclopentyl-1-propyl-2-(pyridin-2-ylsulfanyl)-1,7-dihydro-purin-6-one,
8-Cyclopentyl-2-(1H-imidazol-2-ylsulfanyl)-1-propyl-1,7-dihydro-purin-6-one,
8-Cyclopentyl-2-ethanesulfonyl-1-propyl-1,7-dihydro-purin-6-one,
8-Cyclopentyl-2-ethylsulfanyl-1-propyl-1,7-dihydro-purin-6-one,
2-Cyclohexylsulfanyl-8-cyclopentyl-1-propyl-1,7-dihydro-purin-6-one,
(8-Cyclopentyl-6-oxo-1-propyl-6,7-dihydro-1H-purin-2-ylsulfanyl)-acetic acid ethyl ester,
8-Cyclopentyl-1-propyl-2-(pyrimidin-2-ylamino)-1,7-dihydro-purin-6-one,
3-(8-Cyclopentyl-6-oxo-1-propyl-6,7-dihydro-1H-purin-2-yloxy)-pyridine-2-carboxylic acid amide,
2-Benzyloxy-8-cyclohexyl-1-propyl-1,7-dihydro-purin-6-one,
8-Cyclohexyl-1-propyl-2-(3-trifluoromethyl-benzyloxy)-1,7-dihydro-purine-6-one,
8-Cyclohexyl-1-propyl-2-(pyridin-4-ylmethoxy)-1,7-dihydro-purin-6-one,
8-Cyclohexyl-1-propyl-2-(thiazol-2-ylsulfanyl)-1,7-dihydro-purin-6-one,
(8-Cyclohexyl-6-oxo-1-propyl-6,7-dihydro-1H-purin-2-ylsulfanyl)-acetic acid,
8-Cyclohexyl-1-propyl-2-(pyridin-3-ylamino)-1,7-dihydro-purin-6-one,
8-Adamantan-1-yl-2-benzyloxy-1-propyl-1,7-dihydro-purin-6-one,
8-Adamantan-1-yl-2-(3-methoxy-benzyloxy)-1-propyl-1,7-dihydro-purin-6-one,
8-Adamantan-1-yl-1-propyl-2-(pyridin-3-ylsulfanyl)-1,7-dihydro-purin-6-one,
8-Adamantan-1-yl-1-propyl-2-(pyridin-4-ylamino)-1,7-dihydro-purin-6-one,
3-[8-(Hexahydro-2,5-methano-pentalen-2-yl)-6-oxo-1-propyl-6,7-dihydro-1H-purin-2-yloxymethyl]-benzoic acid ethyl ester,
3-[8-(Hexahydro-2,5-methano-pentalen-2-yl)-6-oxo-1-propyl-6,7-dihydro-1H-purin-2-yloxy]-pyridine-2-carboxylic acid,
3-[8-(Hexahydro-2,5-methano-pentalen-3a-yl)-6-oxo-1-propyl-6,7-dihydro-1H-purin-2-yloxymethyl]-benzoic acid ethyl ester, 3-[8-(Hexahydro-2,5-methano-pentalen-3a-yl)-6-oxo-1-propyl-6,7-dihydro-1H-purin-2-yloxy]-pyridine-2-carboxylic acid,
8-Bicyclo[2.2.1]hept-2-yl-2-ethylsulfanyl-1-propyl-1,7-dihydro-purin-6-one,
8-Bicyclo[2.2.1]hept-2-yl-2-(3-chloro-benzyloxy)-1-propyl-1,7-dihydro-purin-6-one,
8-Bicyclo[2.2.1]hept-2-yl-2-cyclohexylsulfanyl-1-propyl-1,7-dihydro-purin-6-one,
8-(Hexahydro-2,5-methano-pentalen-3a-yl)-2-(1H-imidazol-2-yloxy)-1-propyl-1,7-dihydro-purin-6-one,
8-Bicyclo[2.2.1]hept-2-yl-1-propyl-2-(pyrimidin-2-yloxy)-1,7-dihydro-purin-6-one,
8-Bicyclo[2.2.1]hept-2-yl-1-propyl-2-([1,3,4]thiadiazol-2-yloxy)-1,7-dihydro-purin-6-one,
2-(4-Methyl-benzyloxy)-8-piperidin-4-yl-1-propyl-1,7-dihydro-purin-6-one,
2-Cyclopentylsulfanyl-8-piperidin-4-yl-1-propyl-1,7-dihydro-purin-6-one,
2-(2-Hydroxy-ethylsulfanyl)-8-piperidin-4-yl-1-propyl-1,7-dihydro-purin-6-one,
8-Piperidin-4-yl-1-propyl-2-(thiazol-2-yloxy)-1,7-dihydro-purin-6-one,
8-Piperidin-4-yl-1-propyl-2-(pyrimidin-2-ylamino)-1,7-dihydro-purin-6-one,
2-(6-Methoxy-pyridin-3-yloxy)-8-piperidin-4-yl-1-propyl-1,7-dihydro-purin-6-one,
8-(1-Methyl-piperidin-4-yl)-1-propyl-2-(pyridin-4-ylamino)-1,7-dihydro-purin-6-one,
8-(1-Methyl-piperidin-4-yl)-1-propyl-2-(pyridin-4-yloxy)-1,7-dihydro-purin-6-one,
2-(3-Methyl-benzyloxy)-8-(1-methyl-piperidin-4-yl)-1-propyl-1,7-dihydro-purin-6-one,
8-(1-Methyl-piperidin-4-yl)-1-propyl-2-(pyridin-4-ylsulfanyl)-1,7-dihydro-purin-6-one,
3-(6-Oxo-2-phenoxy-1-propyl-6,7-dihydro-1H-purin-8-yl)-cyclopentane carboxylic acid,
3-(6-Oxo-2-phenylamino-1-propyl-6,7-dihydro-1H-purin-8-yl)-cyclopentane carboxylic acid,
3-(2-Benzyloxy-6-oxo-1-propyl-6,7-dihydro-1H-purin-8-yl)-cyclopentane carboxylic acid,
3-(2-Cyclopentylsulfanyl-6-oxo-1-propyl-6,7-dihydro-1H-purin-8-yl)-cyclopentane carboxylic acid,
3-(2-Benzylamino-6-oxo-1-propyl-6,7-dihydro-1H-purin-8-yl)-cyclopentane carboxylic acid,
8-(3-Hydroxymethyl-cyclopentyl)-2-phenoxy-1-propyl-1,7-dihydro-purin-6-one,
8-(3-Hydroxymethyl-cyclopentyl)-2-phenylamino-1-propyl-1,7-dihydro-purin-6-one,
4-(6-Oxo-2-phenylamino-1-propyl-6,7-dihydro-1H-purin-8-yl)-cyclohexane carboxylic acid,
4-(6-Oxo-2-phenoxy-1-propyl-6,7-dihydro-1H-purin-8-yl)-cyclohexane carboxylic acid,
[4-(2-Benzyloxy-6-oxo-1-propyl-6,7-dihydro-1H-purin-8-yl)-cyclohexyl]-acetic acid,
2-Benzyloxy-8-cyclopentyl-1-(2-hydroxy-ethyl)-1,7-dihydro-purin-6-one,
3-(8-Cyclopentyl-6-oxo-2-phenoxy-6,7-dihydro-purin-1-yl)-propionic acid,
3-(8-Cyclohexyl-6-oxo-2-phenoxy-6,7-dihydro-purin-1-yl)-propionic acid,
3-(8-Adamantan-1-yl-6-oxo-2-phenoxy-6,7-dihydro-purin-1-yl)-propionic acid,
3-[8-(Hexahydro-2,5-methano-pentalen-3a-yl)-6-oxo-2-phenoxy-6,7-dihydro-purin-1-yl]-propionic acid,
3-(8-Bicyclo[2.2.1]hept-2-yl-6-oxo-2-phenoxy-6,7-dihydro-purin-1-yl)-propionic acid,
3-{4-[2-(3-Methoxy-phenoxy)-6-oxo-1-propyl-6,7-dihydro-1H-purin-8-yl]-bicyclo[2.2.2]oct-1-yl}-propionic acid,
3-[4-(2-Cyclopentyloxy-6-oxo-1-propyl-6,7-dihydro-1H-purin-8-yl)-bicyclo[2.2.2]oct-1-yl]-propionic acid,
3-[4-(2-Cyclopentyloxy-6-oxo-1-propyl-6,7-dihydro-1H-purin-8-yl)-bicyclo[2.2.2]oct-1-yl]-propionamide,
2-(3-Fluoro-phenoxy)-1-propyl-8-[4-(thiazol-2-yloxymethyl)-bicyclo[2.2.2]oct-1-yl]-1,7-dihydro-purin-6-one,
2-{4-[2-(3-Methoxy-phenoxy)-6-oxo-1-propyl-6,7-dihydro-1H-purin-8-yl]-bicyclo[2.2.2]oct-1-ylmethoxy}-thiazole-4-carboxylic acid,
2-(4-Fluoro-benzylamino)-1-propyl-8-[4-(thiazol-2-yloxymethyl)-bicyclo[2.2.2]oct-1-yl]-1,7-dihydro-purin-6-one,
2-{4-[2-(4-Fluoro-benzylamino)-6-oxo-1-propyl-6,7-dihydro-1H-purin-8-yl]bicyclo[2.2.2]oct-1-ylmethoxy}-thiazole-5-carboxylic acid,
2-{4-[2-(3-Fluoro-phenylamino)-6-oxo-1-propyl-6,7-dihydro-1H-purin-8-yl]-bicyclo[2.2.2]oct-1-ylmethoxy}-thiazole-5-carboxylic acid,
2-[4-(2-Cyclopentyloxy-6-oxo-1-propyl-6,7-dihydro-1H-purin-8-yl)-bicyclo[2.2.2]oct-1-ylmethoxy]-thiazole-5-carboxylic acid,
1-Propyl-2-(tetrahydro-furan-3-yloxy)-8-[4-(thiazol-2-yloxymethyl)-bicyclo[2.2.2]oct-1-yl]-1,7-dihydro-purin-6-one,
2-Benzyl-1-propyl-8-[4-(thiazol-2-yloxymethyl)-bicyclo[2.2.2]oct-1-yl]-1,7-dihydro-purin-6-one,
{6-Oxo-1-propyl-8-[4-(thiazol-2-yloxymethyl)-bicyclo[2.2.2]oct-1-yl]-6,7-dihydro-1H-purin-2-ylamino}-acetic acid,
{6-Oxo-1-propyl-8-[4-(pyridin-2-yloxymethyl)-bicyclo[2.2.2]oct-1-yl]-6,7-dihydro-1H-purin-2-yloxy}-aceticacid,
1-Propyl-8-[4-(pyridin-2-yloxymethyl)-bicyclo[2.2.2]oct-1-yl]-2-(3-trifluoromethyl-phenoxy)-1,7-dihydro-purin-6-one,
2-(3-Chloro-phenylamino)-1-propyl-8-[4-(pyridin-2-yloxymethyl)-bicyclo[2.2.2]oct-1-yl]-1,7-dihydro-purin-6-one,
2-(4-Methyl-benzylamino)-1-propyl-8-[4-(pyridin-2-yloxymethyl)-bicyclo[2.2.2]oct-1-yl]-1,7-dihydro-purin-6-one,
6-{4-[2-(4-Fluoro-benzylamino)-6-oxo-1-propyl-6,7-dihydro-1H-purin-8-yl]-bicyclo[2.2.2]oct-1-ylmethoxy}-nicotinic acid,
6-{4-[6-Oxo-1-propyl-2-(tetrahydro-pyran-4-yloxy)-6,7-dihydro-1H-purin-8-yl]-bicyclo[2.2.2]oct-1-ylmethoxy}-nicotinic acid,
2-Ethyl-1-propyl-8-[4-(4-trifluoromethyl-pyridin-2-yloxymethyl)-bicyclo[2.2.2]oct-1-yl]-1,7-dihydro-purin-6-one,
2-Ethyl-1-propyl-8-[4-(pyrimidin-2-yloxymethyl)-bicyclo[2.2.2]oct-1-yl]-1,7-dihydro-purin-6-one,
8-[4-(5-Chloro-pyrimidin-2-yloxymethyl)-bicyclo[2.2.2]oct-1-yl]-2-(3-fluoro-phenoxy)-1-propyl-1,7-dihydro-purin-6-one,
8-[4-(5-Chloro-pyrimidin-2-ylmethoxy)-bicyclo[2.2.2]oct-1-yl]-2-(3-fluoro-phenoxy)-1-propyl-1,7-dihydro-purin-6-one,
8-[4-(4-Fluoro-pyridin-2-ylmethoxy)-bicyclo[2.2.2]oct-1-yl]-1-propyl-2-m-tolyloxy-1,7-dihydro-purin-6-one,
6-[4-(6-Oxo-1-propyl-2-p-tolylamino-6,7-dihydro-1H-purin-8-yl)-bicyclo[2.2.2]oct-1-yloxymethyl]-nicotinic acid,
6-{4-[2-(4-Fluoro-phenoxy)-6-oxo-1-propyl-6,7-dihydro-1H-purin-8-yl]-bicyclo[2.2.2]oct-1-ylamino}-nicotinic acid, 2-Cyclopentyloxy-8-[4-(5-fluoro-pyridin-2-ylamino)-bicyclo[2.2.2]oct-1-yl]-1-propyl-1,7-dihydro-purin-6-one,
2-Cyclopentyloxy-1-propyl-8-[4-(thiazol-2-ylamino)-bicyclo[2.2.2]oct-1-yl]-1,7-dihydro-purin-6-one,
1-Propyl-8-[4-(thiazol-2-yloxy)-bicyclo[2.2.2]oct-1-yl]-2-m-tolyloxy-1,7-dihydro-purin-6-one,
1-Propyl-8-[3-(thiazol-2-yloxy)-adamantan-1-yl]-2-m-tolyloxy-1,7-dihydro-purin-6-one,
2-{3-[2-(3-Fluoro-phenylamino)-6-oxo-1-propyl-6,7-dihydro-1H-purin-8-yl]-adamantan-1-yloxy}-thiazole-5-carboxylic acid,
2-{3-[2-(3-Fluoro-phenoxy)-6-oxo-1-propyl-6,7-dihydro-1H-purin-8-yl]-adamantan-1-ylamino}-thiazole-4-carboxylic acid,
2-{3-[2-(3-Fluoro-phenoxy)-6-oxo-1-propyl-6,7-dihydro-1H-purin-8-yl]-adamantan-1-yloxymethyl}-thiazole-4-carboxylic acid,
2-Cyclohexyloxy-1-propyl-8-[3-(thiazol-2-ylmethoxy)-adamantan-1-yl]-1,7-dihydro-purin-6-one,
8-[3-(5-Fluoro-pyridin-2-yloxymethyl)-adamantan-1-yl]-2-methoxy-1-propyl-1,7-dihydro-purin-6-one,
2-(3-Fluoro-benzylamino)-8-[3-(5-fluoro-pyridin-2-yloxymethyl)-adamantan-1-yl]-1-propyl-1,7-dihydro-purin-6-one,
8-{3-[(5-Fluoro-pyridin-2-ylamino)-methyl]-adamantan-1-yl}-1-propyl-2-p-tolyloxy-1,7-dihydro-purin-6-one,
2-Benzyl-1-propyl-8-[3-(thiazol-2-ylaminomethyl)-adamantan-1-yl]-1,7-dihydro-purin-6-one,
2-(3-Fluoro-phenoxy)-1-propyl-8-[3-(3-trifluoromethyl-phenoxymethyl)-adamantan-1-yl]-1,7-dihydro-purin-6-one,
3-{3-[6-Oxo-1-propyl-2-(tetrahydro-furan-3-yloxy)-6,7-dihydro-1H-purin-8-yl]-adamantan-1-yloxymethyl}-benzoic acid,
8-[3-(3-Fluoro-benzylamino)-adamantan-1-yl]-2-methoxy-1-propyl-1,7-dihydro-purin-6-one,
2-Ethyl-8-{3-[(5-fluoro-pyridin-3-ylmethyl)-amino]-adamantan-1-yl}-1-propyl-1,7-dihydro-purin-6-one,
1-Propyl-8-{3-[(pyrimidin-5-ylmethyl)-amino]-adamantan-1-yl}-2-m-tolyloxy-1,7-dihydro-purin-6-one,
2-(4-Chloro-phenoxy)-1-propyl-8-{3-[(thiazol-2-ylmethyl)-amino]-adamantan-1-yl}-1,7-dihydro-purin-6-one,
1-Propyl-2-(pyridin-2-yloxy)-8-{3-[(thiazol-2-ylmethyl)-amino]-adamantan-1-yl}-1,7-dihydro-purin-6-one,
2-(6-Methyl-pyridin-2-yloxy)-1-propyl-8-[3-(thiazol-2-ylmethoxy)-adamantan-1-yl]-1,7-dihydro-purin-6-one.

Biological Activity
Radioligand Binding for $A_{2B}$ Adenosine Receptor

Human $A_{2B}$ adenosine receptor cDNA was stably transfected into HEK-293 cells. HEK-$A_{2B}$ cells were harvested by trypsinization with 0.25% Trypsin-EDTA (Sigma), and washed in 1×PBS at 1500 rpm for 5 minutes at room temperature. The cells were washed twice in wash buffer containing 150 mM NaCl, 1 mM EDTA, 50 mM Tris (pH-7.4) at 1500 rpm for 10 minutes at room temperature and incubated for 10 min at 4° C. in sonication buffer containing 1 mM EDTA, 5 mM Tris (pH 7.4). The cells were sonicated on ice for 6 min with six intermittent pulses of 9 second each and centrifuged at 1000×g for 10 minutes at 4° C. The pellet was discarded and the supernatant was centrifuged at 49,000×g for 45 minutes at 4° C. The protein pellet was resuspended in buffer containing 1 mM EDTA, 5 mM Tris (pH-7.4), 1 Unit/ml adenosine deaminase (ADA) and incubated for 30 minutes at room temperature. The lysate was washed twice with buffer containing 1 mM EDTA, 5 mM Tris (pH-7.4) at 49,000×g for 45 minutes at 4° C. and the protein pellet was resuspended in 50 mM Tris, pH-7.4 supplemented with 1 Unit/ml ADA and 10% sucrose. Frozen aliquots were stored at −80° C.

Competition assays were started by mixing 1.6 nM [3H]-MRS-1754 with various concentrations of test compounds and 10 µg membrane protein in Reaction buffer (50 mM Tris pH 6.5, 5 mM $MgCl_2$, 1 mM EDTA) supplemented with 1 U/ml Adenosine deaminase. The assay reactions were incubated for 90 minutes at room temperature and stopped by filtration using 96 well-plate harvester (Molecular Devices) and washed four times with ice cold 50 mM Tris (pH 7.4). Non specific binding was determined in presence of 200 µM NECA. Radioligand binding was read at Liquid scintillation counter (Perkin Elmer) and the affinities of compounds (i.e. $K_i$ values) were calculated using GraphPad software.

Compounds tested had micromolar to nanomolar activity.
Radioligand Binding for $A_1$ Adenosine Receptor Human $A_1$ adenosine receptor cDNA was stably transfected into HEK-293 cells. HEK-$A_1$ cells were harvested by trypsinization with 0.25% Trypsin-EDTA (Sigma), and washed in 1×PBS at 1500 rpm for 5 minutes at room temperature. The cells were washed twice in wash buffer containing 150 mM NaCl, 1 mM EDTA, 50 mM Tris (pH-7.4) at 1500 rpm for 10 minutes at room temperature and incubated for 10 min at 4° C. in sonication buffer containing 1 mM EDTA, 5 mM Tris (pH 7.4). The cells were sonicated on ice for 6 min with six intermittent pulses of 9 seconds each and centrifuged at 1000×g for 10 minutes at 4° C. The pellet was discarded and the supernatant was centrifuged at 49,000×g for 45 minutes at 4° C. The protein pellet was resuspended in buffer containing 1 mM EDTA, 5 mM Tris (pH-7.4), 1 Unit/ml adenosine deaminase (ADA) and incubated for 30 minutes at room temperature. The lysate was washed twice with buffer containing 1 mM EDTA, 5 mM Tris (pH-7.4) at 49,000×g for 45 minutes at 4° C. and the protein pellet was resuspended in 50 mM Tris, (pH-7.4) supplemented with 1 Unit/ml ADA and 10% sucrose. Frozen aliquots were stored at −80° C.

Competition assays were started by mixing 1 nM [3H]-DPCPX with various concentrations of test compounds and 5 µg membrane protein in Reaction buffer (50 mM Tris pH 7.4, 1 mM EDTA) supplemented with 1 Unit/ml ADA. The assay reactions were incubated for 90 minutes at room temperature and stopped by filtration using 96 well-plate harvester (Molecular Devices) and washed four times with ice cold 50 mM Tris (pH 7.4). Non specific binding was determined in presence of 200 µM NECA. Radioligand binding was read at Liquid scintillation counter (Perkin Elmer) and the affinities of compounds (i.e. $K_i$ values) were calculated using GraphPad software.

Compounds tested had micromolar to nanomolar activity.
Radioligand Binding for $A_{2A}$ Adenosine Receptor Human $A_{2A}$ adenosine receptor cDNA was stably transfected into HEK-293 cells. HEK-$A_{2A}$ cells were harvested by trypsinization with 0.25% Trypsin-EDTA (Sigma), and washed in 1×PBS at 1500 rpm for 5 minutes at room temperature. The cells were washed twice in wash buffer containing 150 mM NaCl, 1 mM EDTA, 50 mM Tris (pH-7.4) at 1500 rpm for 10 minutes at room temperature and incubated for 10 min at 4° C. in sonication buffer containing 1 mM EDTA, 5 mM (Tris pH 7.4). The cells were sonicated on ice for 6 min with six intermittent pulses of 9 second each and centrifuged at 1000×g for 10 minutes at 4° C. The pellet was discarded and the supernatant was centrifuged at 49,000×g for 45 minutes at 4° C. The protein pellet was resuspended in buffer containing 1 mM EDTA, 5 mM Tris (pH-7.4) supplemented with 1 Unit/ml adenosine deaminase (ADA) and incubated for 30 minutes at room temperature. The lysate was washed twice with buffer containing 1 mM EDTA, 5 mM Tris (pH-7.4) at 49,000×g for 45 minutes at 4° C. and the protein pellet was resuspended in 50 mM Tris, pH-7.4 supplemented with 1 Unit/ml ADA and 10% sucrose. Frozen aliquots were stored at −80° C.

Competition assays were started by mixing 2 nM [3H]-ZM-241385 with various concentrations of test compounds and 5 μg membrane protein in Reaction buffer (50 mM Tris pH 7.4, 1 mM EDTA) supplemented with 1 Unit/ml ADA. The assay reactions were incubated for 90 minutes at room temperature and stopped by filtration using 96 well-plate harvester (Molecular Devices) and washed four times with ice cold 50 mM Tris (pH 7.4). Non specific binding was determined in presence of 200 NECA. Radioligand binding was read at Liquid scintillation counter (Perkin Elmer) and the affinities of compounds (i.e. $K_i$ values) were calculated using GraphPad software.

Compounds tested had micromolar to nanomolar activity.

Radioligand Binding for $A_3$ Adenosine Receptor

Human $A_3$ adenosine receptor cDNA was stably transfected into HEK-293 cells. HEK-$A_3$ cells were harvested by trypsinization with 0.25% Trypsin-EDTA (Sigma), and washed in 1×PBS at 1500 rpm for 5 minutes at room temperature. The cells were washed twice in wash buffer containing 10 mM EDTA, 10 mM HEPES (pH-7.4) at 1500 rpm for 10 minutes at room temperature and incubated for 10 min at 4° C. in sonication buffer containing 1 mM EDTA, 10 mM HEPES (pH 7.4). The cells were sonicated on ice for 6 min with six intermittent pulses of 9 seconds each and centrifuged at 1000×g for 10 minutes at 4° C. The pellet was discarded and the supernatant was centrifuged at 49,000×g for 45 minutes at 4° C. The protein pellet was resuspended in buffer containing 1 mM EDTA, 10 mM HEPES (pH 7.4) supplemented with 1 Unit/ml adenosine deaminase (ADA) and incubated for 30 minutes at room temperature. The lysate was washed twice with buffer containing 1 mM EDTA, 10 mM HEPES (pH-7.4) at 49,000×g for 45 minutes at 4° C. and the protein pellet was resuspended in buffer containing 1 mM EDTA, 5 mM Tris (pH-7.4) supplemented with 1 Unit/ml ADA and 10% sucrose. Frozen aliquots were stored at −80° C.

Competition assays were started by mixing 2 nM [3H]-HEM-ADO with various concentrations of test compounds and 5 μg membrane protein in Reaction buffer (50 mM Tris pH 7.4, 1 mM EDTA, 10 mM $MgCl_2$) supplemented with 1 Unit/ml ADA. The assay reactions were incubated for 90 minutes at room temperature and stopped by filtration using 96 well-plate harvester (Molecular Devices) and washed four times with ice cold 50 mM Tris pH 7.4. Non specific binding was determined in presence of 200 μM NECA. Radioligand binding was read at Liquid scintillation counter (Perkin Elmer) and the affinities of compounds (i.e. $K_i$ values) were calculated using GraphPad software.

Compounds tested had micromolar to nanomolar activity.

We claim:

1. A compound of formula I

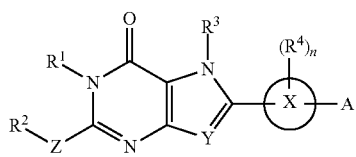

(I)

or a tautomer, polymorph, stereoisomer, solvate, or pharmaceutically acceptable salt thereof, wherein Y is selected from N or CR; R is selected from H, hydroxy, alkoxy, alkyl, aryl;

$R^1$ is selected from a group consisting of alkyl, alkenyl and alkynyl, wherein one or more methylene groups is optionally replaced by groups selected from —O—, —S(O)$_p$—, NR$^a$R$^a$, or —C(O), and wherein the heteroatom is not adjacent to N in the ring; p is selected from 0, 1 or 2;

wherein alkyl, alkenyl and alkynyl are unsubstituted or independently substituted with alkoxy, acyl, acylamino, acyloxy, amino, monoalkylamino, dialkylamino, aminocarbonyl, alkoxycarbonylamino, azido, cyano, halogen, haloalkyl, hydroxy, hydroxyalkyl, keto, thiocarbonyl, carboxy, alkylcarboxy, carboxyalkyl, —SO$_3$H, aminocarbonylamino, hydroxyamino, alkoxyamino, or nitro;

Z is selected from a bond, —O—, —S(O)$_p$—, —NR$^a$, —NR$^a$C(O)— or —NR$^a$S(O)$_2$—;

$R^2$ is selected from a group consisting of alkyl, alkenyl, alkynyl, haloalkyl, aryl, arylalkyl, hydroxyalkyl, carboxyalkyl, cycloalkyl, cycloalkylalkyl, heterocyclyl, heterocyclylalkyl, heteroaryl and heteroarylalkyl;

wherein alkyl, alkenyl, alkynyl, cycloalkyl, cycloalkylalkyl, arylalkyl, aryl, heteroaryl, heteroarylalkyl, heterocyclyl, and heterocyclylalkyl are unsubstituted or independently substituted with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, haloalkyl, perhaloalkyl, CF$_3$, OCF$_3$, hydroxy, hydroxyalkyl, keto, thiocarbonyl, carboxy, alkylcarboxy, carboxyalkyl, —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, —S(O)$_2$NR$^b$R$^b$, —NR$^b$S(O)$_2$R$^b$ or —S(O)$_p$R$^c$;

wherein each substituent is unsubstituted or substituted with 1, 2, or 3 substituents independently selected from alkyl, carboxy, carboxyalkyl, aminocarbonyl, hydroxy, alkoxy, halogen, CF$_3$, amino, substituted amino, cyano or —S(O)$_p$R$^d$;

$R^3$ is selected from a group consisting of hydrogen, alkyl, alkenyl, alkynyl, alkoxyalkyl and arylalkyl;

wherein alkyl, alkenyl, alkynyl, alkoxyalkyl and arylalkyl are unsubstituted or independently substituted with hydroxyl, alkyl, alkenyl, alkynyl or alkoxy;

X is a ($C_3$-$C_{12}$)cycloalkyl;

$R^4$ is selected from hydrogen, cyano, hydroxyl, halogen, alkyl, alkenyl, alkynyl, haloalkyl, hydroxyalkyl, alkoxyalkyl, carboxy, carboxyalkyl, alkoxy or haloalkoxy;

A is selected from a bond, ($C_1$-$C_6$)alkyl, ($C_2$-$C_6$)alkenyl or ($C_2$-$C_6$)alkynyl group; wherein 1 to 4 methylene groups are optionally replaced by groups independently selected from 0, —S(O)$_p$—, or —C(O)—;

wherein A is optionally substituted with B; B is selected from hydrogen, heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy, —$SO_3H$, aryl, aryloxy, cycloalkyloxy, heteroaryl, aminocarbonylamino, heteroaryloxy, heterocyclyl, heterocyclyloxy, hydroxyamino, alkoxyamino, nitro, $S(O)_2NR^bR^b$, —$NR^bS(O)_2R^b$ or —$S(O)_pR^c$;

wherein each substituent is unsubstituted or substituted with 1, 2, or 3 substituents independently selected from alkyl, carboxy, carboxyalkyl, aminocarbonyl, hydroxy, alkoxy, halogen, $CF_3$, amino, substituted amino, cyano or —$S(O)_pR^d$;

each $R^a$ is independently selected from the group consisting of hydrogen and alkyl;

each $R^b$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl;

$R^c$ is hydrogen, alkyl, aryl, heteroaryl or heterocyclyl;

$R^d$ is alkyl, aryl, or heteroaryl;

n is 1 or 2; and p is 0, 1 or 2;

with the proviso that—
i. if A is bond, B and $R^4$ are each hydrogen, then Z is not a bond; and
ii. if Z is a bond, then $R^2$ is not an alkyl, substituted with amino or substituted amino.

2. A compound of formula I as claimed in claim 1 or a tautomer, polymorph, stereoisomer, solvate, or pharmaceutically acceptable salt thereof, wherein Y is N;

$R^1$ is an alkyl wherein one or more methylene groups is optionally replaced by groups selected from —O—, —$S(O)_p$—, $NR^aR^a$, or —C(O) and wherein the heteroatom is not adjacent to N in the ring;

p is selected from 0, 1 or 2;

wherein alkyl is unsubstituted or substituted with alkoxy, acyl, acylamino, acyloxy, amino, monoalkylamino, dialkylamino, aminocarbonyl, alkoxycarbonylamino, azido, cyano, halogen, haloalkyl, hydroxy, hydroxyalkyl, keto, thiocarbonyl, carboxy, alkylcarboxy, carboxyalkyl, —$SO_3H$, aminocarbonylamino, hydroxyamino, alkoxyamino, or nitro;

Z is selected from —O—, —$S(O)_p$—, —$NR^a$, —$NR^aC(O)$— or —$NR^aS(O)_2$—;

$R^2$ is selected from a group consisting of alkyl, haloalkyl, aryl, arylalkyl, hydroxyalkyl, carboxyalkyl, cycloalkyl, cycloalkylalkyl, heterocyclyl, heterocyclylalkyl, heteroaryl and heteroaryl alkyl;

wherein alkyl, cycloalkyl, cycloalkylalkyl, arylalkyl, aryl, heteroaryl, heteroarylalkyl, heterocyclyl, and heterocyclylalkyl are unsubstituted or independently substituted with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, haloalkyl, perhaloalkyl, $CF_3$, $OCF_3$, hydroxy, hydroxyalkyl, keto, thiocarbonyl, carboxy, alkylcarboxy, carboxyalkyl, —$SO_3H$, aryl, aryloxy, cycloalkyloxy, heteroaryl, aminocarbonylamino, heteroaryloxy, heterocyclyl, heterocyclyloxy, hydroxyamino, alkoxyamino, nitro, —$S(O)_2NR^bR^b$, —$NR^bS(O)_2R^b$ or —$S(O)_pR^c$;

$R^3$ is selected from hydrogen or alkyl;

X is a ($C_3$-$C_{12}$)cycloalkyl;

$R^4$ is selected from hydrogen, hydroxyl, halogen, alkyl, haloalkyl, hydroxyalkyl, alkoxyalkyl, carboxy, carboxyalkyl, alkoxy or haloalkoxy;

A is selected from a bond, ($C_1$-$C_6$)alkylene, ($C_2$-$C_6$)alkenylene or ($C_2$-$C_6$)alkynylene group wherein 1 to 4 methylene groups are optionally replaced by groups independently selected from O, —$S(O)_p$—, or —C(O)—;

wherein A is optionally substituted with B; B is selected from heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —$SO_3H$, aryl, aryloxy, cycloalkyloxy, heteroaryl, aminocarbonylamino, heteroaryloxy, heterocyclyl, heterocyclyloxy, hydroxyamino, alkoxyamino, nitro, $S(O)_2NR^bR^b$, —$NR^bS(O)_2R^b$ and —$S(O)_pR^c$;

wherein each substituent is unsubstituted or substituted with 1, 2, or 3 substituents independently selected from alkyl, carboxy, carboxyalkyl, aminocarbonyl, hydroxy, alkoxy, halogen, $CF_3$, amino, substituted amino, cyano or —$S(O)_pR^d$;

each $R^a$ is independently selected from the group consisting of hydrogen and alkyl;

each $R^b$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl;

$R^c$ is hydrogen, alkyl, aryl, heteroaryl or heterocyclyl;

$R^d$ is alkyl, aryl, or heteroaryl;

n is 1 or 2; and p is 0, 1 or 2.

3. A compound of formula I as claimed in claim 1 or a tautomer, polymorph, stereoisomer, solvate, or pharmaceutically acceptable salt thereof, wherein: Y is N;

$R^1$ is an alkyl wherein one or more methylene groups is optionally replaced by groups selected from —O—, —$S(O)_p$—, $NR^aR^a$, or —C(O) and wherein the heteroatom is not adjacent to N in the ring; p is selected from 0, 1 or 2;

Z is —O—;

$R^2$ is selected from a group consisting of alkyl, haloalkyl, aryl, arylalkyl, hydroxyalkyl, carboxyalkyl, cycloalkyl, cycloalkylalkyl, heterocyclyl, heterocyclylalkyl, heteroaryl and heteroarylalkyl;

wherein alkyl, cycloalkyl, cycloalkylalkyl, arylalkyl, aryl, heteroaryl, heteroarylalkyl, heterocyclyl, and heterocyclylalkyl are unsubstituted or substituted independently with alkyl, alkoxy, cycloalkyl, acyl, acylamino, acyloxy, amino, monoalkylamino, dialkylamino, aminocarbonyl, alkoxycarbonylamino, cyano, halogen, haloalkyl, perhaloalkyl, $CF_3$, $OCF_3$, hydroxy, hydroxyalkyl, carboxy, alkylcarboxy, carboxyalkyl, —$SO_3H$, aryl, heteroaryl, aminocarbonylamino, heterocyclyl, hydroxyamino, alkoxyamino, nitro, —$S(O)_2NR^bR^b$, —$NR^bS(O)_2R^b$ or —$S(O)_pR^c$;

$R^3$ is selected from hydrogen or alkyl;

X is a ($C_3$-$C_{12}$)cycloalkyl;

$R^4$ is selected from hydrogen, hydroxyl, halogen, alkyl, haloalkyl, hydroxyalkyl, alkoxyalkyl, carboxy, carboxyalkyl, alkoxy or haloalkoxy;

A is selected from a bond, ($C_1$-$C_6$)alkylene, ($C_2$-$C_6$)alkenylene or ($C_2$-$C_6$)alkynylene group wherein 1 to 4 methylene groups are optionally replaced by group independently selected from O, —S(O)$_p$—, or —C(O)—;
wherein A is optionally substituted with B; B is selected from heterocyclyl, cycloalkyl, aryl or heteroaryl;
wherein heterocyclyl, cycloalkyl, aryl and heteroaryl are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, S(O)$_2$NR$^b$R$^b$, —NR$^b$S(O)$_2$R$^b$ or —S(O)$_p$R$^c$;
wherein each substituent is unsubstituted or substituted with 1, 2, or 3 substituents independently selected from alkyl, carboxy, carboxyalkyl, aminocarbonyl, hydroxy, alkoxy, halogen, CF$_3$, amino, substituted amino, cyano or —S(O)$_p$R$^d$;
each R$^a$ is independently selected from the group consisting of hydrogen and alkyl;
each R$^b$ is independently selected from the group consisting of hydrogen and alkyl;
R$^c$ is hydrogen, alkyl, aryl, heteroaryl or heterocyclyl;
R$^d$ is alkyl, aryl, or heteroaryl;
n is 1 or 2; and p is 0, 1 or 2.

4. A compound of formula I as claimed in claim 1 or a tautomer, polymorph, stereoisomer, solvate, or pharmaceutically acceptable salt thereof, wherein:
Y is N;
R$^1$ is an alkyl wherein one or more methylene groups is optionally replaced by groups selected from —O—, —S(O)$_p$—, NR$^a$R$^a$, or —C(O) and wherein the heteroatom is not adjacent to N in the ring;
p is selected from 0, 1 or 2;
wherein alkyl is unsubstituted or substituted with alkoxy, acyl, acylamino, acyloxy, amino, monoalkylamino, dialkylamino, aminocarbonyl, alkoxycarbonylamino, azido, cyano, halogen, haloalkyl, hydroxy, hydroxyalkyl, keto, thiocarbonyl, carboxy, alkylcarboxy, carboxyalkyl, —SO$_3$H, aminocarbonylamino, hydroxyamino, alkoxyamino, or nitro;
Z is selected from —S(O)$_p$—, —NR$^a$, —NR$^a$C(O)— or —NR$^a$S(O)$_2$—; p is selected from 0, 1 or 2;
R$^2$ is selected from a group consisting of alkyl, haloalkyl, aryl, arylalkyl, hydroxyalkyl, carboxyalkyl, cycloalkyl, cycloalkylalkyl, heterocyclyl, heterocyclylalkyl, heteroaryl and heteroarylalkyl;
wherein alkyl, cycloalkyl, cycloalkylalkyl, arylalkyl, aryl, heteroaryl, heteroarylalkyl, heterocyclyl, and heterocyclylalkyl are unsubstituted or substituted independently with alkyl, alkoxy, cycloalkyl, acyl, acylamino, acyloxy, amino, monoalkylamino, dialkylamino, aminocarbonyl, alkoxycarbonylamino, cyano, halogen, haloalkyl, perhaloalkyl, CF$_3$, OCF$_3$, hydroxy, hydroxyalkyl, carboxy, alkylcarboxy, carboxyalkyl, —SO$_3$H, aryl, heteroaryl, aminocarbonylamino, heterocyclyl, hydroxyamino, alkoxyamino, nitro, —S(O)$_2$NR$^b$R$^b$, —NR$^b$S(O)$_2$R$^b$ or —S(O)$_p$R$^c$;
R$^3$ is selected from hydrogen or alkyl;
X is a (C$_3$-C$_{12}$)cycloalkyl;
R$^4$ is selected from hydrogen, hydroxyl, halogen, alkyl, haloalkyl, hydroxyalkyl, alkoxyalkyl, carboxy, carboxyalkyl, alkoxy or haloalkoxy;
A is selected from a bond, (C$_1$-C$_6$)alkylene, (C$_2$-C$_6$)alkenylene or (C$_2$-C$_6$)alkynylene group wherein 1 to 4 methylene groups are optionally replaced by group independently selected from O, —S(O)$_p$—, or —C(O)—;
wherein A is optionally substituted with B; B is selected from heterocyclyl, cycloalkyl, aryl or heteroaryl;
wherein heterocyclyl, cycloalkyl, aryl and heteroaryl are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy, —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, S(O)$_2$NR$^b$R$^b$, —NR$^b$S(O)$_2$R$^b$ or —S(O)$_p$R$^c$;
wherein each substituent is unsubstituted or substituted with 1, 2, or 3 substituents independently selected from alkyl, carboxy, carboxyalkyl, aminocarbonyl, hydroxy, alkoxy, halogen, CF$_3$, amino, substituted amino, cyano or —S(O)$_p$R$^d$;
each R$^a$ is independently selected from the group consisting of hydrogen and alkyl;
each R$^b$ is independently selected from the group consisting of hydrogen and alkyl;
R$^c$ is hydrogen, alkyl, aryl, heteroaryl or heterocyclyl;
R$^d$ is alkyl, aryl, or heteroaryl;
n is 1 or 2; and p is 0, 1 or 2.

5. A compound of formula I as claimed in claim 1 or a tautomer, polymorph, stereoisomer, solvate, or pharmaceutically acceptable salt thereof, wherein:
Y is N;
R$^1$ is an alkyl;
Z is selected from a bond, —O— or —NR$^a$;
R$^2$ is selected from a group consisting of alkyl, haloalkyl, aryl, arylalkyl, hydroxyalkyl, carboxyalkyl, cycloalkyl, cycloalkylalkyl, heterocyclyl, heterocyclylalkyl, heteroaryl and heteroarylalkyl;
wherein alkyl, cycloalkyl, cycloalkylalkyl, arylalkyl, aryl, heteroaryl, heteroarylalkyl, heterocyclyl, and heterocyclylalkyl are unsubstituted or substituted independently with alkyl, alkoxy, cycloalkyl, acyl, acylamino, acyloxy, amino, monoalkylamino, dialkylamino, aminocarbonyl, alkoxycarbonylamino, cyano, halogen, haloalkyl, perhaloalkyl, CF$_3$, OCF$_3$, hydroxy, hydroxyalkyl, carboxy, alkylcarboxy, carboxyalkyl, —SO$_3$H, aryl, heteroaryl, aminocarbonylamino, heterocyclyl, hydroxyamino, alkoxyamino, nitro, —S(O)$_2$NR$^b$R$^b$, —NR$^b$S(O)$_2$R$^b$ or —S(O)$_p$R$^c$;
R$^3$ is selected from hydrogen or alkyl;
X is selected from:

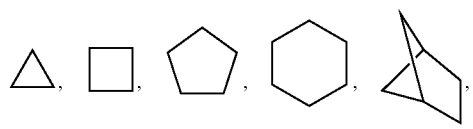

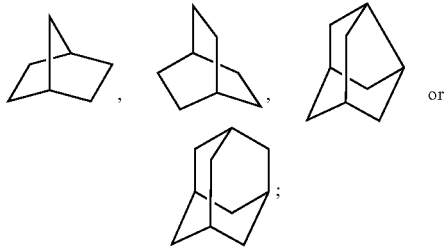

R⁴ is selected from hydrogen, hydroxyl, halogen, alkyl, haloalkyl, hydroxyalkyl, alkoxyalkyl, carboxy, carboxyalkyl, alkoxy or haloalkoxy;

A is selected from a bond or $(C_1$-$C_6)$alkylene group wherein 1 to 4 methylene groups is optionally replaced by group independently selected from 0, —S(O)$_p$—, or —C(O)—;

wherein A is optionally substituted with B; B is selected from heterocyclyl, cycloalkyl, aryl or heteroaryl;

wherein heterocyclyl, cycloalkyl, aryl and heteroaryl are unsubstituted or substituted independently with alkyl, alkoxy, acyl, acylamino, acyloxy, amino, monoalkylamino, dialkylamino, aminocarbonyl, alkoxycarbonylamino, cyano, halogen, hydroxy, hydroxyalkyl, carboxy, alkylcarboxy, carboxyalkyl, carboxyalkyloxy, alkylcarboxyalkyloxy, —SO₃H, aminocarbonylamino, hydroxyamino, alkoxyamino, nitro, S(O)$_2$NR$^b$R$^b$, —NR$^b$S(O)$_2$R$^b$ and —S(O)$_p$R$^c$;

each R$^a$ is independently selected from the group consisting of hydrogen, alkyl;
each R$^b$ is independently selected from the group consisting of hydrogen and alkyl;
R$^c$ is hydrogen, alkyl, aryl, heteroaryl or heterocyclyl;
R$^d$ is alkyl, aryl, or heteroaryl;
n is 1 or 2; and p is 0, 1 or 2.

6. A compound of formula I as claimed in claim 1, or a tautomer, polymorph, stereoisomer, solvate, or pharmaceutically acceptable salt thereof, which is 8-Adamantan-1-yl-2-(2-hydroxy-ethylamino)-1-propyl-1,7-dihydro-purin-6-one,
8-Adamantan-1-yl-2-(2,4-difluoro-benzylamino)-1-propyl-1,7-dihydro-purin-6-one,
8-Cyclopentyl-2-(2-hydroxy-ethylamino)-1-propyl-1,7-dihydro-purin-6-one,
8-Cyclopentyl-2-(2,4-difluoro-benzylamino)-1-propyl-1,7-dihydro-purin-6-one,
8-Cyclopentyl-2-(3,4-difluoro-phenoxy)-1-propyl-1,7-dihydro-purin-6-one,
8-Cyclopentyl-2-methoxy-1-propyl-1,7-dihydro-purin-6-one,
8-Cyclopentyl-2-(2-fluoro-phenoxy)-1-propyl-1,7-dihydro-purin-6-one,
8-Adamantan-1-yl-2-(4-fluoro-phenoxy)-1-propyl-1,7-dihydro-purin-6-one,
8-Adamantan-1-yl-2-(3-fluoro-phenoxy)-1-propyl-1,7-dihydro-purin-6-one,
8-Adamantan-1-yl-2-(3,4-difluoro-phenoxy)-1-propyl-1,7-dihydro-purin-6-one,
8-Cyclopentyl-2-ethoxy-1-propyl-1,7-dihydro-purin-6-one,
8-Adamantan-1-yl-2-methylamino-1-propyl-1,7-dihydro-purin-6-one,
8-Adamantan-1-yl-2-dimethylamino-1-propyl-1,7-dihydro-purin-6-one,
(8-Cyclopentyl-6-oxo-1-propyl-6,7-dihydro-1H-purin-2-yloxy)-acetic acid ethyl ester,
(8-Cyclopentyl-6-oxo-1-propyl-6,7-dihydro-1H-purin-2-yloxy)-acetic acid,
8-Bicyclo[2.2.1]hept-2-yl-2-chloro-1-propyl-1,7-dihydro-purin-6-one,
(8-Cyclopentyl-6-oxo-1-propyl-6,7-dihydro-1H-purin-2-ylamino)-acetic acid ethyl ester,
(8-Cyclopentyl-6-oxo-1-propyl-6,7-dihydro-1H-purin-2-ylamino)-acetic acid,
(8-Adamantan-1-yl-6-oxo-1-propyl-6,7-dihydro-1H-purin-2-yloxy)-acetic acid,
8-Cyclopentyl-1-propyl-2-(2-trifluoromethyl-benzylamino)-1,7-dihydro-purin-6-one,
8-Cyclopentyl-1-propyl-2-(4-trifluoromethyl-benzylamino)-1,7-dihydro-purin-6-one,
8-Cyclopentyl-2-(2,6-difluoro-benzylamino)-1-propyl-1,7-dihydro-purin-6-one,
8-Cyclopentyl-2-(2-methoxy-benzylamino)-1-propyl-1,7-dihydro-purin-6-one,
8-Cyclopentyl-1-propyl-2-(2-trifluoromethoxy-benzylamino)-1,7-dihydro-purin-6-one,
8-Cyclopentyl-2-(4-fluoro-benzylamino)-1-propyl-1,7-dihydro-purin-6-one,
8-Cyclopentyl-2-phenethylamino-1-propyl-1,7-dihydro-purin-6-one,
8-Cyclopentyl-2-(4-methyl-benzylamino)-1-propyl-1,7-dihydro-purin-6-one,
8-Cyclopentyl-1-propyl-2-[(thiophen-2-ylmethyl)-amino]-1,7-dihydro-purin-6-one,
4-[(8-Cyclopentyl-6-oxo-1-propyl-6,7-dihydro-1H-purin-2-ylamino)-methyl]-benzoic acid methyl ester,
4-[(8-Cyclopentyl-6-oxo-1-propyl-6,7-dihydro-1H-purin-2-ylamino)-methyl]-benzoic acid,
8-Cyclohexyl-2-cyclopentyloxy-1-propyl-1,7-dihydro-purin-6-one,
8-Cyclopentyl-2-phenylamino-1-propyl-1,7-dihydro-purin-6-one,
8-Cyclopentyl-2-(4-fluoro-phenylamino)-1-propyl-1,7-dihydro-purin-6-one,
2-(3-Chloro-benzylamino)-8-cyclopentyl-1-propyl-1,7-dihydro-purin-6-one,
8-Cyclopentyl-2-cyclopentyloxy-1-propyl-1,7-dihydro-purin-6-one,
8-Cyclopentyl-2-(3-fluoro-phenoxy)-1-propyl-1,7-dihydro-purin-6-one,
8-Cyclopentyl-2-(3-methoxy-phenoxy)-1-propyl-1,7-dihydro-purin-6-one,
8-Cyclohexyl-2-(3-fluoro-phenoxy)-1-propyl-1,7-dihydro-purin-6-one,
2-(3-Fluoro-phenoxy)-8-(hexahydro-2,5-methano-pentalen-3a-yl)-1-propyl-1,7-dihydro-purin-6-one,
2-(3,4-Difluoro-phenoxy)-8-(hexahydro-2,5-methano-pentalen-3a-yl)-1-propyl-1,7-dihydro-purin-6-one,
8-(Hexahydro-2,5-methano-pentalen-3a-yl)-2-(4-methyl-benzylamino)-1-propyl-1,7-dihydro-purin-6-one,
8-(Hexahydro-2,5-methano-pentalen-3a-yl)-1-propyl-2-(4-trifluoromethyl-benzylamino)-1,7-dihydro-purin-6-one,
2-Cyclopentyloxy-8-(hexahydro-2,5-methano-pentalen-3a-yl)-1-propyl-1,7-dihydro-purin-6-one,
8-Cyclohexyl-2-(4-fluoro-benzylamino)-1-propyl-1,7-dihydro-purin-6-one,
2-(8-Cyclohexyl-6-oxo-1-propyl-6,7-dihydro-1H-purin-2-ylamino)-3-(3-fluoro-phenyl)-propionic acid,
4-[8-(Hexahydro-2,5-methano-pentalen-3a-yl)-6-oxo-1-propyl-6,7-dihydro-1H-purin-2-yloxy]-benzoic acid, 3-[8-(Hexahydro-2,5-methano-pentalen-3a-yl)-6-oxo-1-propyl-6,7-dihydro-1H-purin-2-yloxy]-benzoic acid,
{4-[8-(Hexahydro-2,5-methano-pentalen-3a-yl)-6-oxo-1-propyl-6,7-dihydro-1H-purin-2-yloxy]-phenyl}-acetic acid,
8-Cyclohexyl-1-propyl-2-(pyridin-3-yloxy)-1,7-dihydro-purin-6-one,
2-Cyclopentyloxy-8-cyclopropyl-1-propyl-1,7-dihydro-purin-6-one,
8-Cyclohexyl-2-(4-fluoro-phenoxy)-1-propyl-1,7-dihydro-purin-6-one,
8-Cyclohexyl-2-(3-methoxy-phenoxy)-1-propyl-1,7-dihydro-purin-6-one,
4-(8-Cyclohexyl-6-oxo-1-propyl-6,7-dihydro-1H-purin-2-yloxy)-benzoic acid,
8-Cyclohexyl-1-propyl-2-m-tolyloxy-1,7-dihydro-purin-6-one,
N-[4-(8-Cyclohexyl-6-oxo-1-propyl-6,7-dihydro-1H-purin-2-yloxy)-phenyl]-acetamide,
2-Cyclohexyl-5-[4-(1-hydroxy-ethyl)-phenoxy]-6-propyl-1,6-dihydro-imidazo[4,5-b]pyridin-7-one,
8-Cyclohexyl-2-(2,4-dichloro-phenoxy)-1-propyl-1,7-dihydro-purin-6-one,
8-Cyclohexyl-2-(4-fluoro-2-methoxy-phenoxy)-1-propyl-1,7-dihydro-purin-6-one,
2-(2-Chloro-4-fluoro-phenoxy)-8-cyclohexyl-1-propyl-1,7-dihydro-purin-6-one,
8-Cyclohexyl-2-(3,4-dimethyl-phenoxy)-1-propyl-1,7-dihydro-purin-6-one,
8-Cyclopentyl-1-propyl-2-(3-trifluoromethyl-phenoxy)-1,7-dihydro-purin-6-one,
8-Cyclopentyl-2-(4-fluoro-2-methoxy-phenoxy)-1-propyl-1,7-dihydro-purin-6-one,
4-[2-(3-Methoxy-phenoxy)-6-oxo-1-propyl-6,7-dihydro-1H-purin-8-yl]-bicyclo[2.2.2]octane-1-carboxylic acid,
8-Cyclopentyl-2-(2,4-dichloro-phenoxy)-1-propyl-1,7-dihydro-purin-6-one,
2-(4-Chloro-2-methoxy-phenoxy)-8-cyclopentyl-1-propyl-1,7-dihydro-purin-6-one,
2-(2-Chloro-4-fluoro-phenoxy)-8-cyclopentyl-1-propyl-1,7-dihydro-purin-6-one,
8-Cyclopentyl-2-(3,4-dimethyl-phenoxy)-1-propyl-1,7-dihydro-purin-6-one,
4-(8-Cyclopentyl-6-oxo-1-propyl-6,7-dihydro-1H-purin-2-yloxy)-benzamide,
8-Cyclopentyl-2-(6-methyl-pyridin-3-yloxy)-1-propyl-1,7-dihydro-purin-6-one,
2-(5-Chloro-pyridin-3-yloxy)-8-cyclopentyl-1-propyl-1,7-dihydro-purin-6-one,
8-Cyclopentyl-2-(1H-indol-5-yloxy)-1-propyl-1,7-dihydro-purin-6-one,
8-Cyclopentyl-2-(4-fluoro-3-trifluoromethyl-phenoxy)-1-propyl-1,7-dihydro-purin-6-one,
8-Cyclohexyl-1-propyl-2-(3-trifluoromethyl-phenoxy)-1,7-dihydro-purin-6-one,
2-(Benzo[1,3]dioxol-5-yloxy)-8-cyclohexyl-1-propyl-1,7-dihydro-purin-6-one,
4-(8-Cyclohexyl-6-oxo-1-propyl-6,7-dihydro-1H-purin-2-yloxy)-benzenesulfonamide,
8-Cyclohexyl-1-propyl-2-[(S)-(tetrahydro-furan-3-yl)oxy]-1,7-dihydro-purin-6-one,
2-(3-Acetyl-phenoxy)-8-cyclohexyl-1-propyl-1,7-dihydro-purin-6-one,
8-Cyclohexyl-2-[3-(1-hydroxy-ethyl)-phenoxy]-1-propyl-1,7-dihydro-purin-6-one,
6-Cyclohexyl-2-((R)-3-methyl-tetrahydro-furan-3-yloxy)-3-propyl-3,5-dihydro-pyrrolo[3,2-d]pyrimidin-4-one,
8-Cyclopentyl-2-(5-methyl-pyridin-2-yloxy)-1-propyl-1,7-dihydro-purin-6-one,
[3-(8-Cyclopentyl-6-oxo-1-propyl-6,7-dihydro-1H-purin-2-yloxy)-phenyl]-acetic acid,
[4-(8-Cyclopentyl-6-oxo-1-propyl-6,7-dihydro-1H-purin-2-yloxy)-3-fluoro-phenyl]-acetic acid,
8-Cyclopentyl-2-(6-methyl-pyridin-2-yloxy)-1-propyl-1,7-dihydro-purin-6-one,
8-Cyclopentyl-2-(4-fluoro-3-methyl-phenoxy)-1-propyl-1,7-dihydro-purin-6-one,
2-(Benzo[1,3]dioxol-5-yloxy)-8-cyclopentyl-1-propyl-1,7-dihydro-purin-6-one,
8-Cyclopentyl-2-(4-fluoro-2-trifluoromethyl-phenoxy)-1-propyl-1,7-dihydro-purin-6-one,
8-Cyclopentyl-1-propyl-2-(3-trifluoromethoxy-phenoxy)-1,7-dihydro-purin-6-one,
4-[2-(3-Fluoro-phenoxy)-6-oxo-1-propyl-6,7-dihydro-1H-purin-8-yl]-bicyclo[2.2.2]octane-1-carboxylic acid,
4-(8-Cyclopentyl-6-oxo-1-propyl-6,7-dihydro-1H-purin-2-yloxy)-benzenesulfonamide,
8-Cyclopentyl-2-(1-methyl-pyrrolidin-3-yloxy)-1-propyl-,7-dihydro-purin-6-one,
8-Cyclopentyl-2-(1-methyl-piperidin-4-yloxy)-1-propyl-1,7-dihydro-purin-6-one,
8-Cyclopentyl-1-propyl-2-(tetrahydro-furan-3-yloxy)-1,7-dihydro-purin-6-one,
8-Cyclopentyl-1-propyl-2-(tetrahydro-pyran-4-yloxy)-1,7-dihydro-purin-6-one,
8-Cyclopentyl-2-(3-hydroxy-phenoxy)-1-propyl-1,7-dihydro-purin-6-one,
8-(3,4-Dihydroxy-cyclopentyl)-2-(3-methoxy-phenoxy)-1-propyl-1,7-dihydro-purin-6-one,
8-Cyclopentyl-1-propyl-2-(3-trifluoromethyl-henylamino)-1,7-dihydro-purin-6-one,
8-Cyclopentyl-2-(3-fluoro-phenylamino)-1-propyl-1,7-dihydro-purin-6-one,
3-(8-Cyclopentyl-6-oxo-1-propyl-6,7-dihydro-1H-purin-2-yloxy)-benzoic acid methyl ester,
2-(3-Acetyl-phenoxy)-8-cyclopentyl-1-propyl-1,7-dihydro-purin-6-one,
8-Cyclopentyl-2-[3-(1-hydroxy-ethyl)-phenoxy]-1-propyl-1,7-dihydro-purin-6-one,
8-Cyclopentyl-2-[3-(1-hydroxy-1-methyl-ethyl)-phenoxy]-1-propyl-1,7-dihydro-purin-6-one,
3-(8-Cyclopentyl-6-oxo-1-propyl-6,7-dihydro-1H-purin-2-yloxy)-benzoic acid,
3-(8-Cyclopentyl-6-oxo-1-propyl-6,7-dihydro-1H-purin-2-yloxy)-benzamide,
8-Cyclopentyl-1-propyl-2-(6-trifluoromethyl-pyridin-2-yloxy)-1,7-dihydro-purin-6-one,
8-Cyclopentyl-1-propyl-2-(5-trifluoromethyl-pyridin-2-yloxy)-1,7-dihydro-purin-6-one,
8-Cyclopentyl-2-(2-methyl-pyridin-3-yloxy)-1-propyl-1,7-dihydro-purin-6-one,
3-(8-Cyclopentyl-6-oxo-1-propyl-6,7-dihydro-1H-purin-2-yloxy)-benzonitrile,
8-Cyclopentyl-2-(1H-indol-7-yloxy)-1-propyl-1,7-dihydro-purin-6-one,
8-Cyclopentyl-2-(1H-indol-4-yloxy)-1-propyl-1,7-dihydro-purin-6-one,
8-Cyclopentyl-2-(3-hydroxy-cyclopentyloxy)-1-propyl-1,7-dihydro-purin-6-one,
8-Cyclopentyl-1-propyl-2-[(S)-(tetrahydro-furan-3-yl)oxy]-1,7-dihydro-purin-6-one, 8-Cyclopentyl-1-propyl-2-[(R)-(tetrahydro-furan-3-yl)oxy]-1,7-dihydro-purin-6-one,
2-(6-Chloro-pyridin-2-yloxy)-8-cyclopentyl-1-propyl-1,7-dihydro-purin-6-one,
2-Chloro-8-cyclopentyl-1-isobutyl-1,7-dihydro-purin-6-one,
8-[4-(5-Chloro-pyridin-2-yloxymethyl)-bicyclo[2.2.2]oct-1-yl]-2-(3,4-difluoro-phenoxy)-1-propyl-1,7-dihydro-purin-6-one,
2-Cyclopentyloxy-1-propyl-8-[4-(pyridin-2-yloxymethyl)-bicyclo[2.2.2]oct-1-yl]-1,7-dihydro-purin-6-one,
8-[4-(5-Chloro-pyridin-2-yloxymethyl)-bicyclo[2.2.2]oct-1-yl]-2-(2-methyl-pyridin-3-yloxy)-1-propyl-1,7-dihydro-purin-6-one,
8-Cyclopentyl-2-(4-methyl-pyridin-2-yloxy)-1-propyl-1,7-dihydro-purin-6-one,
8-Cyclopentyl-2-(2-methyl-1-oxy-pyridin-3-yloxy)-1-propyl-1,7-dihydro-purin-6-one,
8-Cyclopentyl-2-(2-oxo-1,2-dihydro-pyridin-4-yloxy)-1-propyl-1,7-dihydro-purin-6-one,
8-Cyclopentyl-2-(2-oxo-1,2-dihydro-pyridin-3-yloxy)-1-propyl-1,7-dihydro-purin-6-one,
2-(2-Chloro-pyridin-3-yloxy)-8-cyclopentyl-1-propyl-1,7-dihydro-purin-6-one,
8-Cyclopentyl-1-propyl-2-o-tolyloxy-1,7-dihydro-purin-6-one,
8-Cyclopentyl-1-isobutyl-2-(2-methyl-pyridin-3-yloxy)-1,7-dihydro-purin-6-one,
8-Cyclopentyl-2-(4-fluoro-2-isoxazol-5-yl-phenoxy)-1-propyl-1,7-dihydro-purin-6-one,
2-(8-Chloro-quinolin-2-yloxy)-8-cyclopentyl-1-propyl-1,7-dihydro-purin-6-one,
8-Cyclopentyl-2-[4-fluoro-2-(1H-pyrazol-3-yl)-phenoxy]-1-propyl-1,7-dihydro-purin-6-one,
8-Cyclopentyl-2-[4-fluoro-2-(2H-pyrazol-3-yl)-phenoxy]-1-propyl-1,7-dihydro-purin-6-one,
8-Cyclopentyl-2-(2,6-dimethyl-pyridin-3-yloxy)-1-propyl-1,7-dihydro-purin-6-one,
2-Benzyloxy-8-cyclopentyl-1-propyl-1,7-dihydro-purin-6-one,
8-Cyclopentyl-2-(3,5-difluoro-benzyloxy)-1-propyl-1,7-dihydro-purin-6-one,
8-Cyclopentyl-1-propyl-2-(pyridin-3-ylmethoxy)-1,7-dihydro-purin-6-one,
2-But-2-ynyloxy-8-cyclopentyl-1-propyl-1,7-dihydro-purin-6-one,
8-Cyclopentyl-1-propyl-2-(pyrimidin-2-yloxy)-1,7-dihydro-purin-6-one,
8-Cyclopentyl-1-propyl-2-(pyridin-2-ylsulfanyl)-1,7-dihydro-purin-6-one,
8-Cyclopentyl-2-(1H-imidazol-2-ylsulfanyl)-1-propyl-1,7-dihydro-purin-6-one,
8-Cyclopentyl-2-ethanesulfonyl-1-propyl-1,7-dihydro-purin-6-one,
8-Cyclopentyl-2-ethylsulfanyl-1-propyl-1,7-dihydro-purin-6-one,
2-Cyclohexylsulfanyl-8-cyclopentyl-1-propyl-1,7-dihydro-purin-6-one,
(8-Cyclopentyl-6-oxo-1-propyl-6,7-dihydro-1H-purin-2-ylsulfanyl)-acetic acid ethyl ester,
8-Cyclopentyl-1-propyl-2-(pyrimidin-2-ylamino)-1,7-dihydro-purin-6-one,
3-(8-Cyclopentyl-6-oxo-1-propyl-6,7-dihydro-1H-purin-2-yloxy)-pyridine-2-carboxylic acid amide,
2-Benzyloxy-8-cyclohexyl-1-propyl-1,7-dihydro-purin-6-one,
8-Cyclohexyl-1-propyl-2-(3-trifluoromethyl-benzyloxy)-1,7-dihydro-purine-6-one,
8-Cyclohexyl-1-propyl-2-(pyridin-4-ylmethoxy)-1,7-dihydro-purin-6-one,
8-Cyclohexyl-1-propyl-2-(thiazol-2-ylsulfanyl)-1,7-dihydro-purin-6-one,
(8-Cyclohexyl-6-oxo-1-propyl-6,7-dihydro-1H-purin-2-ylsulfanyl)-acetic acid,
8-Cyclohexyl-1-propyl-2-(pyridin-3-ylamino)-1,7-dihydro-purin-6-one,
8-Adamantan-1-yl-2-benzyloxy-1-propyl-1,7-dihydro-purin-6-one,
8-Adamantan-1-yl-2-(3-methoxy-benzyloxy)-1-propyl-1,7-dihydro-purin-6-one,
8-Adamantan-1-yl-1-propyl-2-(pyridin-3-ylsulfanyl)-1,7-dihydro-purin-6-one,
8-Adamantan-1-yl-1-propyl-2-(pyridin-4-ylamino)-1,7-dihydro-purin-6-one,
3-[8-(Hexahydro-2,5-methano-pentalen-2-yl)-6-oxo-1-propyl-6,7-dihydro-1H-purin-2-yloxymethyl]-benzoic acid ethyl ester,
3-[8-(Hexahydro-2,5-methano-pentalen-2-yl)-6-oxo-1-propyl-6,7-dihydro-1H-purin-2-yloxy]-pyridine-2-carboxylic acid,
3-[8-(Hexahydro-2,5-methano-pentalen-3a-yl)-6-oxo-1-propyl-6,7-dihydro-1H-purin-2-yloxymethyl]-benzoic acid ethyl ester,
3-[8-(Hexahydro-2,5-methano-pentalen-3a-yl)-6-oxo-1-propyl-6,7-dihydro-1H-purin-2-yloxy]-pyridine-2-carboxylic acid,
8-Bicyclo[2.2.1]hept-2-yl-2-ethylsulfanyl-1-propyl-1,7-dihydro-purin-6-one,
8-Bicyclo[2.2.1]hept-2-yl-2-(3-chloro-benzyloxy)-1-propyl-1,7-dihydro-purin-6-one,
8-Bicyclo[2.2.1]hept-2-yl-2-cyclohexylsulfanyl-1-propyl-1,7-dihydro-purin-6-one,
8-(Hexahydro-2,5-methano-pentalen-3a-yl)-2-(1H-imidazol-2-yloxy)-1-propyl-1,7-dihydro-purin-6-one,
8-Bicyclo[2.2.1]hept-2-yl-1-propyl-2-(pyrimidin-2-yloxy)-1,7-dihydro-purin-6-one,
8-Bicyclo[2.2.1]hept-2-yl-1-propyl-2-([1,3,4]thiadiazol-2-yloxy)-1,7-dihydro-purin-6-one,
3-(6-oxo-2-phenoxy-1-propyl-6,7-dihydro-1H-purin-8-yl)-cyclopentane carboxylic acid,
3-(6-oxo-2-phenylamino-1-propyl-6,7-dihydro-1H-purin-8-yl)-cyclopentane carboxylic acid,
3-(2-Benzyloxy-6-oxo-1-propyl-6,7-dihydro-1H-purin-8-yl)-cyclopentane carboxylic acid,
3-(2-Cyclopentylsulfanyl-6-oxo-1-propyl-6,7-dihydro-1H-purin-8-yl)-cyclopentane carboxylic acid,
3-(2-Benzylamino-6-oxo-1-propyl-6,7-dihydro-1H-purin-8-yl)-cyclopentane carboxylic acid,
8-(3-Hydroxymethyl-cyclopentyl)-2-phenoxy-1-propyl-1,7-dihydro-purin-6-one,
8-(3-Hydroxymethyl-cyclopentyl)-2-phenylamino-1-propyl-1,7-dihydro-purin-6-one,
4-(6-oxo-2-phenylamino-1-propyl-6,7-dihydro-1H-purin-8-yl)-cyclohexane carboxylic acid,
4-(6-Oxo-2-phenoxy-1-propyl-6,7-dihydro-1H-purin-8-yl)-cyclohexane carboxylic acid,
[4-(2-Benzyloxy-6-oxo-1-propyl-6,7-dihydro-1H-purin-8-yl)-cyclohexyl]-acetic acid,
2-Benzyloxy-8-cyclopentyl-1-(2-hydroxy-ethyl)-1,7-dihydro-purin-6-one,
3-(8-Cyclopentyl-6-oxo-2-phenoxy-6,7-dihydro-purin-1-yl)-propionic acid, 3-(8-Cyclohexyl-6-oxo-2-phenoxy-6,7-dihydro-purin-1-yl)-propionic acid,
3-(8-Adamantan-1-yl-6-oxo-2-phenoxy-6,7-dihydro-purin-1-yl)-propionic acid,
3-[8-(Hexahydro-2,5-methano-pentalen-3a-yl)-6-oxo-2-phenoxy-6,7-dihydro-purin-1-yl]-propionic acid,
3-(8-Bicyclo[2.2.1]hept-2-yl-6-oxo-2-phenoxy-6,7-dihydro-purin-1-yl)-propionic acid,
3-{4-[2-(3-Methoxy-phenoxy)-6-oxo-1-propyl-6,7-dihydro-1H-purin-8-yl]-bicyclo[2.2.2]oct-1-yl}-propionic acid,
3-[4-(2-Cyclopentyloxy-6-oxo-1-propyl-6,7-dihydro-1H-purin-8-yl)-bicyclo[2.2.2]oct-1-yl]-propionic acid,
3-[4-(2-Cyclopentyloxy-6-oxo-1-propyl-6,7-dihydro-1H-purin-8-yl)-bicyclo[2.2.2]oct-1-yl]-propionamide,
2-(3-Fluoro-phenoxy)-1-propyl-8-[4-(thiazol-2-yloxymethyl)-bicyclo[2.2.2]oct-1-yl]-1,7-dihydro-purin-6-one,
2-{4-[2-(3-Methoxy-phenoxy)-6-oxo-1-propyl-6,7-dihydro-1H-purin-8-yl]-bicyclo[2.2.2]oct-1-ylmethoxy}-thiazole-4-carboxylic acid,
2-(4-Fluoro-benzylamino)-1-propyl-8-[4-(thiazol-2-yloxymethyl)-bicyclo[2.2.2]oct-1-yl]-1,7-dihydro-purin-6-one,
2-{4-[2-(4-Fluoro-benzylamino)-6-oxo-1-propyl-6,7-dihydro-1H-purin-8-yl]bicyclo[2.2.2]oct-1-ylmethoxy}-thiazole-5-carboxylic acid,
2-{4-[2-(3-Fluoro-phenylamino)-6-oxo-1-propyl-6,7-dihydro-1H-purin-8-yl]-bicyclo[2.2.2]oct-1-ylmethoxy}-thiazole-5-carboxylic acid,
2-[4-(2-Cyclopentyloxy-6-oxo-1-propyl-6,7-dihydro-1H-purin-8-yl)-bicyclo[2.2.2]oct-1-ylmethoxy]-thiazole-5-carboxylic acid,
1-Propyl-2-(tetrahydro-furan-3-yloxy)-8-[4-(thiazol-2-yloxymethyl)-bicyclo[2.2.2]oct-1-yl]-1,7-dihydro-purin-6-one,
2-Benzyl-1-propyl-8-[4-(thiazol-2-yloxymethyl)-bicyclo[2.2.2]oct-1-yl]-1,7-dihydro-purin-6-one,
{6-oxo-1-propyl-8-[4-(thiazol-2-yloxymethyl)-bicyclo[2.2.2]oct-1-yl]-6,7-dihydro-1H-purin-2-ylamino}-acetic acid,
{6-oxo-1-propyl-8-[4-(pyridin-2-yloxymethyl)-bicyclo[2.2.2]oct-1-yl]-6,7-dihydro-1H-purin-2-yloxy}-aceticacid,
1-Propyl-8-[4-(pyridin-2-yloxymethyl)-bicyclo[2.2.2]oct-1-yl]-2-(3-trifluoromethyl-phenoxy)-1,7-dihydro-purin-6-one,
2-(3-Chloro-phenylamino)-1-propyl-8-[4-(pyridin-2-yloxymethyl)-bicyclo[2.2.2]oct-1-yl]-1,7-dihydro-purin-6-one,
2-(4-Methyl-benzylamino)-1-propyl-8-[4-(pyridin-2-yloxymethyl)-bicyclo[2.2.2]oct-1-yl]-1,7-dihydro-purin-6-one,
6-{4-[2-(4-Fluoro-benzylamino)-6-oxo-1-propyl-6,7-dihydro-1H-purin-8-yl]-bicyclo[2.2.2]oct-1-ylmethoxy}-nicotinic acid,
6-{4-[6-Oxo-1-propyl-2-(tetrahydro-pyran-4-yloxy)-6,7-dihydro-1H-purin-8-yl]-bicyclo[2.2.2]oct-1-ylmethoxy}-nicotinic acid,
2-Ethyl-1-propyl-8-[4-(4-trifluoromethyl-pyridin-2-yloxymethyl)-bicyclo[2.2.2]oct-1-yl]-1,7-dihydro-purin-6-one,
2-Ethyl-1-propyl-8-[4-(pyrimidin-2-yloxymethyl)-bicyclo[2.2.2]oct-1-yl]-1,7-dihydro-purin-6-one,
8-[4-(5-Chloro-pyrimidin-2-yloxymethyl)-bicyclo[2.2.2]oct-1-yl]-2-(3-fluoro-phenoxy)-1-propyl-1,7-dihydro-purin-6-one,
8-[4-(5-Chloro-pyrimidin-2-ylmethoxy)-bicyclo[2.2.2]oct-1-yl]-2-(3-fluoro-phenoxy)-1-propyl-1,7-dihydro-purin-6-one,
8-[4-(4-Fluoro-pyridin-2-ylmethoxy)-bicyclo[2.2.2]oct-1-yl]-1-propyl-2-m-tolyloxy-1,7-dihydro-purin-6-one,
6-[4-(6-Oxo-1-propyl-2-p-tolylamino-6,7-dihydro-1H-purin-8-yl)-bicyclo[2.2.2]oct-1-yloxymethyl]-nicotinic acid,
6-{4-[2-(4-Fluoro-phenoxy)-6-oxo-1-propyl-6,7-dihydro-1H-purin-8-yl]-bicyclo[2.2.2]oct-1-ylamino}-nicotinic acid,
2-Cyclopentyloxy-8-[4-(5-fluoro-pyridin-2-ylamino)-bicyclo[2.2.2]oct-1-yl]-1-propyl-1,7-dihydro-purin-6-one,
2-Cyclopentyloxy-1-propyl-8-[4-(thiazol-2-ylamino)-bicyclo[2.2.2]oct-1-yl]-1,7-dihydro-purin-6-one,
1-Propyl-8-[4-(thiazol-2-yloxy)-bicyclo[2.2.2]oct-1-yl]-2-m-tolyloxy-1,7-dihydro-purin-6-one,
1-Propyl-8-[3-(thiazol-2-yloxy)-adamantan-1-yl]-2-m-tolyloxy-1,7-dihydro-purin-6-one,
2-{3-[2-(3-Fluoro-phenylamino)-6-oxo-1-propyl-6,7-dihydro-1H-purin-8-yl]-adamantan-1-yloxy}-thiazole-5-carboxylic acid,
2-{3-[2-(3-Fluoro-phenoxy)-6-oxo-1-propyl-6,7-dihydro-1H-purin-8-yl]-adamantan-1-ylamino}-thiazole-4-carboxylic acid,
2-{3-[2-(3-Fluoro-phenoxy)-6-oxo-1-propyl-6,7-dihydro-1H-purin-8-yl]-adamantan-1-yloxymethyl}-thiazole-4-carboxylic acid,
2-Cyclohexyloxy-1-propyl-8-[3-(thiazol-2-ylmethoxy)-adamantan-1-yl]-1,7-dihydro-purin-6-one,
8-[3-(5-Fluoro-pyridin-2-yloxymethyl)-adamantan-1-yl]-2-methoxy-1-propyl-1,7-dihydro-purin-6-one,
2-(3-Fluoro-benzylamino)-8-[3-(5-fluoro-pyridin-2-yloxymethyl)-adamantan-1-yl]-1-propyl-1,7-dihydro-purin-6-one,
8-{3-[(5-Fluoro-pyridin-2-ylamino)-methyl]-adamantan-1-yl}-1-propyl-2-p-tolyloxy-1,7-dihydro-purin-6-one,
2-Benzyl-1-propyl-8-[3-(thiazol-2-ylaminomethyl)-adamantan-1-yl]-1,7-dihydro-purin-6-one,
2-(3-Fluoro-phenoxy)-1-propyl-8-[3-(3-trifluoromethyl-phenoxymethyl)-adamantan-1-yl]-1,7-dihydro-purin-6-one,
3-{3-[6-Oxo-1-propyl-2-(tetrahydro-furan-3-yloxy)-6,7-dihydro-1H-purin-8-yl]-adamantan-1-yloxymethyl}-benzoic acid,
8-[3-(3-Fluoro-benzylamino)-adamantan-1-yl]-2-methoxy-1-propyl-1,7-dihydro-purin-6-one,
2-Ethyl-8-{3-[(5-fluoro-pyridin-3-ylmethyl)-amino]-adamantan-1-yl}-1-propyl-1,7-dihydro-purin-6-one,
1-Propyl-8-{3-[(pyrimidin-5-ylmethyl)-amino]-adamantan-1-yl}-2-m-tolyloxy-1,7-dihydro-purin-6-one,
2-(4-Chloro-phenoxy)-1-propyl-8-{3-[(thiazol-2-ylmethyl)-amino]-adamantan-1-yl}-1,7-dihydro-purin-6-one,
1-Propyl-2-(pyridin-2-yloxy)-8-{3-[(thiazol-2-ylmethyl)-amino]-adamantan-1-yl}-1,7-dihydro-purin-6-one and
2-(6-Methyl-pyridin-2-yloxy)-1-propyl-8-[3-(thiazol-2-ylmethoxy)-adamantan-1-yl]-1,7-dihydro-purin-6-one.

7. A method for the modulation of adenosine $A_1$ receptor activity in a mammal, the method comprising administering to the mammal an effective amount of a compound of formula (I) according to claim 1, or a tautomer, polymorph, stereoisomer, solvate or pharmaceutically acceptable salt thereof.

8. A method for the modulation of adenosine $A_{2A}$ receptor activity in a mammal, the method comprising administering to the mammal an effective amount of a compound of formula (I) according to claim 1, or a tautomer, polymorph, stereoisomer, solvate or pharmaceutically acceptable salt thereof.

9. A method for the modulation of adenosine $A_{2B}$ receptor activity in a mammal, the method comprising administering to the mammal an effective amount of a compound of formula (I) according to claim 1, or a tautomer, polymorph, stereoisomer, solvate or pharmaceutically acceptable salt thereof.

10. A method for the modulation of adenosine $A_1$ and $A_{2A}$, or $A_1$ and $A_{2B}$, or $A_1$, $A_{2A}$ and $A_{2B}$ receptor activity in a mammal, the method comprising administering to the mammal an effective amount of an adenosine $A_1$ and $A_{2A}$ antagonist, or adenosine $A_1$ and $A_{2B}$ antagonist, or $A_1$, $A_{2A}$ and $A_{2B}$ antagonist compound of formula (I) according to claim 1, or a tautomer, polymorph, stereoisomer, solvate or pharmaceutically acceptable salt thereof, thereby providing dual or pan antagonistic activity through additive or/and synergistic effect.

11. A pharmaceutical composition comprising, as an active ingredient, at least one compound of formula (I), as claimed in claim 1, or a tautomer, polymorph, stereoisomer, solvate or pharmaceutically acceptable salt thereof, together with one or more pharmaceutically acceptable carriers or excipients.

12. A pharmaceutical composition comprising a compound of formula I as claimed in claim 1, or a tautomer, polymorph, stereoisomer, solvate or pharmaceutically acceptable salt thereof, in combination with one or more second therapeutically active agents.

13. The pharmaceutical composition as claimed in claim 12 wherein, the second therapeutically active agent is selected from anti-inflammatory agent, anti-diabetic agent, anti-hypertensive agent or anti-dyslipidemic agent.

14. The pharmaceutical composition as claimed in claim 12, wherein the second therapeutically active agent is selected from anticholinergic agent, antimuscarinic agent, steroid, LTB4 (leukotriene B4) antagonist, dopamine receptor agonists, phosphodiesterase 4 inhibitor, beta-2 adrenergic receptor agonist, insulin, insulin derivatives and mimetics, insulin secretagogues, insulinotropic sulfonylurea receptor ligands, thiazolidone derivatives, glycogen synthase kinase-3 inhibitor, sodium-dependent glucose co-transporter inhibitor, glycogen phosphorylase A inhibitor, biguanide, alpha-glucosidase inhibitor, glucagon like peptide-1 (GLP-I), GLP-1 analogs and GLP-I mimetics, modulators of peroxisome proliferator-activated receptors, dipeptidyl peptidase IV inhibitor, stearoyl-CoA desaturase-1 inhibitor, diacylglycerol acyltransferase 1 and 2 inhibitor, acetyl CoA carboxylase 2 inhibitor, and breakers of advanced glycation end products, loop diuretics, angiotensin converting enzyme inhibitor, inhibitor of the Na-K-ATPase membrane pump, neutralendopeptidase (NEP) inhibitor, ACE/NEP inhibitors, angiotensin II antagonists, renin inhibitors, β-adrenergic receptor blockers, inotropic agents, calcium channel blockers, aldosterone receptor antagonists, and aldosterone synthase inhibitors, 3-hydroxy-3-methyl-glutaryl coenzyme A reductase inhibitor, HDL increasing compound, squalene synthase inhibitor, farnesoid X receptor and liver X receptor ligand, cholestyramine, fibrates, nicotinic acid, or aspirin.

15. The composition of claim 14, wherein the inhibitor of the Na-K-ATPase membrane pump is digoxin.

16. The composition of claim 14, wherein the HDL increasing compound is a cholesterol ester transfer protein inhibitor.

* * * * *